(12) United States Patent
Gant et al.

(10) Patent No.: US 7,863,308 B2
(45) Date of Patent: Jan. 4, 2011

(54) SUBSTITUTED THIOPHENES

(75) Inventors: Thomas G. Gant, Carlsbad, CA (US); Sepehr Sarshar, Cardiff by the Sea, CA (US)

(73) Assignee: Auspex Pharmaceuticals, Inc., Vista, CA (US)

( * ) Notice: Subject to any disclaimer, the term of this patent is extended or adjusted under 35 U.S.C. 154(b) by 0 days.

(21) Appl. No.: 12/100,555

(22) Filed: Apr. 10, 2008

(65) Prior Publication Data

US 2008/0255036 A1    Oct. 16, 2008

Related U.S. Application Data

(60) Provisional application No. 60/911,036, filed on Apr. 10, 2007.

(51) Int. Cl.
*A61K 31/422*    (2006.01)
*C07D 261/06*    (2006.01)

(52) U.S. Cl. .................. 514/380; 548/245; 548/247

(58) Field of Classification Search ............ 514/380; 548/245, 247
See application file for complete search history.

(56) References Cited

U.S. PATENT DOCUMENTS

| | | | |
|---|---|---|---|
| 2002/0013372 | A1 | 1/2002 | Ekins |
| 2008/0033011 | A1 | 2/2008 | Tung |
| 2008/0242687 | A1 | 10/2008 | Gant et al. |
| 2008/0262006 | A1 | 10/2008 | Harbeson |
| 2009/0005394 | A1 | 1/2009 | Harbeson |
| 2009/0069351 | A1 | 3/2009 | Czarnik |
| 2009/0069352 | A1 | 3/2009 | Czarnik |
| 2009/0069353 | A1 | 3/2009 | Czarnik |
| 2009/0069402 | A1 | 3/2009 | Czarnik |
| 2010/0063076 | A1 | 3/2010 | Harbeson |
| 2010/0093758 | A1 | 4/2010 | Sarshar et al. |

FOREIGN PATENT DOCUMENTS

| | | | |
|---|---|---|---|
| WO | 9526325 | A2 | 10/1995 |
| WO | 9631492 | A1 | 10/1996 |
| WO | 00149685 | A2 | 7/2001 |
| WO | 2008088727 | | 7/2008 |
| WO | 2008097468 | A2 | 8/2008 |
| WO | 2008122020 | | 10/2008 |
| WO | 2008124803 | | 10/2008 |
| WO | 2010011868 | | 1/2010 |

OTHER PUBLICATIONS

Wu, Chengde, et al, Endothelin Antagonists: Substituted Mesitylcarboxamides with High Potency and Selectivity for ETA Receptors, J. Med. Chem. 1999, 42, 4485-4499.

Bauer, LA. et al; Influence of long-term infusions on lidocaine kinetics; Clin. Pharmacol. Ther. 1982, 433-7.

Borgstrom, L. et al; Comparative Pharmacokinetics of Unlabeled and Deuterium-Labeled Terbutaline: Demonstration of a Small Isotope Effect; J Pharm Sci, 1988, 77(11), 952-4.

Browne, TR; Chapter 2. Isotope Effect: Implications for Pharmaceutical Investigations; Pharm Lib 1997 13.

Browne, TR et al.; Pharmacokinetic Equivalence of Stable-Isotope-Labeled and Unlabeled Drugs. Phenobarbital in Man; J Clin Pharmacol, 1982, 22, 309-315.

Burm, AGL et al; Pharmacokinetics of Lidocaine and bupivacaine and stable isotope-labeled analogs: a study in healthy volunteers; Biopharmaceutics and Drug Disposition, 1988, 9, 85-95.

Elison, C. et al; Effect of Deuteration of N-CH$_{3}$ Group on Potency and Enzymatic N-Demethylation of Morphine; Science, 1961, 134(3485), 1078-9.

Farmer, PB et al; Synthesis, Metabolism, and Antitumor Activity of Deuterated Analogues of 1-(2-Choloroethyl)-3-cyclohexyl-1-nitrosourea; Journal of Medicinal Chemistry, 1978, vol. 21, No. 6, 514-20.

Fisher, MB et al; The complexities inherent in attempts to decrease drug clearance by blocking sites of CYP-mediated metabolism; Curr Opin Drug Discov Develop; 2006, 9(1), 101-9.

Foster, AB; Deuterium Isotope Effects in Studies of Drug Metabolism; Trends in Pharmacological Sciences, Dec. 1984, 524-7.

Helfenbein, J. et al; Isotopic Effect Study of Propofol Deuteration on the Metabolism, Activity, and Toxicity of the Anesthetic; J. Med. Chem. 2002, 45, 5806-5808.

Kushner, DJ. et al; Pharmacological uses and perspectives of heavy water and deuterated compounds; Can J Phys Pharm 1999, 77, 79-88.

Lee, H. et al; Deuterium Magic Angle Spinning Studies of Substrates Bound to Cytochrome P450; Biochemistry 1999, 38, 10808-10813.

Mamada, K. et al; Pharmacokinetic Equivalence of Deuterium-Labeled and Unlabeled Phenytoin; Drug Metabolism and Disposition, 1986, 14(4), 509-11.

(Continued)

*Primary Examiner*—Kamal A Saeed
*Assistant Examiner*—Samantha L Shterengarts
(74) *Attorney, Agent, or Firm*—Dennis A. Bennett; Michael Sertic

(57) ABSTRACT

Disclosed herein are substituted pyrimidine-based endothelin modulators of Formula I, processes of preparation thereof, pharmaceutical compositions thereof, and methods of use thereof.

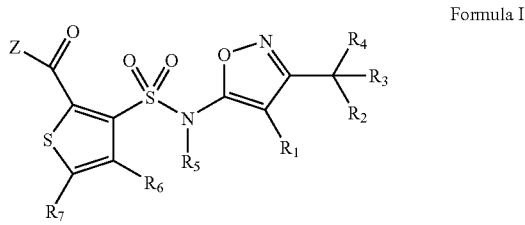

Formula I

30 Claims, No Drawings

OTHER PUBLICATIONS

Nelson, SD et al; The Use of Deuterium Isotope Effect to Probe the Active Site Properties, Mechanism of Cytochrome P450-catalyzed Reactions, and Mechanisms of Metabolically Dependent Toxicity; Drug Metabolism and Disposition 31:1481-1498, 2003.

Nelson, SD et al; Primary and B-Secondary Deuterium Isotope Effects in N-Deethylation Reactions; Journal of Medicinal Chemistry, 1975, vol. 18, No. 11.

Pohl, L.R. et al; Determination of toxic Pathways of Metabolism by Deuterium Substitution; Drug_Metabolism_Rev_1985_1335.

Rampe, D. et al; Deuterated Analogs of verapamil and nifedipine. Synthesis and biological activity; Eur J Med Chem (1993) 28,259-263.

Wu, C;et al; Endothelin Antagonists: Substituted Mesitylcarboxamides with High Potency and Selectivity for ETa Receptors; J. Med. Chem., 1999, 42, 4485-99.

Lausecker, B. et al; Determination of an endothelin receptor antagonist in human plasma by narrow-bore liquid chromatography and ionspray tandem mass spectrometry; Journal of Chromatography A, 1995, 712, 75-83.

Lausecker, B. et al; Simultaneous determination of bosentan and its three major metabolites in various biological matrices and species using narrow bore liquid chromatography with ion spray tandem mass spectrometric detection; Journal of Chromatography B, 2000, 749, 67-83.

Lausecker, B. et al; Development of a liquid chromatographic/tandem mass spectrometric assay for a new endothelin receptor antagonist, and its application to dog plasma samples generated after simultaneous i.v. and p.o. administration of the unlabeled and deuterium-labeled forms of this antagonist; Journal of Mass Spectrometry, 2003, 38, 649-58.

Dell, D. et al; Evolving bioanalytical methods for the cardiovascular drug bosentan; Chromatographia, 2002, 55 (suppl), s-115-S-120.

SUBSTITUTED THIOPHENES

This application claims the benefit of priority of U.S. provisional application No. 60/911,036, filed Apr. 10, 2007, the disclosure of which is hereby incorporated by reference as if written herein in its entirety.

FIELD

The present invention is directed to thiophene-based endothelin modulators, pharmaceutically acceptable salts and prodrugs thereof, the chemical synthesis thereof, and medical use of such compounds for the treatment and/or management of endothelin-mediated disorders.

BACKGROUND

Sitaxsentan (Thelin®), (2-[2-(6-methyl-benzo[1,3]dioxol-5-yl)-acetyl]-thiophene-3-sulfonic acid (4-chloro-3-methyl-isoxazol-5-yl)-amide) is a purported selective endothelin receptor A ($ET_A$) antagonist that is approved by the Food and Drug Administration for the treatment of hypertension and heart failure. Sitaxsentan, the first $ET_A$-selective EMA-approved member of this mechanistic class, blocks the binding of the neurohormone endothelin-1 (ET-1) to $ET_A$. TBC3711 (3-(3,4-dimethyl-isoxazol-5-ylsulfamoyl)-thiophene-2-carboxylic acid (2-acetyl-4,6-dimethyl-phenyl)-amide), another member of this class, is currently undergoing clinical trials (O'Callaghan et al., *International Journal of Clinical Practice* 2006, 60(4), 475-481; Souza et al., *International Journal of Clinical Practice* 2007, 61(1), 153-156; Wu et al., *Journal of Medicinal Chemistry* 1999, 42(22), 4485-4499).

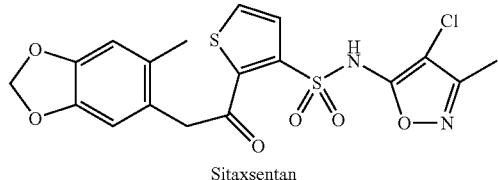
Sitaxsentan

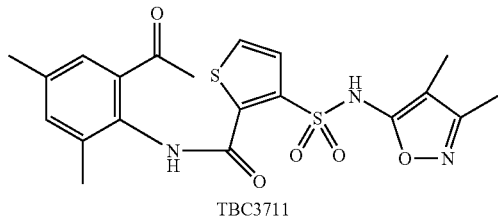
TBC3711

A common and severe side effect of sitaxsentan administration is hepatotoxicity. This hepatotoxicity is likely related to sixaxsentan's metablolism. The methylenedioxy moiety of sitaxsentan is a potential site of oxidative metabolism, which can undergo further biotransformations to form a reactive electrophilic metabolite. This electrophic metabolite could then account for the hepatotoxicity. Sitaxsentan is also known to significantly inhibit CYP2C9, one of the enzymes responsible for its oxidative transformation in vivo. Accordingly, sitaxsentan may cause undesirable drug-drug interactions when coadministered with other medications.

SUMMARY OF THE INVENTION

Disclosed herein is a compound having structural Formula I

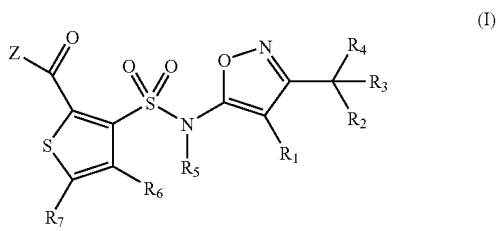

or a pharmaceutically acceptable salt, solvate, or prodrug thereof;
wherein:
$R_1$ is selected from the group consisting of chloride, and

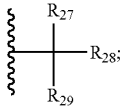

Z is selected from the group consisting of

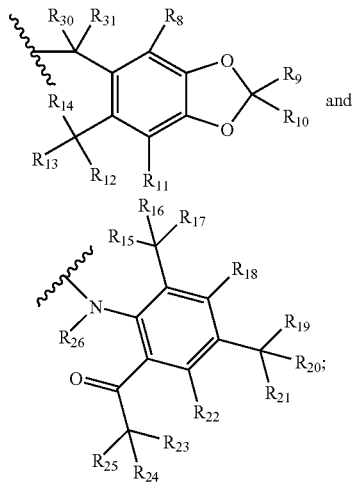

$R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are independently selected from the group consisting of hydrogen and deuterium; and
at least one of $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ is deuterium. Additionally, disclosed herein are methods of modulating endothelin receptors.

Further disclosed herein is a method for treating, preventing, or ameliorating one or more symptoms of a endothelin-mediated disorder which comprises administering to a subject a therapeutically effective amount of at least one compound as disclosed herein or a pharmaceutically acceptable salt, solvate, or prodrug thereof.

Additionally disclosed is a method for treating, preventing, or ameliorating one or more symptoms of a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can be lessened, alleviated, or prevented by administering an endothelin receptor modulator.

Also disclosed herein are articles of manufacture and kits containing compounds as disclosed herein. By way of example only a kit or article of manufacture can include a container (such as a bottle) with a desired amount of at least one compound (or pharmaceutical composition of a compound) as disclosed herein. Further, such a kit or article of manufacture can further include instructions for using said compound (or pharmaceutical composition of a compound) disclosed herein. The instructions can be attached to the container, or can be included in a package (such as a box or a plastic or foil bag) holding the container.

In another aspect is the use of at least one compound as disclosed herein in the manufacture of a medicament for treating a disorder in a subject in which modulating endothelin receptors contributes to the pathology and/or symptomology of the disorder. In a further or alternative embodiment, said disorder is, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can be lessened, alleviated, or prevented by administering an endothelin receptor modulator.

In another aspect are processes for preparing a compound as disclosed herein as an endothelin receptor modulator, or other pharmaceutically acceptable derivatives such as salts, solvates, or prodrugs Also disclosed herein are processes for formulating pharmaceutical compositions with a compound disclosed herein.

In further embodiments, said pharmaceutical composition comprises a compound disclosed herein and one or more pharmaceutically acceptable carriers.

In certain embodiments said pharmaceutical composition comprises one or more release-controlling excipients.

In other embodiments said pharmaceutical composition further comprises one or more non-release controlling excipients.

In certain embodiments said pharmaceutical composition is suitable for oral, parenteral, or intravenous infusion administration.

In yet other embodiments said pharmaceutical composition comprises a tablet or capsule.

In certain embodiments the compounds as disclosed herein are administered in a dose of 0.5 milligram to 1000 milligram.

In yet further embodiments said pharmaceutical compositions further comprise another therapeutic agent.

In other embodiments said therapeutic agent is selected from the group consisting of endothelin antagonists, congestive heart failure treatments, endothelin converting enzyme (ECE) inhibitors, thromboxane enzyme antagonists, potassium channel openers, thrombin inhibitors, growth factor inhibitors, platelet activating factor (PAF) antagonists, anti-platelet agents, Factor VIIa Inhibitors, Factor Xa Inhibitors, renin inhibitors, neutral endopeptidase (NEP) inhibitors, vasopepsidase inhibitors, HMG CoA reductase inhibitors, squalene synthetase inhibitors, fibrates, bile acid sequestrants, anti-atherosclerotic agents, MTP Inhibitors, calcium channel blockers, potassium channel activators, alpha-PDE5 agents, beta-PDE5 agents, antiarrhythmic agents, diuretics, anti-diabetic agents, PPAR-gamma agonists, mineralocorticoid enzyme antagonists, aP2 inhibitors, protein tyrosine kinase inhibitors, antiinflammatories, antiproliferatives, chemotherapeutic agents, immunosuppressants, anticancer agents, cytotoxic agents, antimetabolites, farnesyl-protein transferase inhibitors, hormonal agents, microtubule-disruptor agents, microtubule-stablizing agents, topoisomerase inhibitors, prenyl-protein transferase inhibitors, cyclosporins, TNF-alpha inhibitors, cyclooxygenase-2 (COX-2) inhibitors, gold compounds, and platinum coordination complexes.

In other embodiments said therapeutic agent is an endothelin antagonist.

In further embodiments said endothelin antagonist is selected from the group consisting of cyclic pentapeptides, acyltripeptides, hexapeptide analogs, anthraquinone derivatives, indanecarboxylic acids, N-pyriminylbenzenesulfonamides, benzenesulfonamides, naphthalenesulfonamides, BE-18257B, BQ-123, PD 156707, L-754, 142, SB 209670, SB 217242, A-127722, TAK-044, ambrisentan, bosentan, and sitaxsentan.

In yet further embodiments said endothelin antagonist is selected from an endothelin antagonist identified in the group of patents or patent applications consisting of DE 4341663, EP 743307, EP 733626, EP 713875, EP 682016, EP 658548, EP 633259, EP 628569, EP 617001, EP 601386, EP 555537, EP 552417, EP 526708, EP 510526, EP 496-452, EP 436189, GB 2295616, GB 2277446, GB 2276383, GB 2275926, GB 2266890, JP 8059635, JP 7330622, JP 7316188, JP 7258098, JP 7133254, JP 6256261, JP 6122625, U.S. Pat. No. 6,953, 780, U.S. Pat. No. 6,946,481, U.S. Pat. No. 6,686,382, U.S. Pat. No. 6,683,103, U.S. Pat. No. 6,852,745, U.S. Pat. No. 6,835,741, U.S. Pat. No. 6,673,824, U.S. Pat. No. 6,670,367, U.S. Pat. No. 6,670,362, U.S. Pat. No. 6,432,994, U.S. Pat. No. 6,248,767, U.S. Pat. No. 5,962,490, U.S. Pat. No. 5,783, 705, U.S. Pat. No. 5,594,021, U.S. Pat. No. 5,591,761, U.S. Pat. No. 5,571,821, U.S. Pat. No. 5,514,691, U.S. Pat. No. 5,352,800, U.S. Pat. No. 5,352,659, U.S. Pat. No. 5,334,598, U.S. Pat. No. 5,248,807, U.S. Pat. No. 5,240,910, U.S. Pat. No. 5,198,548, U.S. Pat. No. 5,187,195, U.S. Pat. No. 5,082, 838, U.S. Pat. No. 6,080,774, U.S. Pat. No. 5,780,473, U.S. Pat. No. 5,543,521, U.S. Pat. No. 5,965,732, U.S. Pat. No. 5,571,821, U.S. Pat. No. 5,559,105, U.S. Pat. No. 5,541,186, U.S. Pat. No. 5,482,960, U.S. Pat. No. 5,420,123, U.S. Pat. No. 5,389,620, U.S. Pat. No. 5,292,740, WO 96/33190, WO 96/33170, WO 96/31492, WO 96/30358, WO 96/23773, WO 96/22978, WO 96/20177, WO 96/19459, WO 96/19455, WO 96/15109, WO 96/12706, WO 96/11927, WO 96/11914, WO 96/09818, WO 96/08487, WO 96/08483, WO 96/08486, WO 96/07653, WO 96/06095, WO 96/04905, WO 95/35107, WO 95/33752, WO 95/33748, WO 95/26957, WO 95/26716, WO 95/26360, WO 95/15963, WO 95/15944, WO 95/13262, WO 95/12611, WO 95/05376, WO 95/08989, WO 95/08550, WO 95/05374, WO 95/05372, WO 95/04534, WO 95/04530, WO 95/03295, WO 95/03044, WO 94/25013, WO 94/24084, WO 94/21590, WO 94/21259, WO 94/14434, WO 94/03483, WO 94/02474, WO 93/25580, WO 93/23404, WO 93/21219, and WO 93/08799.

In other embodiments said therapeutic agent is a congestive heart failure treatment.

In yet other embodiments said congestive heart treatment is selected from the group consisting of bumetanide, furosemide, torsemide, chlorthalidone, HCTZ, amiloride, spironolactone, glyceryl trinitrate, isosorbide dinitrate, isosorbide mononitrate, molsidomin pentaerythritol tetranitrate, alprenolol, oxprenolol, pindolol, propranolol, timolol, sotalol, nadolol, mepindolol, carteolol, tertatolol, bopindolol, bupranolol, penbutolol, cloranolol, practolol, metoprolol, atenolol, acebutolol, betaxolol, bevantolol, bisoprolol, celiprolol, esmolol, epanolol, s-atenolol, nebivolol, talinolol, labetalol, carvedilol, amlodipine, felodipine, isradipine, nicardipine, nifedipine, nimodipine, nisoldipine, nitrendipine, lacidipine, nilvadipine, manidipine, barnidipine, lercanidipine, cilnidipine, benidipine, mibefradil, verapamil, gallopamil, diltiazem, fendiline, bepridil, lidoflazine, perhexyline, aliskiren, remikiren, alacepril, benazepril, captopril, ceranapril, delapril, enalapril, fosinopril, lisinopril, moexipril, perindopril, quinapril, ramipril, spirapril, trandolapril, zofenopril candesartan, eprosartan, irbesartan, losartan, olmesartan, tasosartan, telmisartan, valsartan, spironolactone and eplerenone.

In further embodiments of the present invention, a method for the treatment, prevention, or amelioration of one or more symptoms of an endothelin-mediated disorder in a subject by administering a therapeutically effective amount of a compound as disclosed herein.

In other embodiments said endothelin-mediated disorder is selected from the group consisting of hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, and immunosuppressant-mediated renal vasoconstriction.

In further embodiments the endothelin-mediated disorder is pulmonary hypertension.

In certain embodiments the endothelin-mediated disorder is congestive heart failure.

In other embodiments said endothelin-mediated disorder can be lessened, alleviated, or prevented by administering an endothelin receptor modulator.

In other embodiments said compound has at least one of the following properties:
  a) decreased inter-individual variation in plasma levels of said compound or a metabolite thereof as compared to the non-isotopically enriched compound;
  b) increased average plasma levels of said compound per dosage unit thereof as compared to the non-isotopically enriched compound;
  c) decreased average plasma levels of at least one metabolite of said compound per dosage unit thereof as compared to the non-isotopically enriched compound;
  d) increased average plasma levels of at least one metabolite of said compound per dosage unit thereof as compared to the non-isotopically enriched compound; and
  e) an improved clinical effect during the treatment in said subject per dosage unit thereof as compared to the non-isotopically enriched compound.

In yet further embodiments said compound has at least two of the following properties:
  a) decreased inter-individual variation in plasma levels of said compound or a metabolite thereof as compared to the non-isotopically enriched compound;
  b) increased average plasma levels of said compound per dosage unit thereof as compared to the non-isotopically enriched compound;
  c) decreased average plasma levels of at least one metabolite of said compound per dosage unit thereof as compared to the non-isotopically enriched compound;
  d) increased average plasma levels of at least one metabolite of said compound per dosage unit thereof as compared to the non-isotopically enriched compound; and
  e) an improved clinical effect during the treatment in said subject per dosage unit thereof as compared to the non-isotopically enriched compound.

In certain embodiments said compound has a decreased metabolism by at least one polymorphically-expressed cytochrome $P_{450}$ isoform in said subject per dosage unit thereof as compared to the non-isotopically enriched compound.

In other embodiments said cytochrome $P_{450}$ isoform is selected from the group consisting of CYP2C8, CYP2C9, CYP2C19, and CYP2D6.

In yet further embodiments said compound is characterized by decreased inhibition of at least one cytochrome $P_{450}$ or monoamine oxidase isoform in said subject per dosage unit thereof as compared to the non-isotopically enriched compound.

In certain embodiments said cytochrome $P_{450}$ or monoamine oxidase isoform is selected from the group consisting of CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4A1, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, CYP51, MAOA, and MAOB.

In other embodiments said method affects the treatment of the disorder while reducing or eliminating a deleterious change in a diagnostic hepatobiliary function endpoint, as compared to the corresponding non-isotopically enriched compound.

In yet further embodiments said diagnostic hepatobiliary function endpoint is selected from the group consisting of alanine aminotransferase ("ALT"), serum glutamic-pyruvic transaminase ("SGPT"), aspartate aminotransferase ("AST," "SGOT"), ALT/AST ratios, serum aldolase, alkaline phosphatase ("ALP"), ammonia levels, bilirubin, gamma-glutamyl transpeptidase ("GGTP," "γ-GTP," "GGT"), leucine aminopeptidase ("LAP"), liver biopsy, liver ultrasonography, liver nuclear scan, 5'-nucleotidase, and blood protein.

In further embodiments of the present invention, a method for inhibiting the binding of an endothelin to an $ET_A$ or $ET_B$ receptor, comprising contacting the receptor with a compound as recited herein.

In other embodiments said endothelin is endothelin-1, endothelin-2, or endothelin-3.

In yet other embodiments of the present invention, a method for modulating endothelin receptor-mediated activity, comprising contacting an endothelin receptor with a compound as recited herein.

INCORPORATION BY REFERENCE

All publications and references cited herein, including those in the background section, are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

DETAILED DESCRIPTION

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood in the art to which this disclosure belongs. In the event that there is a plurality of definitions for a term used herein, those in this section prevail unless stated otherwise.

As used herein, the singular forms "a," "an," and "the" may refer to plural articles unless specifically stated otherwise.

The term "subject" refers to an animal, including, but not limited to, a primate (e.g., human monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The terms "treat," "treating," and "treatment" are meant to include alleviating or abrogating a disorder; or alleviating or abrogating one or more of the symptoms associated with the disorder; and/or alleviating or eradicating the cause(s) of the disorder itself.

The terms "prevent," "preventing," and "prevention" refer to a method of delaying or precluding the onset of a disorder; delaying or precluding its attendant symptoms; barring a subject from acquiring a disorder; and/or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy*, 21 st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$ and $R_{31}$ or the symbol "D," when used to represent a given position in a drawing of a molecular structure, means that the specified position is enriched with deuterium above the naturally occurring distribution of deuterium. In an embodiment deuterium enrichment is of no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The terms "substantially pure" and "substantially homogeneous" mean sufficiently homogeneous to appear free of readily detectable impurities as determined by standard analytical methods, including, but not limited to, thin layer chromatography (TLC), gel electrophoresis, high performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% of the molecules are a single compound, including a racemic mixture or single stereoisomer thereof, as determined by standard analytical methods.

The term "about" or "approximately" means an acceptable error for a particular value, which depends in part on how the value is measured or determined. In certain embodiments, "about" can mean 1 or more standard deviations.

The terms "active ingredient" and "active substance" refer to a compound, which is administered, alone or in combination with one or more pharmaceutically acceptable excipients and/or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "disorder" as used herein is intended to be generally synonymous, and is used interchangeably with, the terms "disease," "syndrome" and "condition" (as in medical condition), in that all reflect an abnormal condition of the body or of one of its parts that impairs normal functioning and is typically manifested by distinguishing signs and symptoms.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy*, 21 st Edition; Lippincott Williams & Wilkins: Philadelphia, Pa., 2005; *Handbook of Pharmaceutical Excipients*, 5th Edition; Rowe et al., Eds., The Pharmaceutical Press and the American Pharmaceutical Association: 2005; and *Handbook of Pharmaceutical Additives*, 3rd Edition; Ash and Ash Eds., Gower Publishing Company: 2007; *Pharmaceutical Preformulation and Formulation*, Gibson Ed., CRC Press LLC: Boca Raton, Fla., 2004).

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "endothelin" refers to a peptide that has substantially the amino acid sequence of endothelin-1, endothelin-2 or endothelin-3; and acts as a potent endogenous vasoconstrictor peptide.

The terms "endothelin-mediated disorder" refers to a disorder that is characterized by abnormal endothelin activity. An endothelin-mediated disorder may be completely or partially mediated by the abnormal endothelin activity through the interactions of the endothelin with its receptor(s), such as $ET_A$ and $ET_B$. In particular, an endothelin-mediated disorder is one in which modulation of the endothelin activity results in some effect on the underlying disorder, e.g., administration of an $ET_A$ and/or $ET_B$ antagonist or agonist results in some improvement in at least some of patients being treated.

The term "endothelin receptor modulator," refers to the ability of a compound disclosed herein to alter the function of endothelin receptors. A modulator may activate the activity of endothelin receptors, may activate or inhibit the activity of endothelin receptors depending on the concentration of the compound exposed to the endothelin receptors, or may inhibit the activity of endothelin receptors. Such activation or inhibition may be contingent on the occurrence of a specific event, such as activation of a signal transduction pathway, and/or may be manifest only in particular cell types. The term "modulate" or "modulation" also refers to altering the function of endothelin receptors by increasing or decreasing the probability that a complex forms between endothelin receptors and a natural binding partner. A modulator may increase the probability that such a complex forms between the endothelin receptors and the natural binding partner, may increase or decrease the probability that a complex forms between the endothelin receptors and the natural binding partner depending on the concentration of the compound exposed to the endothelin receptors, and or may decrease the probability that a complex forms between the endothelin receptors and the natural binding partner. In some embodiments, modulation of the endothelin receptors may be assessed using Receptor Selection and Amplification Technology (R-SAT) as described in U.S. Pat. No. 5,707,798, the disclosure of which is incorporated herein by reference in its entirety.

The term "endothelin antagonist" refers to a compound that, e.g., partially or totally blocks, decreases, prevents, inhibits, or downregulates endothelin receptor activity. The term "endothelin antagonist" also refers to a compound that binds to, delays the activation of, inactivates, or desensitizes one or more endothelin receptors, such as $ET_A$ and/or $ET_B$. An endothelin antagonist may act by interfering with the interaction of an endothelin with one or more endothelin receptors.

The term "protecting group" or "removable protecting group" refers to a group which, when bound to a functionality, such as the oxygen atom of a hydroxyl or carboxyl group, or the nitrogen atom of an amino group, prevents reactions from occurring at that functional group, and which can be removed by a conventional chemical or enzymatic step to reestablish the functional group.

The term "chlorinating reagent" refers to a reactive chemical reagent used in chlorination reactions, whereby chlorine is transferred to a substrate. Examples of chlorinating agents include, but are not limited to, thionyl chloride, chlorine gas, carbon tetrachloride, cyanuric chloride, hexachloro-2-propanone, N-chlorosuccinimide, phosphorus oxychloride, oxayl chloride, phosphorus pentachloride, phosphorus trichloride, phosphorus (V) oxychloride, and sulfuryl chloride.

The term "coupling reagent" refers to any reagent that will activate the carbonyl of a carboxylic acid and facilitate the formation of an ester or amide bond. The definition of "coupling reagent" includes but is not limited to: acetyl chloride, ethyl chloroformate, 1,1'-carbonyldiimidazole, N,O-dimethylhydroxylamine, dicyclohexylcarbodiimide (DCC), diisopropyl carbodiimide (DIC), 1-ethyl-3-(3-dimethylaminopropyl) carbodiimide (EDCI), N-hydroxybenzotriazole (HOBT), N-hydroxysuccinimide (HOSu), 4-nitrophenol, pentafluorophenol, 2-(1H-benzotriazole-1-yl)-1,1,3,3-tetramethyluronium tetrafluoroborate (TBTU), O-benzotriazole-N,N,N'N'-tetramethyluronium hexafluorophosphate (HBTU), benzotriazole-1-yl-oxy-tris-(dimethylamino)-phosphonium hexafluorophosphate (BOP), benzotriazole-1-yl-oxy-tris-pyrrolidinophosphonium hexafluorophosphate, bromo-trispyrrolidino-phosphonium hexafluorophosphate, 2-(5-norbornene-2,3-dicarboximido)-1,1,3,3-tetramethyluronium tetrafluoroborate (TNTU), O-(N-succinimidyl)-1,1,3,3-tetramethyluronium tetrafluoroborate (TSTU), tetramethylfluoroformamidinium hexafluorophosphate and the like.

The term "catalyst" refers to a substance, which increases the rate of a chemical reaction, which itself is not consumed in an overall chemical or biological reaction. More generally, one may at times call anything that accelerates a process, a "catalyst" (From the Greek καταλνέιν, meaning to annul or to untie or to pick up). A "catalyst" does not allow for a reaction to take place, but it provides an alternative route to products, the catalytic route being subject to lower activation energy than in the uncatalyzed reaction. A lowered activation energy increases the reaction rate. Catalysts generally change in the course of a reaction but are regenerated.

The term "inert gas" refers to any gas that is not reactive under normal circumstances. Like the noble gases the tendency for non-reactivity is due to the valence, the outermost electron shell, being complete in all the inert gases. This is a tendency, not a rule, as noble gases and other "inert" gases can react to form compounds. But unlike the noble gases, an inert gas includes molecular gases as well as elemental gases. Because of the non-reactive properties of inert gases they are often useful to prevent undesirable chemical reactions from taking place. Commonly used inert gases, include, but are not limited to, nitrogen, argon, carbon dioxide, helium, neon, krypton, radon, xenon, fluorocarbons (excepting flammable forms).

The term "halogen", "halide" or "halo" includes fluorine, chlorine, bromine, and iodine.

Deuterium Kinetic Isotope Effect

In an attempt to eliminate foreign substances, such as therapeutic agents, from its circulation system, the animal body expresses various enzymes, such as the cytochrome $P_{450}$ enzymes or CYPs, esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) π-bond. The resultant metabolites may be stable or unstable under physiological conditions, and can have substantially different pharmacokinetic, pharmacodynamic, and acute and long-term toxicity profiles relative to the parent compounds. For most drugs, such oxidations are generally rapid and ultimately lead to administration of multiple or high daily doses.

The relationship between the activation energy and the rate of reaction may be quantified by the Arrhenius equation, $k=Ae^{-E_{act}/RT}$, where $E_{act}$ is the activation energy, T is temperature, R is the molar gas constant, k is the rate constant for the reaction, and A (the frequency factor) is a constant specific to each reaction that depends on the probability that the molecules will collide with the correct orientation. The Arrhenius equation states that the fraction of molecules that have enough energy to overcome an energy barrier, that is, those with energy at least equal to the activation energy, depends exponentially on the ratio of the activation energy to thermal energy (RT), the average amount of thermal energy that molecules possess at a certain temperature.

The transition state in a reaction is a short lived state (on the order of $10^{-14}$ sec) along the reaction pathway during which the original bonds have stretched to their limit. By definition, the activation energy $E_{act}$ for a reaction is the energy required to reach the transition state of that reaction. Reactions that involve multiple steps will necessarily have a number of transition states, and in these instances, the activation energy for the reaction is equal to the energy difference between the reactants and the most unstable transition state. Once the transition state is reached, the molecules can either revert, thus reforming the original reactants, or the new bonds form giving rise to the products. This dichotomy is possible because both pathways, forward and reverse, result in the release of energy. A catalyst facilitates a reaction process by lowering the activation energy leading to a transition state. Enzymes are examples of biological catalysts that reduce the energy necessary to achieve a particular transition state.

A carbon-hydrogen bond is by nature a covalent chemical bond. Such a bond forms when two atoms of similar electronegativity share some of their valence electrons, thereby creating a force that holds the atoms together. This force or bond strength can be quantified and is expressed in units of energy, and as such, covalent bonds between various atoms can be classified according to how much energy must be applied to the bond in order to break the bond or separate the two atoms.

The bond strength is directly proportional to the absolute value of the ground-state vibrational energy of the bond. This vibrational energy, which is also known as the zero-point vibrational energy, depends on the mass of the atoms that form the bond. The absolute value of the zero-point vibrational energy increases as the mass of one or both of the atoms making the bond increases. Since deuterium (D) is two-fold more massive than hydrogen (H), it follows that a C-D bond is stronger than the corresponding C—H bond. Compounds with C-D bonds are frequently indefinitely stable in $H_2O$, and have been widely used for isotopic studies. If a C—H bond is broken during a rate-determining step in a chemical reaction (i.e. the step with the highest transition state energy), then substituting a deuterium for that hydrogen will cause a decrease in the reaction rate and the process will slow down. This phenomenon is known as the Deuterium Kinetic Isotope Effect (DKIE) and can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small size of a hydrogen atom, and occurs because transition states involving a proton can sometimes form in the absence of the required activation energy. A deuterium is larger and statistically has a much lower probability of undergoing this phenomenon. Substitution of tritium for hydrogen results in yet a stronger bond than deuterium and gives numerically larger isotope effects.

Discovered in 1932 by Urey, deuterium (D) is a stable and non-radioactive isotope of hydrogen. It was the first isotope to be separated from its element in pure form and is twice as massive as hydrogen, and makes up about 0.02% of the total mass of hydrogen (in this usage meaning all hydrogen isotopes) on earth. When two deuteriums bond with one oxygen, deuterium oxide ($D_2O$ or "heavy water") is formed. $D_2O$ looks and tastes like $H_2O$, but has different physical properties. It boils at 101.41° C. and freezes at 3.79° C. Its heat capacity, heat of fusion, heat of vaporization, and entropy are all higher than $H_2O$ It is also more viscous and is not as powerful a solvent as $H_2O$.

When pure $D_2O$ is given to rodents, it is readily absorbed and reaches an equilibrium level that is usually about eighty percent of the concentration of what was consumed. The quantity of deuterium required to induce toxicity is extremely high. When 0% to as much as 15% of the body water has been replaced by $D_2O$, animals are healthy but are unable to gain weight as fast as the control (untreated) group. When about 15% to about 20% of the body water has been replaced with $D_2O$, the animals become excitable. When about 20% to about 25% of the body water has been replaced with $D_2O$, the animals are so excitable that they go into frequent convulsions when stimulated. Skin lesions, ulcers on the paws and muzzles, and necrosis of the tails appear. The animals also become very aggressive; males becoming almost unmanageable. When about 30%, of the body water has been replaced with $D_2O$, the animals refuse to eat and become comatose. Their body weight drops sharply and their metabolic rates drop far below normal, with death occurring at about 30 to about 35% replacement with $D_2O$. The effects are reversible unless more than thirty percent of the previous body weight has been lost due to $D_2O$, Studies have also shown that the use of $D_2O$ can delay the growth of cancer cells and enhance the cytotoxicity of certain antineoplastic agents.

Tritium (T) is a radioactive isotope of hydrogen, used in research, fusion reactors, neutron generators and radiopharmaceuticals. Mixing tritium with a phosphor provides a continuous light source, a technique that is commonly used in wristwatches, compasses, rifle sights and exit signs. It was discovered by Rutherford, Oliphant and Harteck in 1934, and is produced naturally in the upper atmosphere when cosmic rays react with $H_2$ molecules. Tritium is a hydrogen atom that has 2 neutrons in the nucleus and has an atomic weight close to 3. It occurs naturally in the environment in very low concentrations, most commonly found as $T_2O$, a colorless and odorless liquid. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level.

Deuteration of pharmaceuticals to improve pharmacokinetics (PK), pharmacodynamics (PD), and toxicity profiles, has been demonstrated previously with some classes of drugs. For example, DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching which may even give rise to an oxidative intermediate with a faster off-rate from an activating Phase I enzyme (e.g., cytochrome $P_{450}$ 3A4). The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity. Such pitfalls are non-obvious and have not been heretofore sufficiently predictable a priori for any drug class.

Deuterated Thiophene Derivatives

Sitaxsentan is a substituted thiophene-based endothelin receptor antagonist. The carbon-hydrogen bonds of sitaxsentan contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Kinetic Isotope Effect (KIE) that could affect the pharmacokinetic, pharmacologic and/or toxicologic profiles of such endothelin receptor modulators in comparison with the compound having naturally occurring levels of deuterium.

Sitaxsentan is likely metabolized at the methylene group of its methylenedioxy moiety (the $CH_2$ group on the $-O-CH_2-O-$ moiety). This metabolite may be further biotransformed to a potentially reactive electrophilic metabolite(s). These reactive metabolite(s) may be responsible for the hepatotoxicity seen with sitaxsentan administration. Limiting the production of such metabolites has the potential to decrease the danger of the administration of such drugs and may even allow increased dosage and concomitant increased efficacy. Sitaxsentan is also known to be a substrate and inhibitor of the polymorphically-expressed CYP2C9. This may account, in part, for the observed nonlinearity of the dose-response for sitaxsentan. Various deuteration patterns can be used to a) reduce or eliminate unwanted metabolites, b) increase the half-life of the drug, c) decrease the number of doses needed to achieve a desired effect, d) decrease the amount of a dose needed to achieve a desired effect, e) increase the formation of active metabolites, if any are formed, and/or f) decrease the production of deleterious metabolites in specific tissues and/or create a more effective drug and/or a safer drug for polypharmacy, whether the polypharmacy be intentional or not. The deuteration approach has strong potential to slow the metabolism via various oxidative mechanisms and attenuate interpatient variatability.

In one embodiment, disclosed herein is a compound having structural Formula I

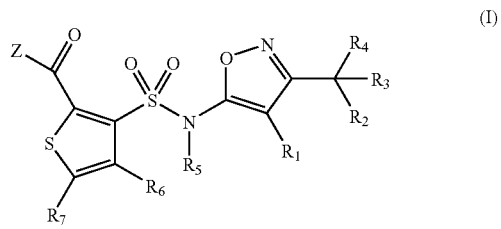

(I)

or a pharmaceutically acceptable salt, solvate, or prodrug thereof;

wherein:

$R_1$ is selected from the group consisting of chloride, and

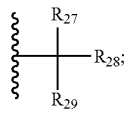

Z is selected from the group consisting of

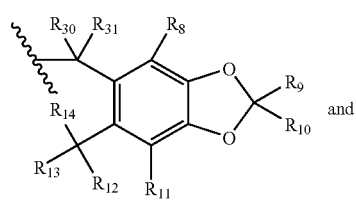

and

-continued

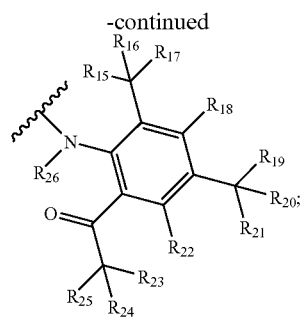

$R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are independently selected from the group consisting of hydrogen and deuterium; and at least one of $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ is deuterium.

In a further embodiment, said compound is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, substantially an individual diastereomer, or a mixture of about 90% or more by weight of an individual diastereomer and about 10% or less by weight of any other diastereomer.

In another embodiment, at least one of $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ independently has deuterium enrichment of no less than about 1%, no less than about 5%, no less than about 10%, no less than about 20%, no less than about 50%, no less than about 70%, no less than about 80%, no less than about 90%, or no less than about 98%.

In certain embodiments, $R_2$ is hydrogen. In yet other embodiments, $R_3$ is hydrogen. In some embodiments, $R_4$ is hydrogen. In other embodiments, $R_5$ is hydrogen. In yet other embodiments, $R_6$ is hydrogen. In still other embodiments, $R_7$ is hydrogen. In still other embodiments, $R_8$ is hydrogen. In some embodiments, $R_9$ is hydrogen. In other embodiments, $R_{10}$ is hydrogen. In yet other embodiments, $R_{11}$ is hydrogen. In still other embodiments, $R_{12}$ is hydrogen. In yet other embodiments, $R_{13}$ is hydrogen. In other embodiments, $R_{14}$ is hydrogen. In certain embodiments, $R_{15}$ is hydrogen. In other embodiments, $R_{16}$ is hydrogen. In yet other embodiments, $R_{17}$ is hydrogen. In some embodiments, $R_{18}$ is hydrogen. In other embodiments, $R_{19}$ is hydrogen. In yet other embodiments, $R_{20}$ is hydrogen. In still other embodiments, $R_{21}$ is hydrogen. In still other embodiments, $R_{22}$ is hydrogen. In some embodiments, $R_{23}$ is hydrogen. In other embodiments, $R_{24}$ is hydrogen. In yet other embodiments, $R_{25}$ is hydrogen. In still other embodiments, $R_{26}$ is hydrogen. In yet other embodiments, $R_{27}$ is hydrogen. In other embodiments, $R_{28}$ is hydrogen. In some embodiments, $R_{29}$ is hydrogen. In some embodiments, $R_{30}$ is hydrogen. In some embodiments, $R_{31}$ is hydrogen.

In certain embodiments, $R_2$ is deuterium. In yet other embodiments, $R_3$ is deuterium. In some embodiments, $R_4$ is deuterium. In other embodiments, $R_5$ is deuterium. In yet other embodiments, $R_6$ is deuterium. In still other embodiments, $R_7$ is deuterium. In still other embodiments, $R_8$ is deuterium. In some embodiments, $R_9$ is deuterium. In other embodiments, $R_{10}$ is deuterium. In yet other embodiments, $R_{11}$ is deuterium. In still other embodiments, $R_{12}$ is deuterium. In yet other embodiments, $R_{13}$ is deuterium. In other embodiments, $R_{14}$ is deuterium. In certain embodiments, $R_{15}$ is deuterium. In other embodiments, $R_{16}$ is deuterium. In yet other embodiments, $R_{17}$ is deuterium. In some embodiments, $R_{18}$ is deuterium. In other embodiments, $R_{19}$ is deuterium. In yet other embodiments, $R_{20}$ is deuterium. In still other embodiments, $R_{21}$ is deuterium. In still other embodiments, $R_{22}$ is deuterium. In some embodiments, $R_{23}$ is deuterium. In other embodiments, $R_{24}$ is deuterium. In yet other embodiments, $R_{25}$ is deuterium. In still other embodiments, $R_{26}$ is deuterium. In yet other embodiments, $R_{27}$ is deuterium. In other embodiments, $R_{28}$ is deuterium. In some embodiments, $R_{29}$ is deuterium. In some embodiments, $R_{30}$ is deuterium. In some embodiments, $R_{31}$ is deuterium.

In yet another embodiment, at least one of $R_9$, and $R_{10}$ is deuterium.

In yet another embodiment, $R_9$, and $R_{10}$ are deuterium.

In yet another embodiment, at least one of $R_9$, and $R_{10}$ is deuterium; and $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, $R_9$, and $R_{10}$ are deuterium; and $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, $R_1$ is chloride; and at least one of $R_9$, and $R_{10}$ is deuterium.

In yet another embodiment, $R_1$ is chloride; and $R_9$, and $R_{10}$ are deuterium.

In yet another embodiment, $R_1$ is chloride; and at least one of $R_9$, and $R_{10}$ is deuterium; and $R_2$, $R_3$, $R_4$, $R_5$, $R_6$, $R_7$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, $R_1$ is chloride; and $R_9$, and $R_{10}$ are deuterium; and $R_2$, $R_3$, $R_4$, $R_5$, $R_6$, $R_7$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, $R_1$ is

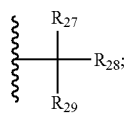

and at least one of $R_9$, and $R_{10}$ is deuterium.

In yet another embodiment, $R_1$ is

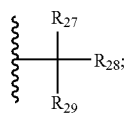

and $R_9$, and $R_{10}$ are deuterium.

In yet another embodiment, $R_1$ is

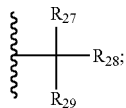

at least one of $R_9$, and $R_{10}$ is deuterium; and $R_2$, $R_3$, $R_4$, $R_5$, $R_6$, $R_7$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, $R_1$ is

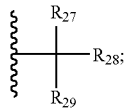

$R_9$, and $R_{10}$ are deuterium; and $R_2$, $R_3$, $R_4$, $R_5$, $R_6$, $R_7$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, Z is

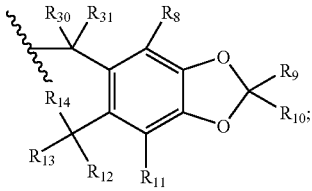

and at least one of $R_9$, and $R_{10}$ is deuterium.

In yet another embodiment, Z is

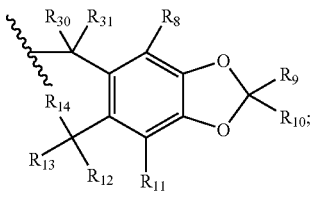

and $R_9$, and $R_{10}$ are deuterium.

In yet another embodiment, Z is

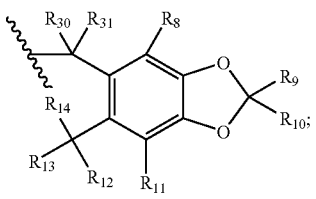

and at least one of $R_9$, and $R_{10}$ is deuterium; and $R_2$, $R_3$, $R_4$, $R_5$, $R_6$, $R_7$, $R_8$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, Z is

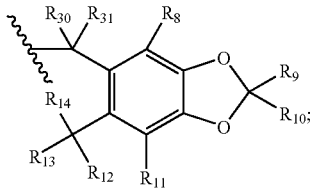

and $R_9$, and $R_{10}$ are deuterium; and $R_2$, $R_3$, $R_4$, $R_5$, $R_6$, $R_7$, $R_9$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, and $R_{31}$ are hydrogen.

In yet another embodiment, $R_5$ or $R_{26}$ is deuterium.

In yet another embodiment, $R_5$ and $R_{26}$ are deuterium.

In yet another embodiment, $R_1$ is chloride; $R_5$ and $R_{26}$ are deuterium; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_1$ is chloride; $R_5$ and $R_{26}$ are deuterium; and $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_1$ is

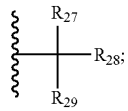

$R_5$ and $R_{26}$ are deuterium; and at least one of $R_2$, $R_3$, $R_4$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_1$ is

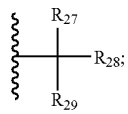

$R_5$ and $R_{26}$ are deuterium; and $R_2$, $R_3$, $R_4$, $R_6$, $R_7$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

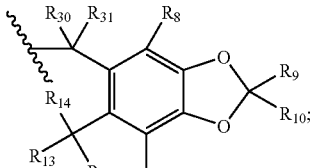

$R_5$ and $R_{26}$ are deuterium; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

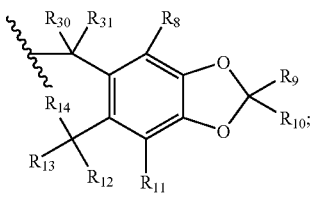

$R_5$ and $R_{26}$ are deuterium; and $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

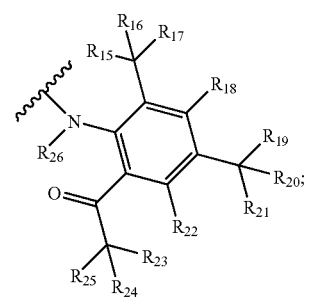

$R_5$ and $R_{26}$ are deuterium; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

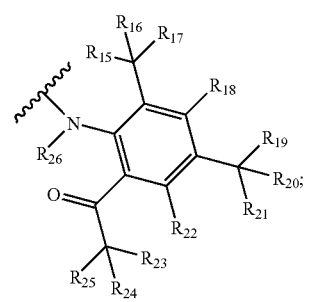

$R_5$ and $R_{26}$ are deuterium; and
$R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_5$ or $R_{26}$ is hydrogen.

In yet another embodiment, $R_5$ and $R_{26}$ are hydrogen.

In yet another embodiment, $R_1$ is chloride; $R_5$ and $R_{26}$ are hydrogen; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_1$ is chloride; $R_5$ and $R_{26}$ are hydrogen; and $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_1$ is

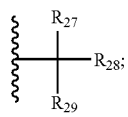

$R_5$ and $R_{26}$ are hydrogen; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, $R_1$ is

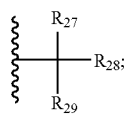

$R_5$ and $R_{26}$ are hydrogen; and $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

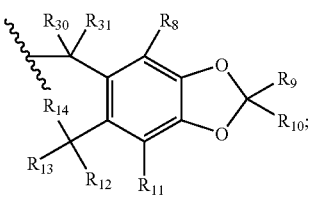

$R_5$ and $R_{26}$ are hydrogen; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

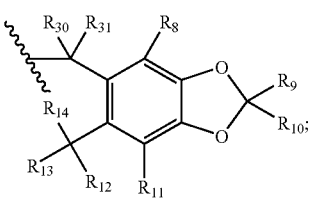

$R_5$ and $R_{26}$ are hydrogen; and $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

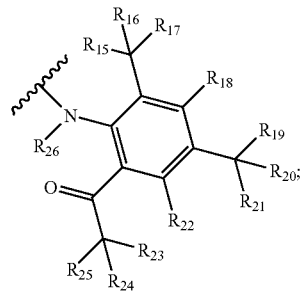

$R_5$ and $R_{26}$ are hydrogen; and at least one of $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In yet another embodiment, Z is

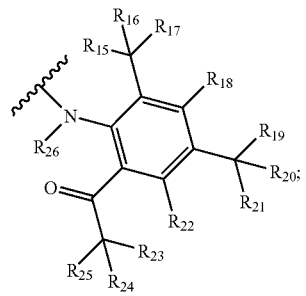

$R_5$ and $R_{26}$ are hydrogen; and $R_2$, $R_3$, $R_4$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{27}$, $R_{28}$, $R_{29}$, $R_{30}$, and $R_{31}$ is independently deuterium.

In certain embodiments, $R_1$ is chloride.

In certain embodiments, $R_1$ is

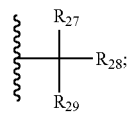

In certain embodiments, Z is

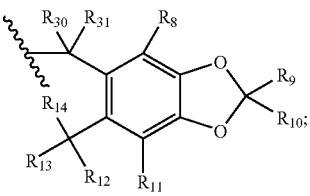

In certain embodiments, Z is

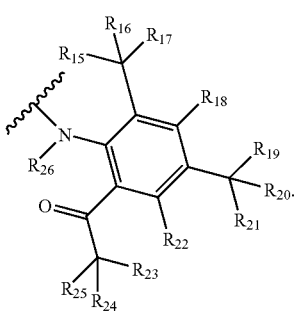

In yet another embodiment, the compound as disclosed herein is selected from the group consisting of:

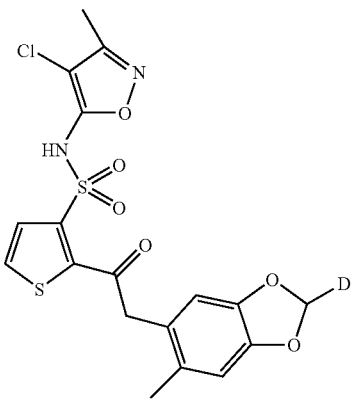

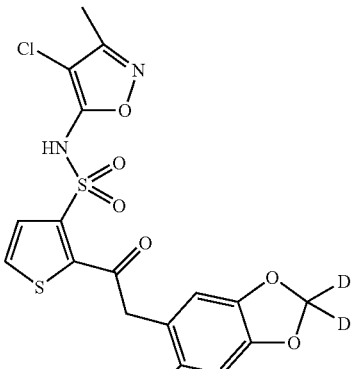

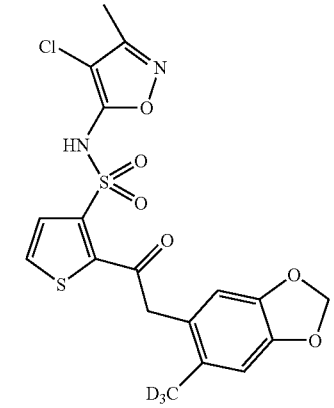

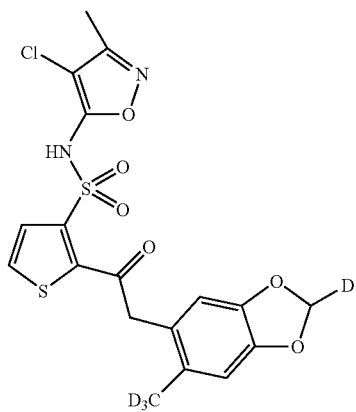
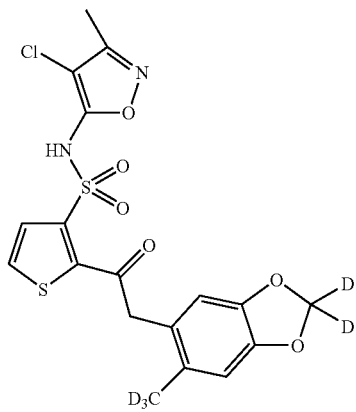
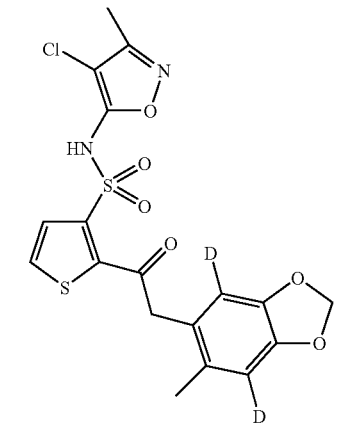
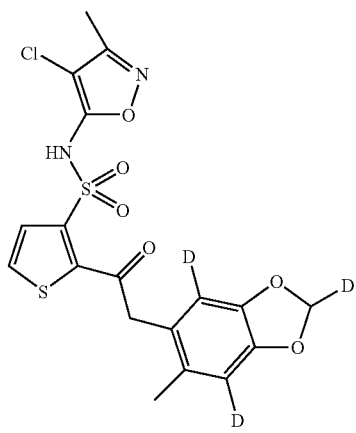
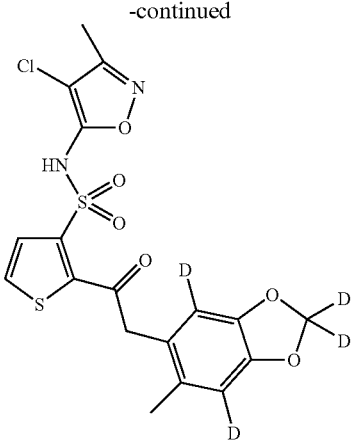
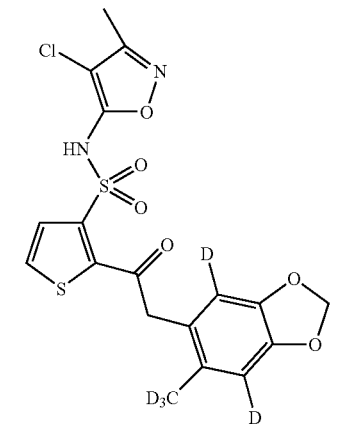
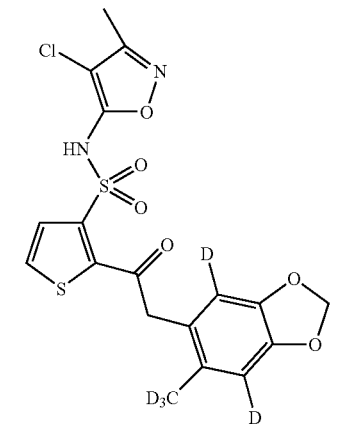
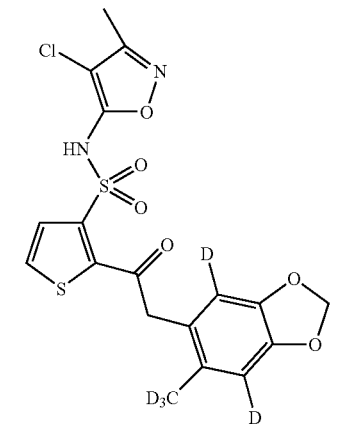

-continued
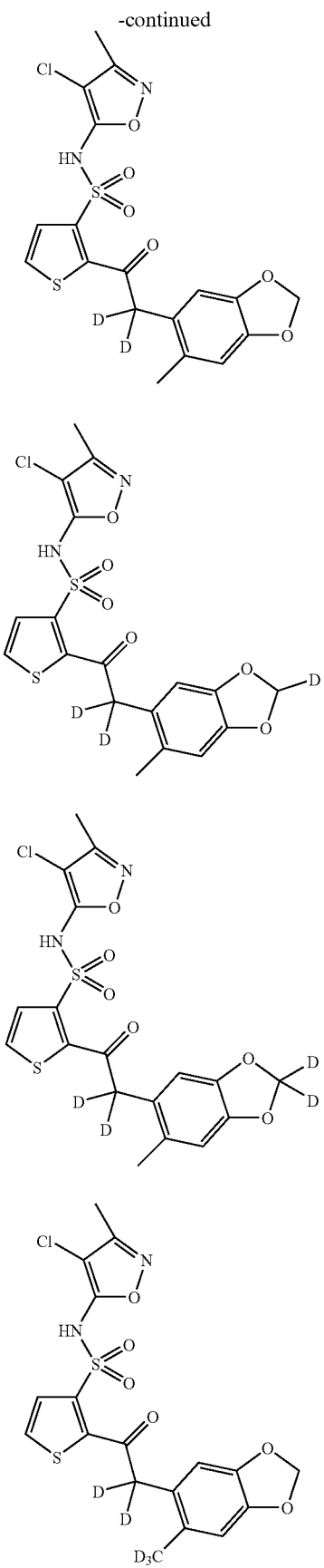
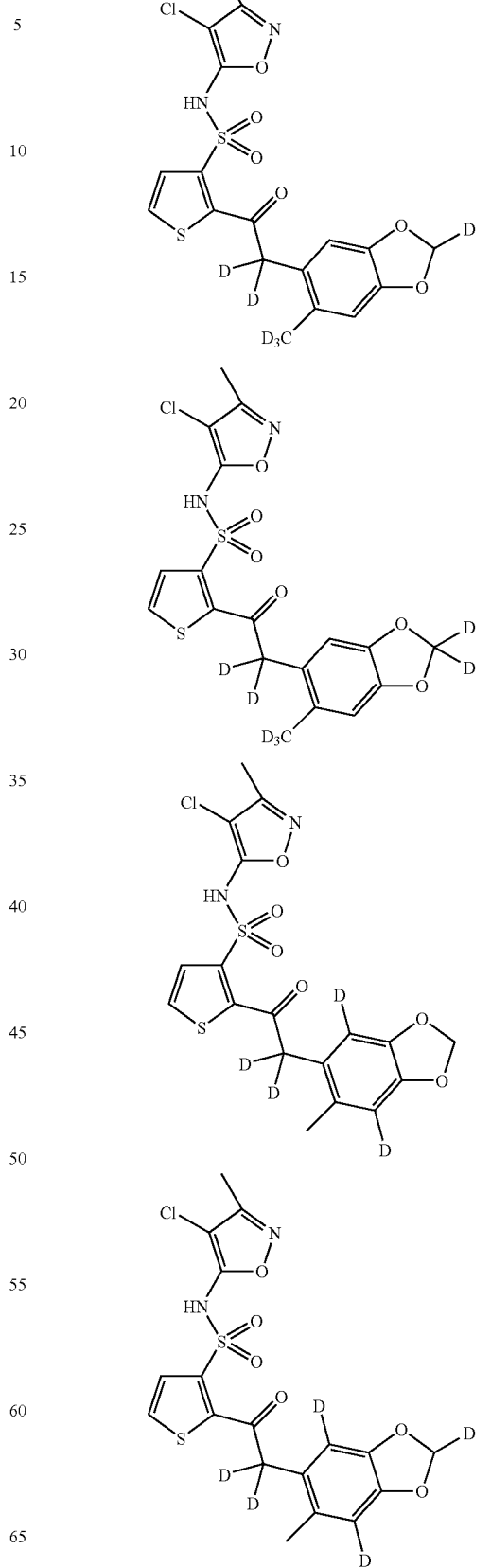

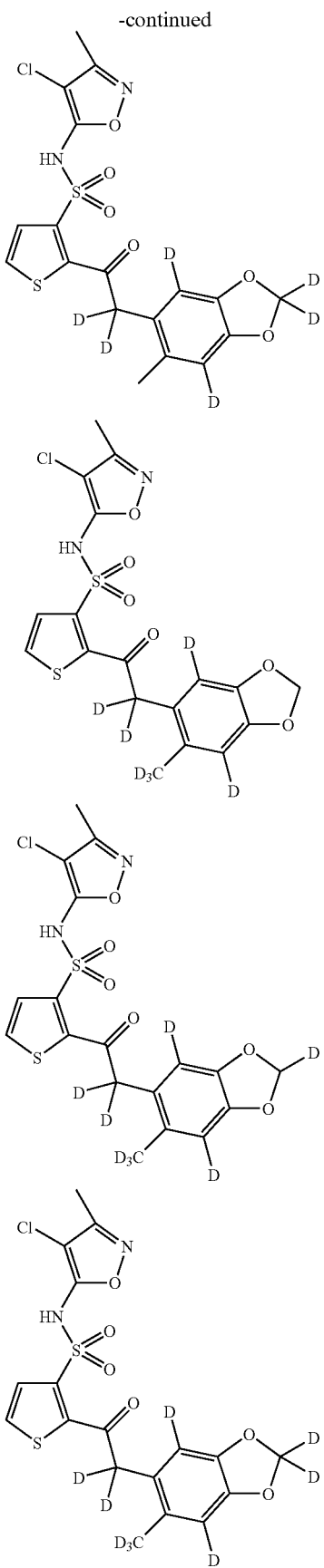
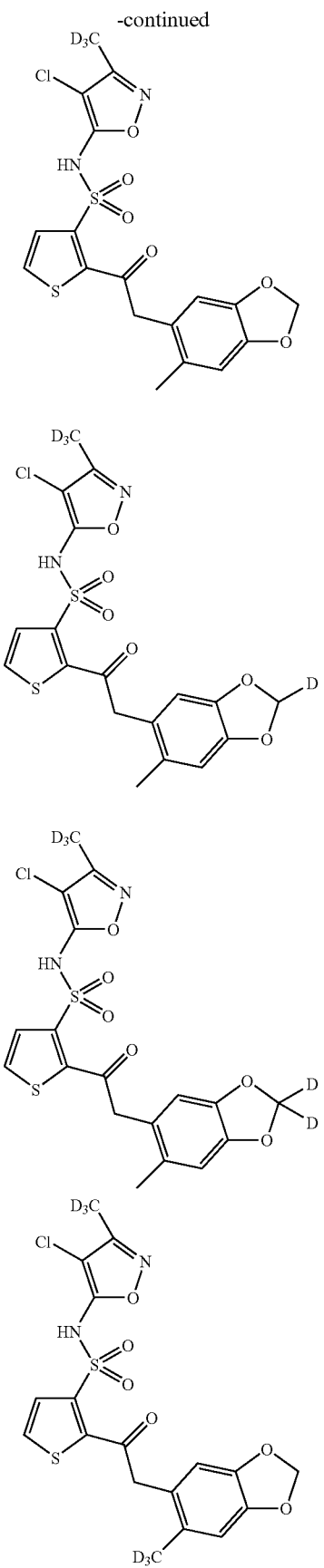

-continued
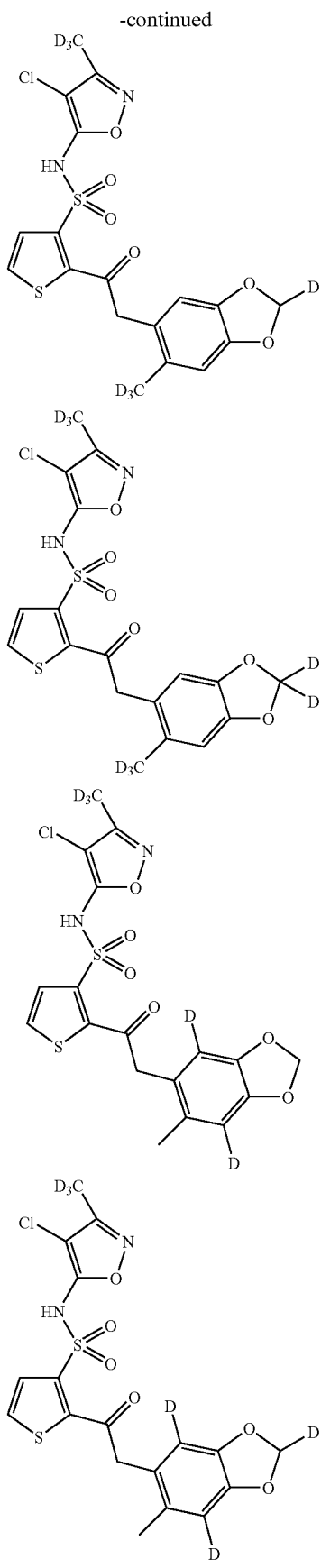
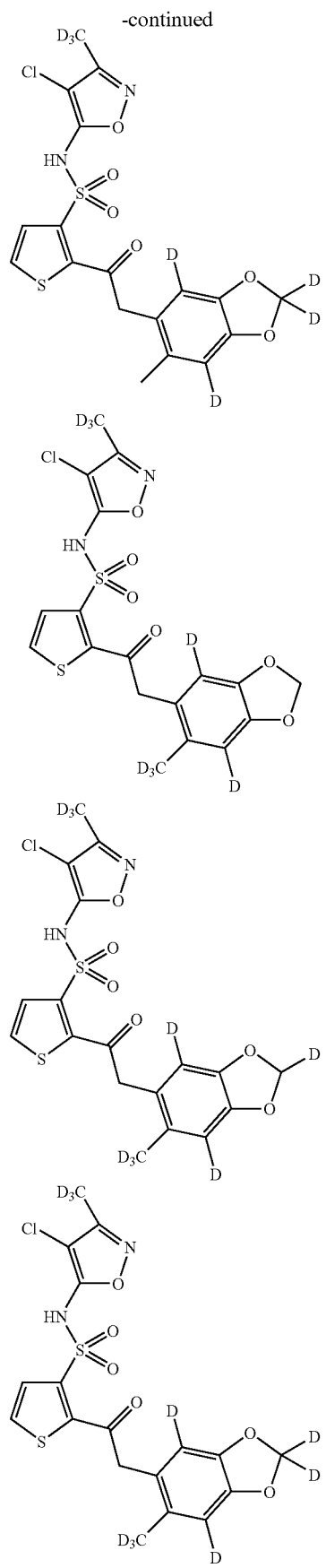

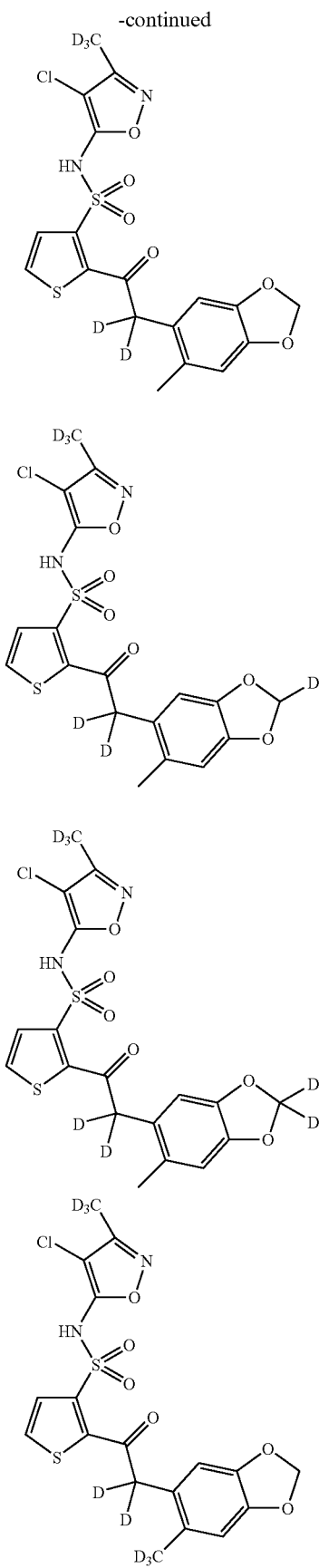
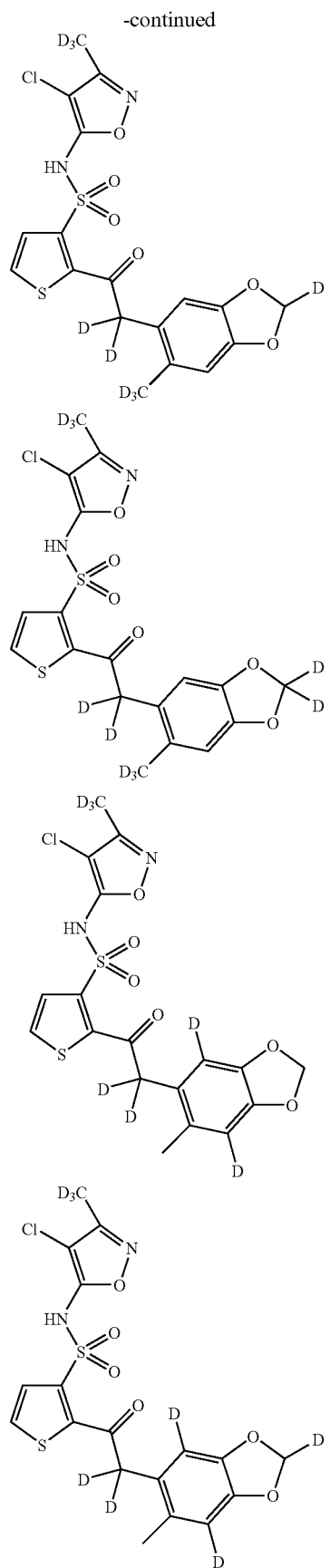

33
-continued
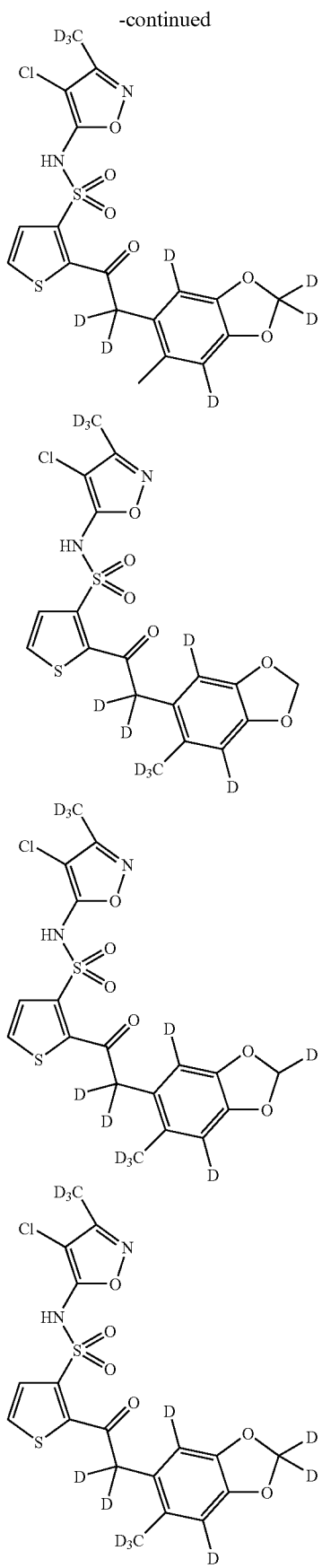
34
-continued
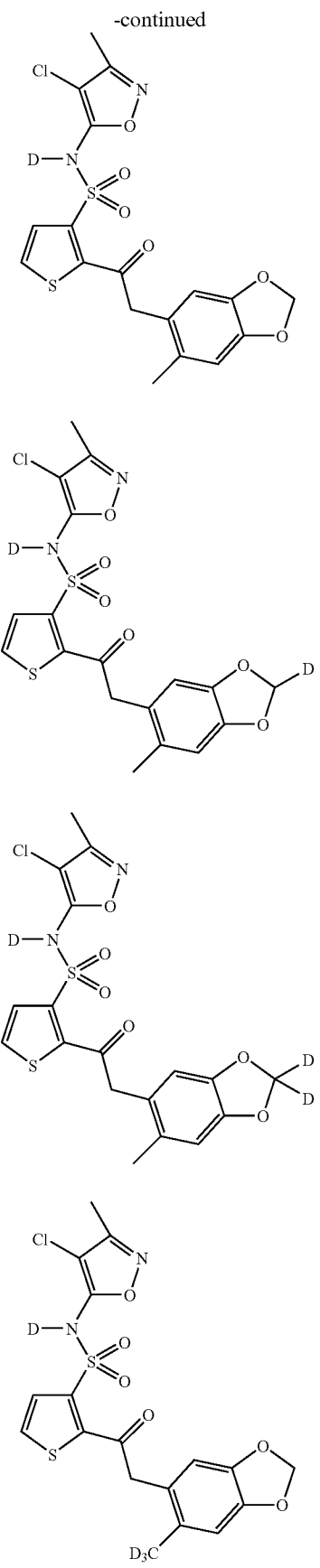

-continued
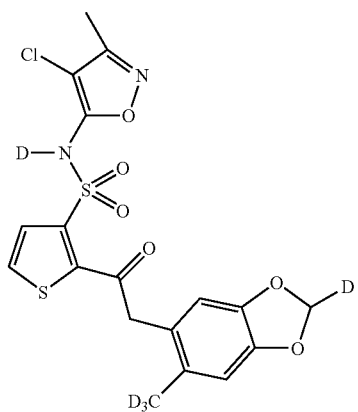
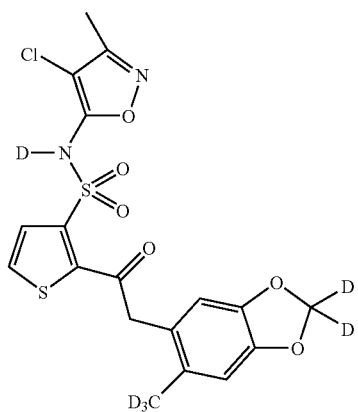
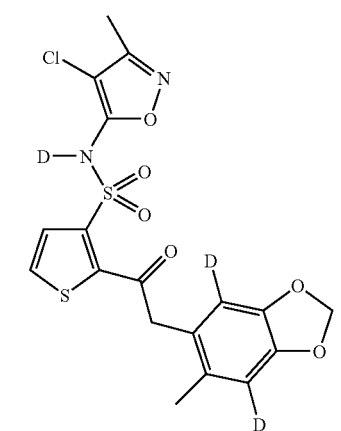
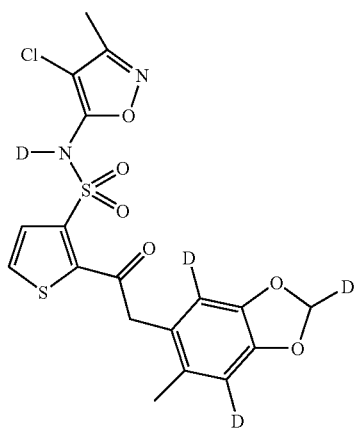
-continued
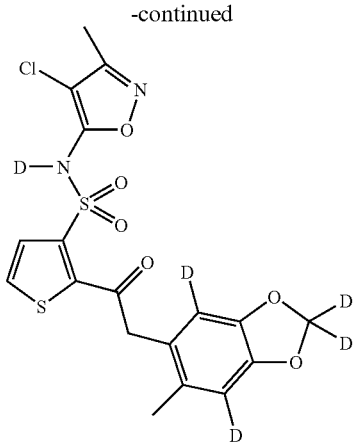
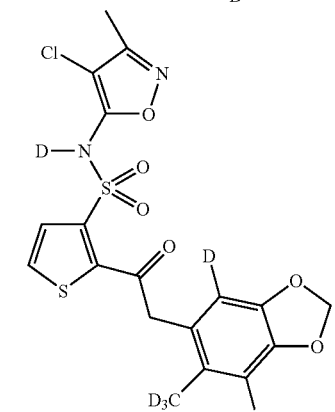
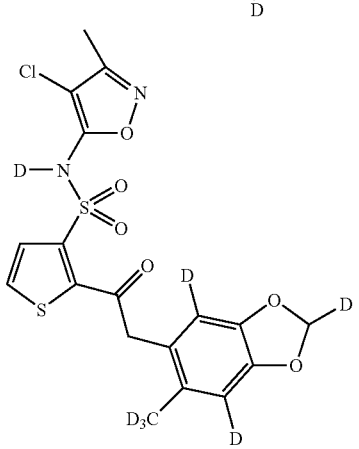
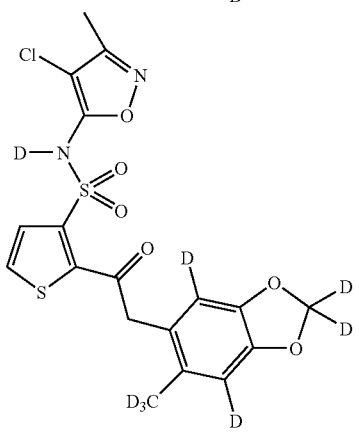

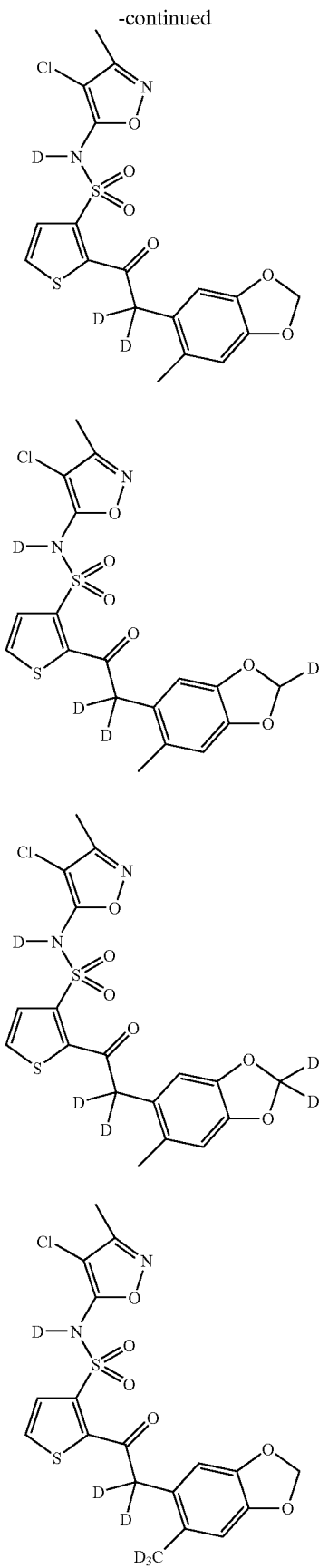

-continued
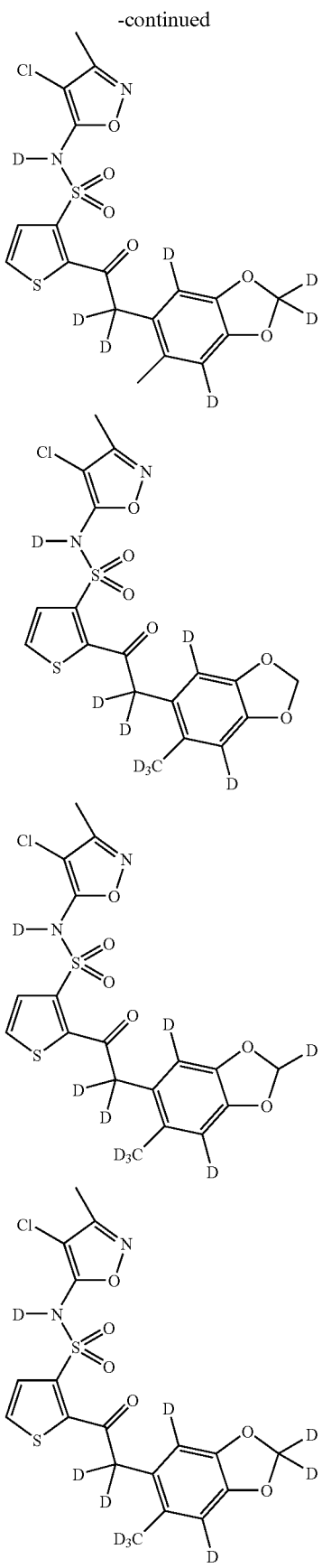
-continued
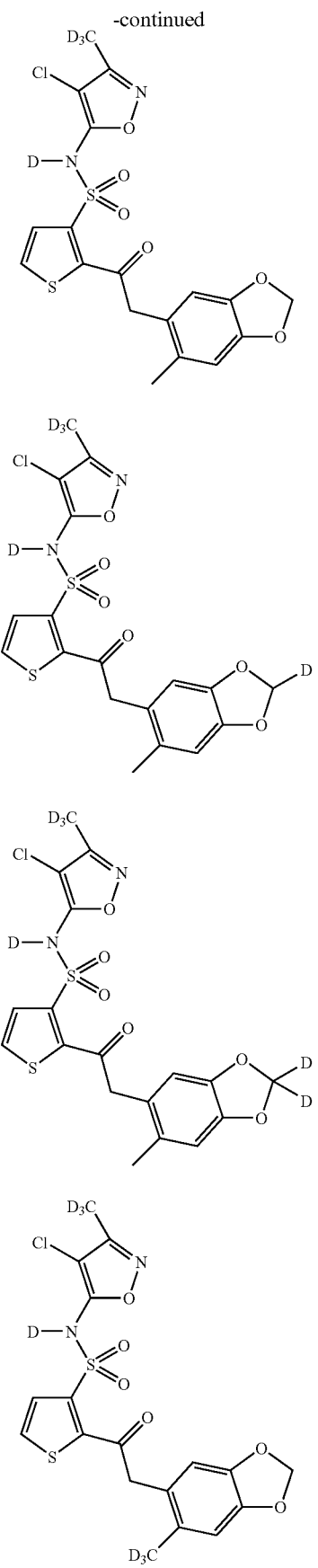

-continued
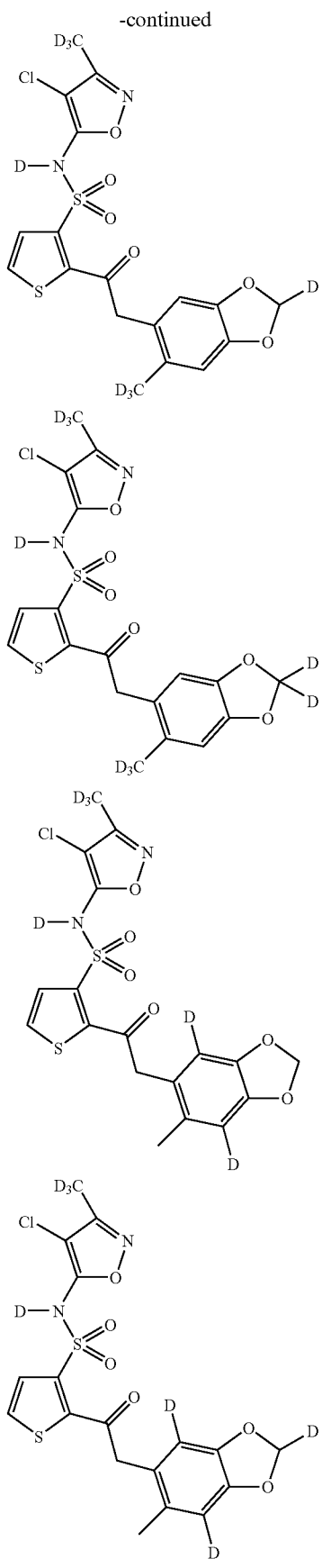
-continued
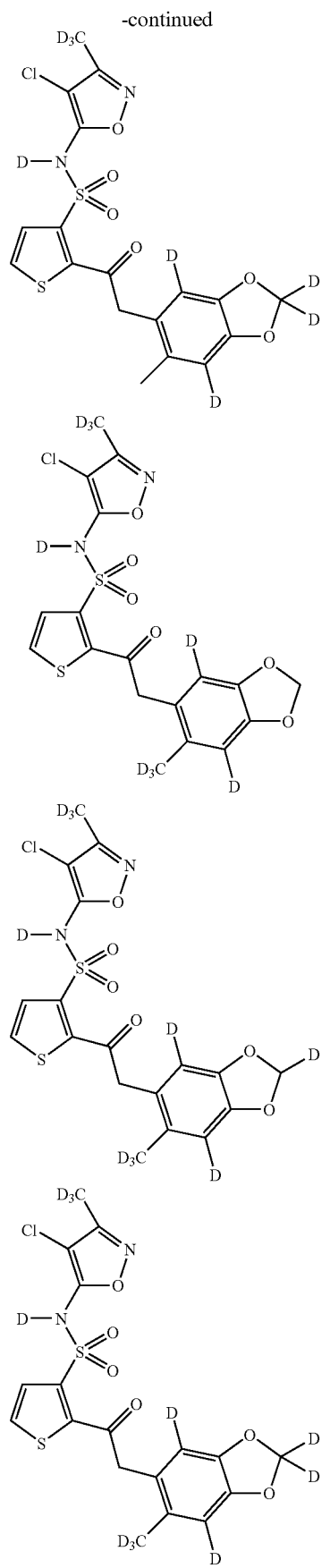

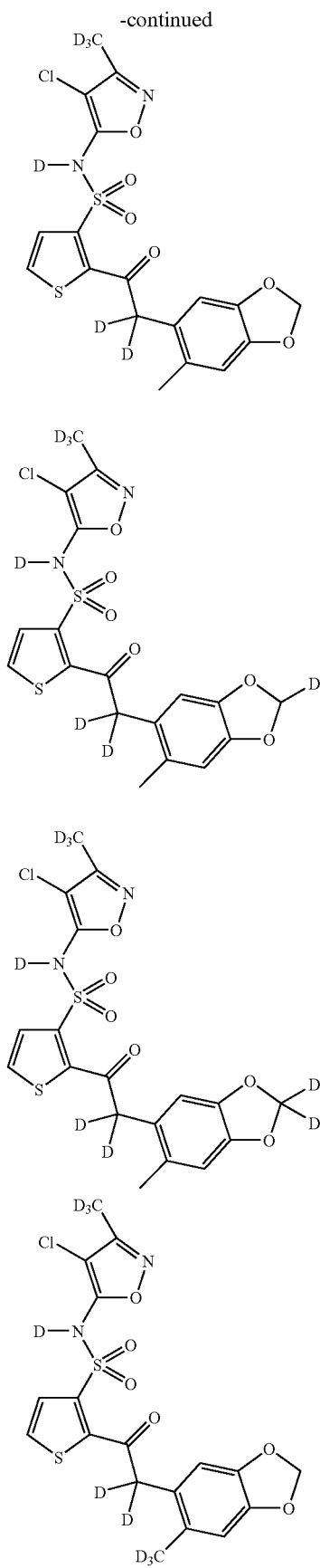

-continued
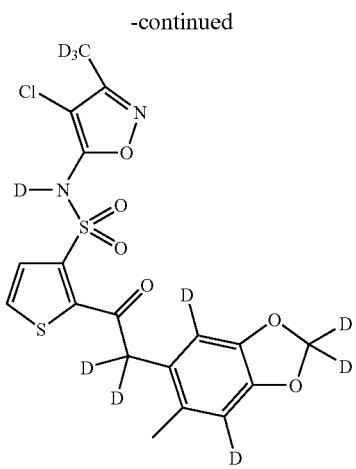
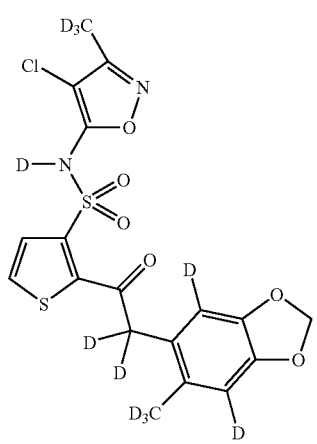
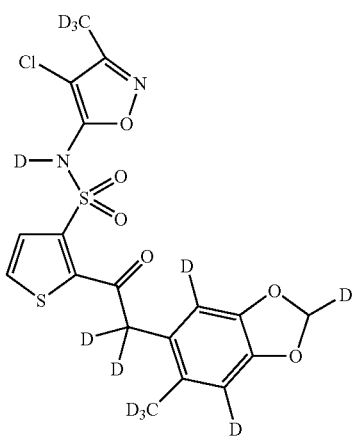
-continued
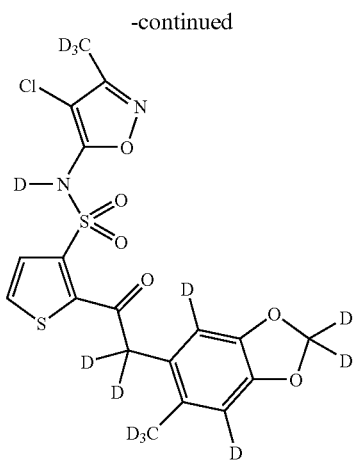
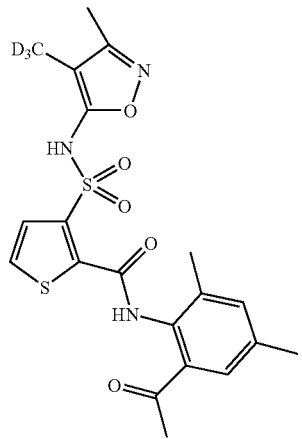
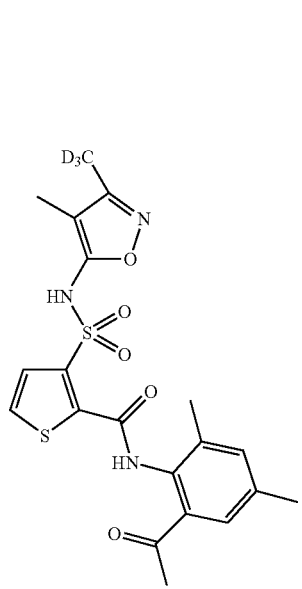

-continued
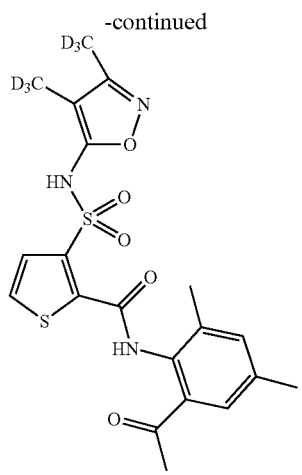
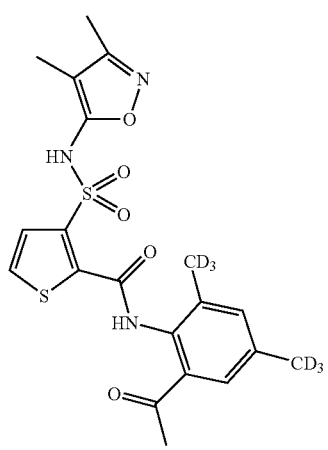
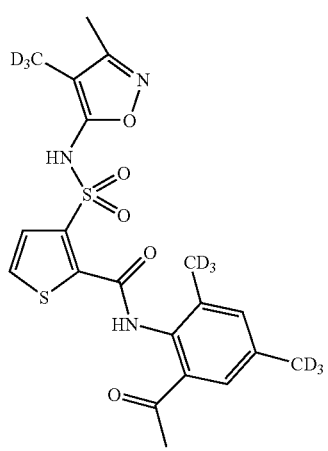
-continued
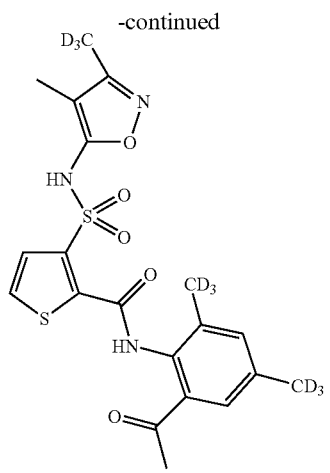
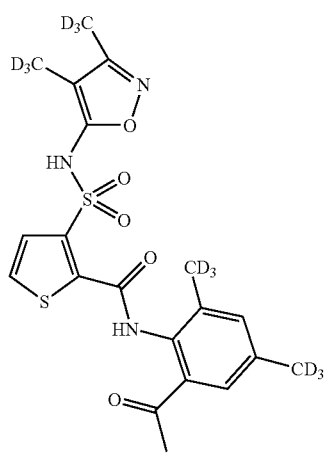
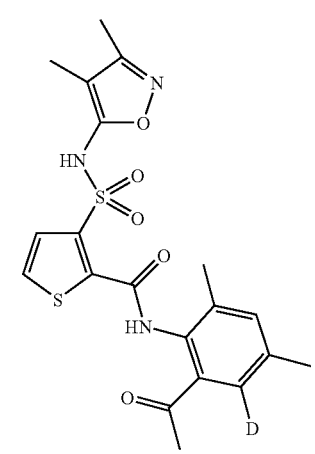

-continued
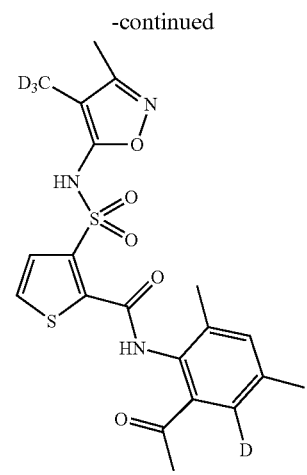
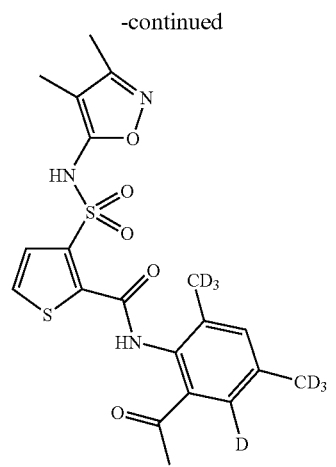
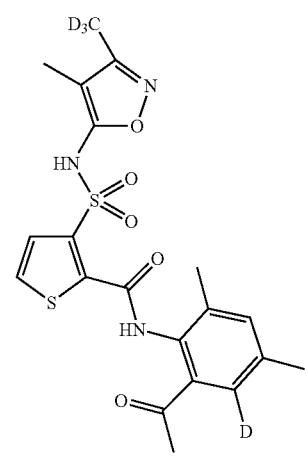
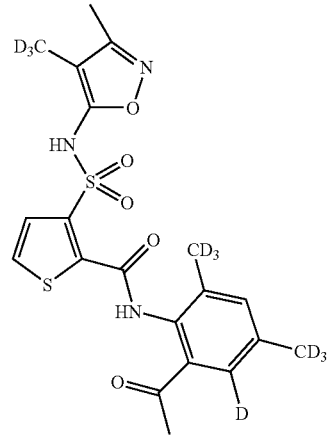
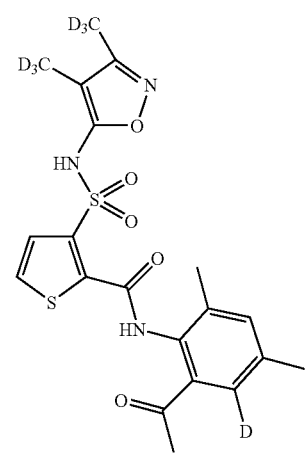
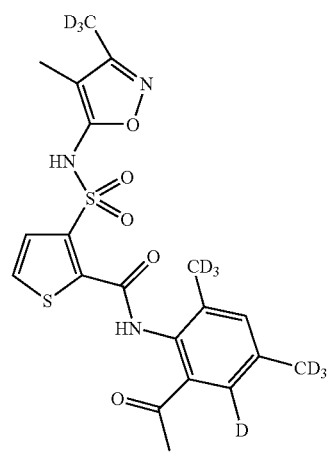

51
-continued
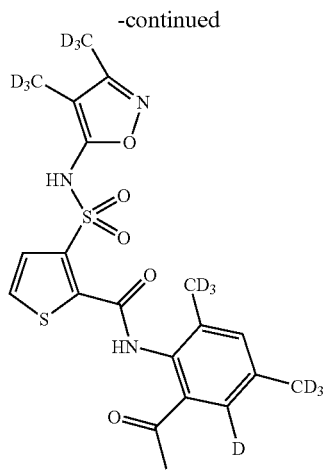
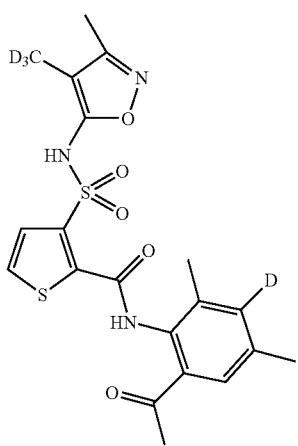
52
-continued
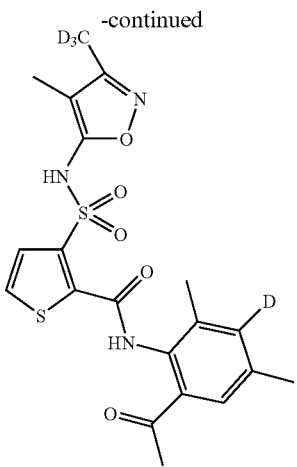
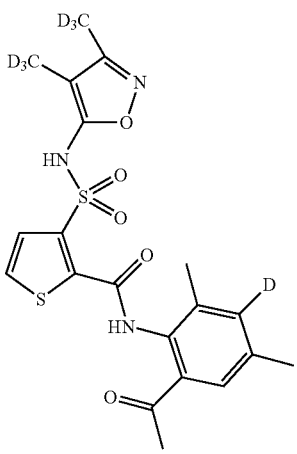
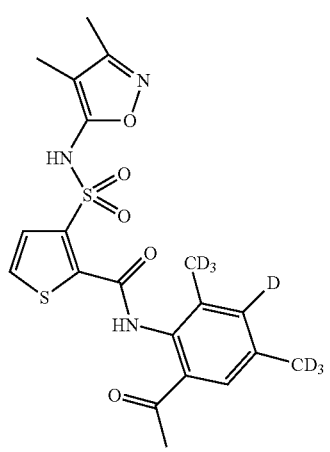

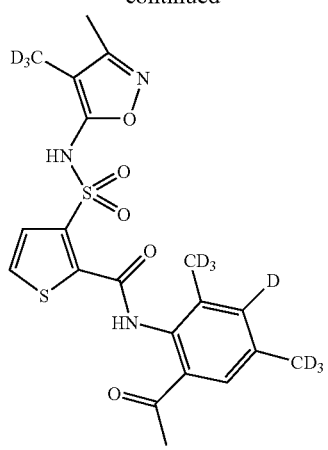
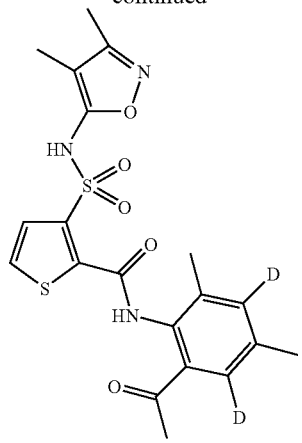
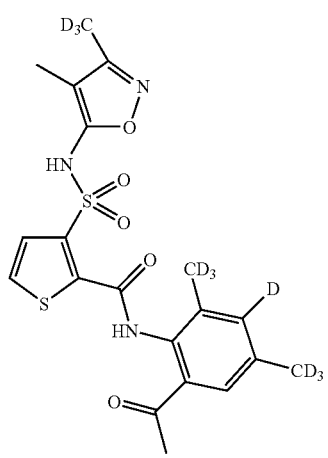
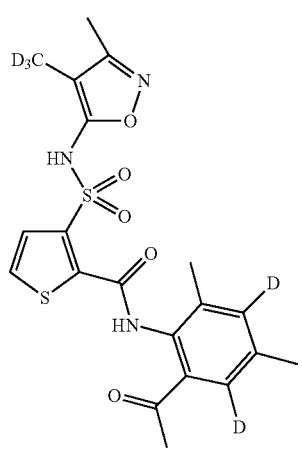
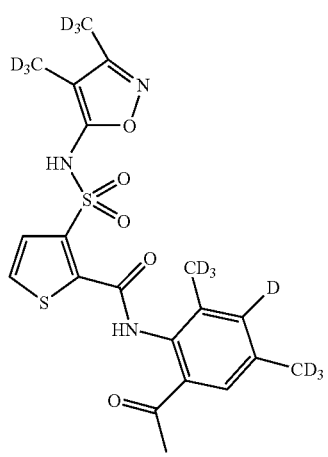
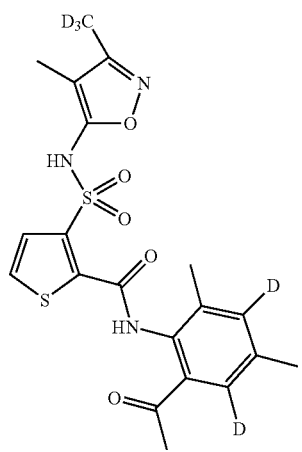

-continued
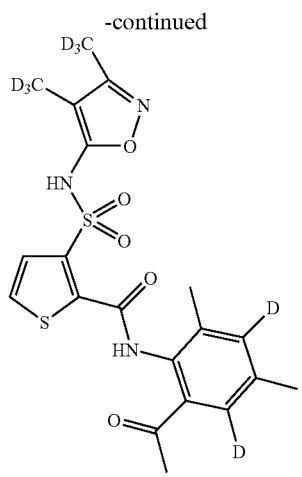
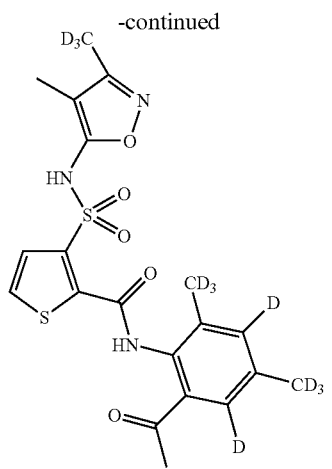
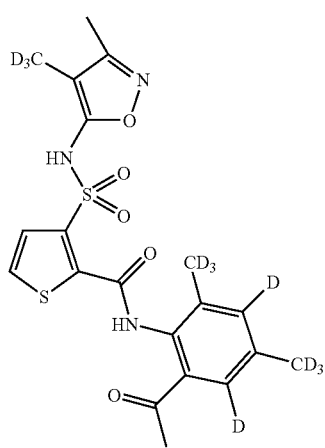
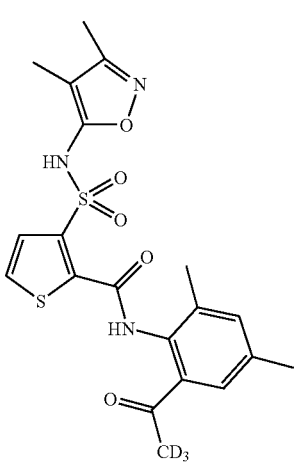

57
-continued
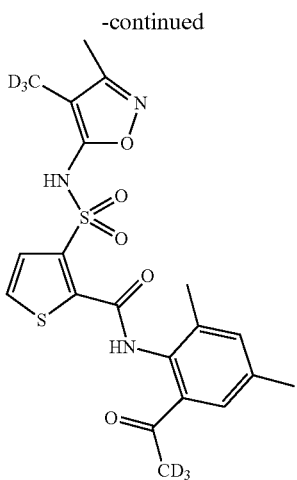
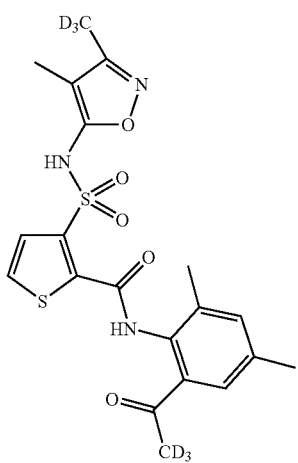
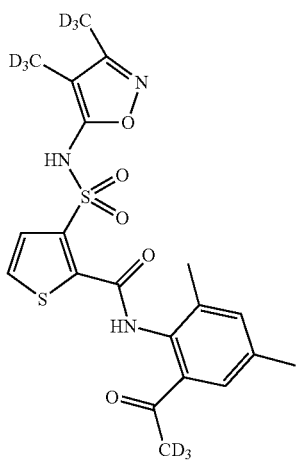
58
-continued
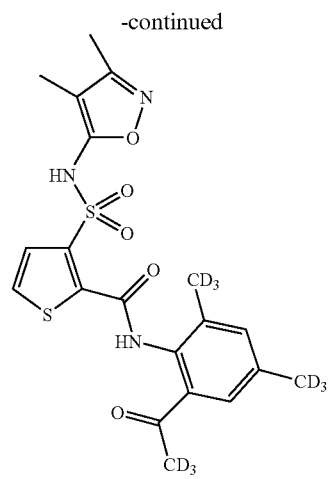
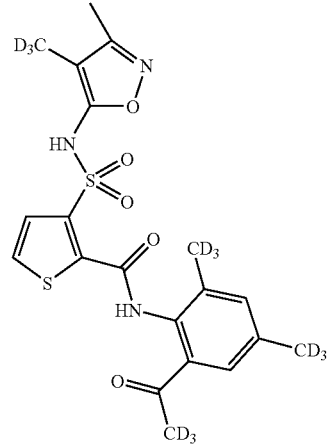
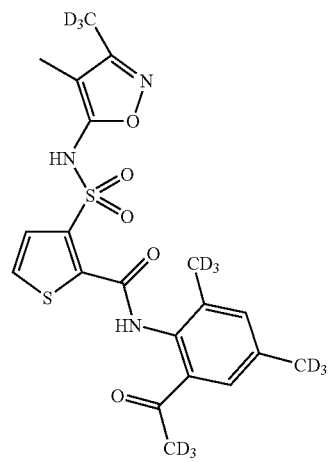

-continued
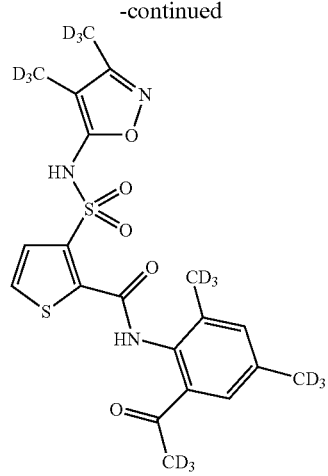
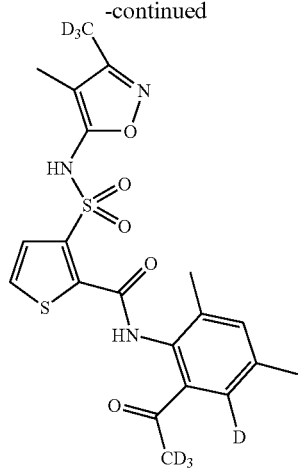
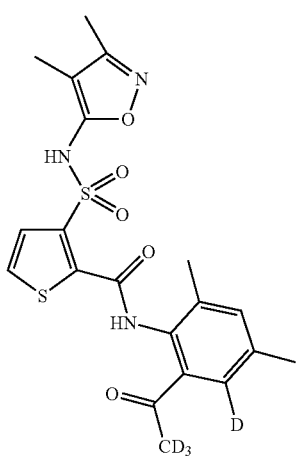
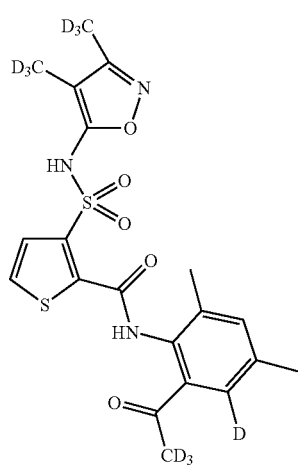
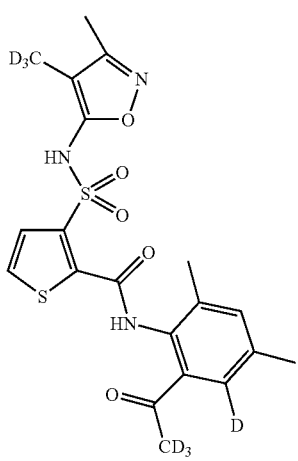
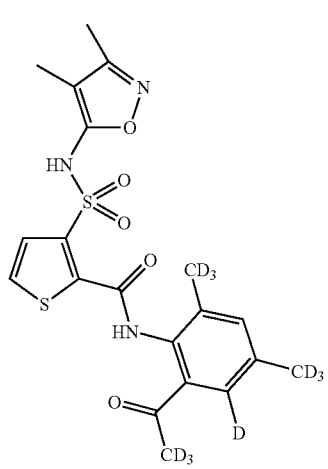

-continued
61
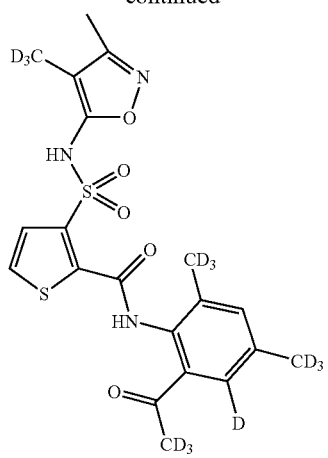
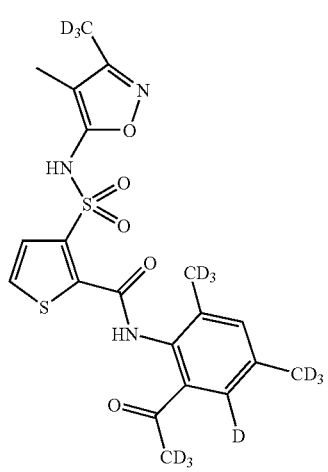
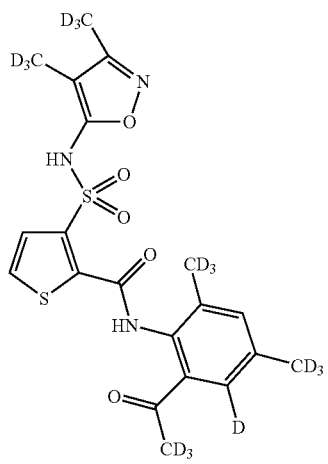
62
-continued
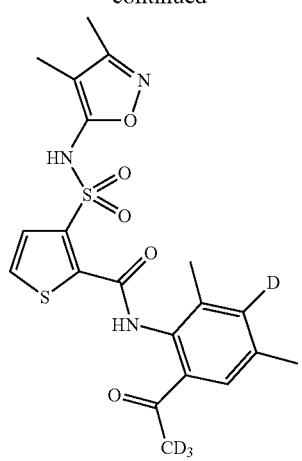
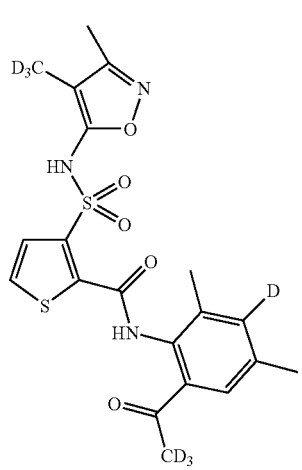

63
-continued
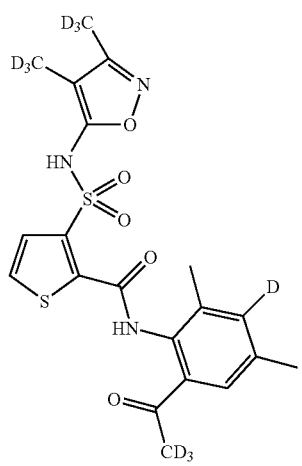
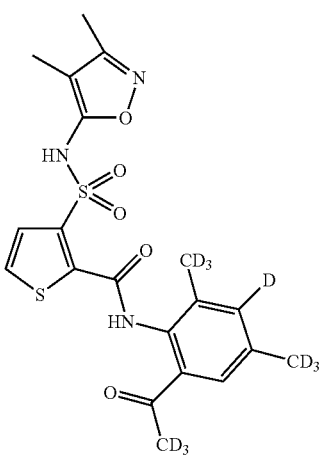
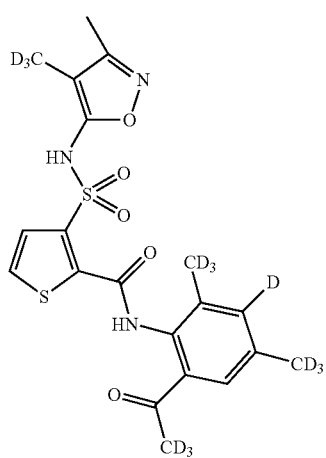
64
-continued
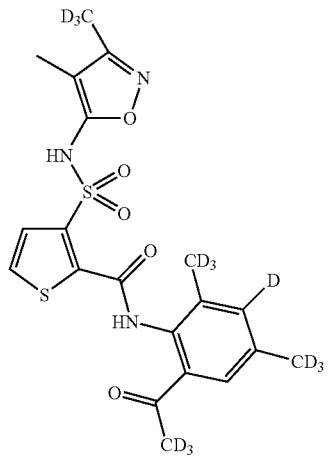
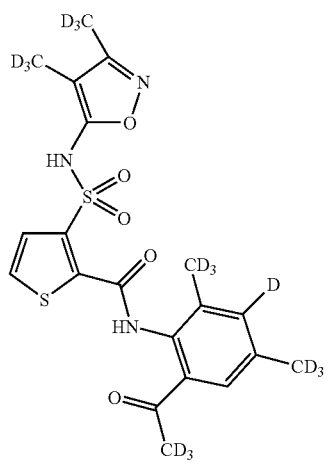

65
-continued
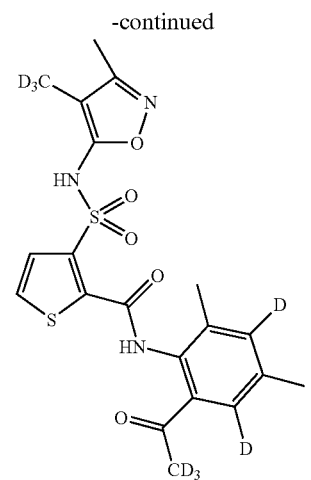
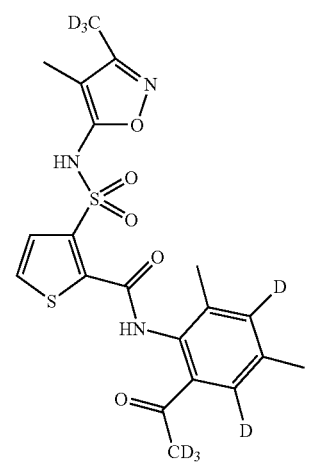
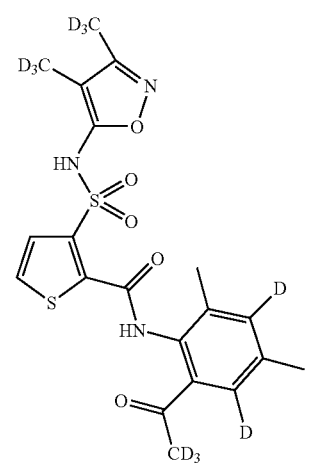
66
-continued
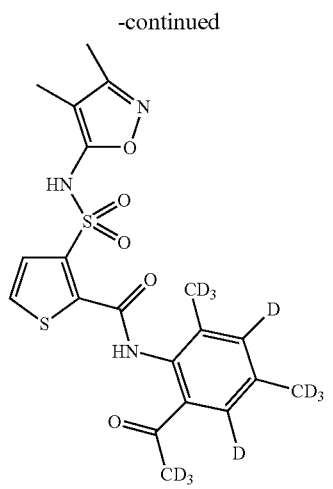
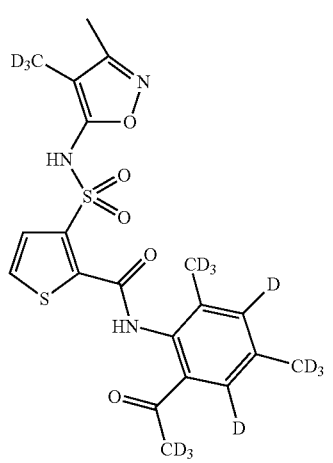
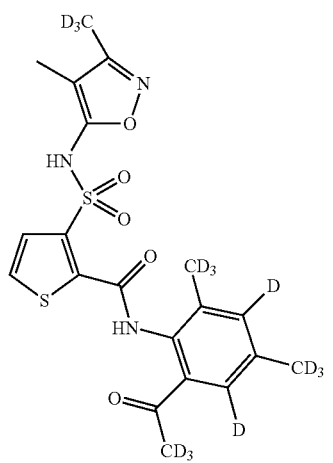

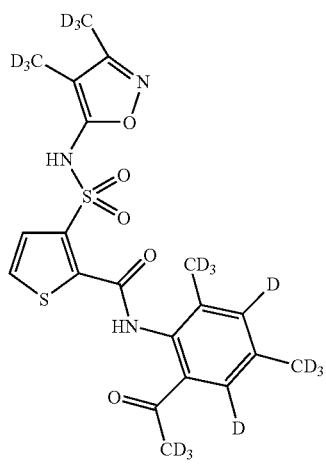
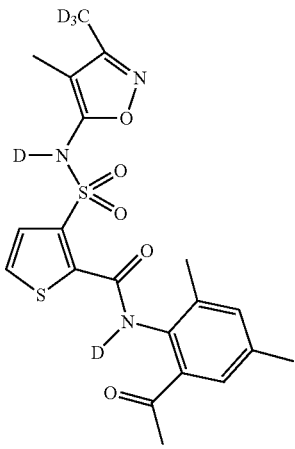
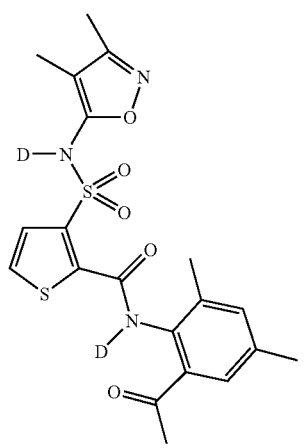
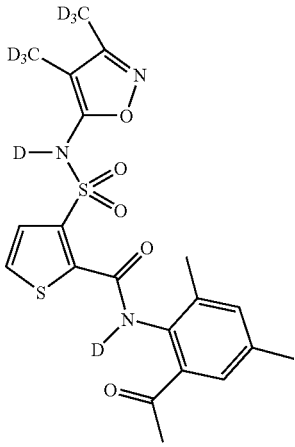
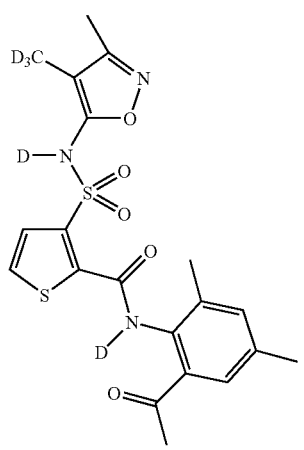
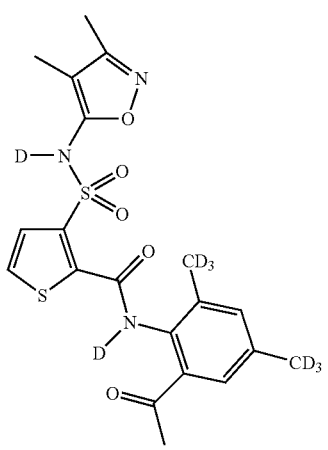

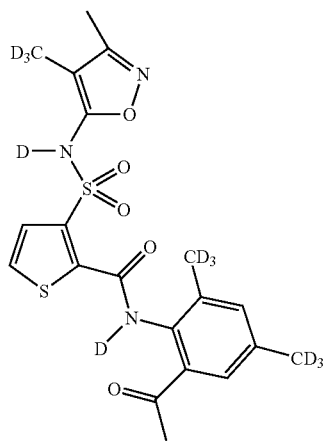
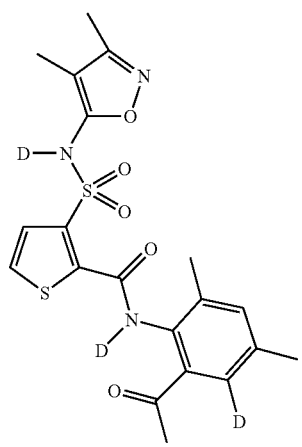
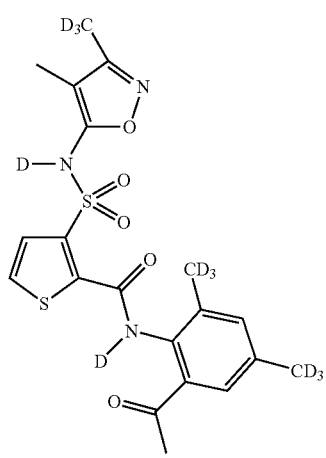
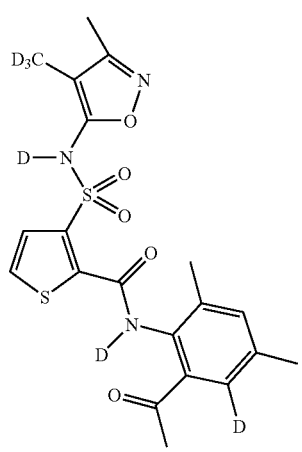
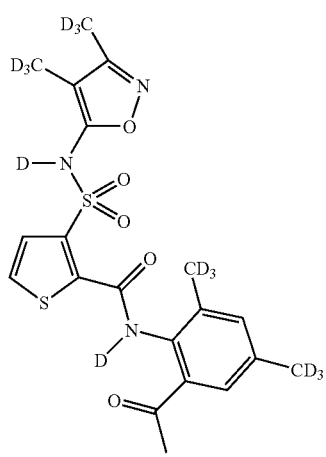
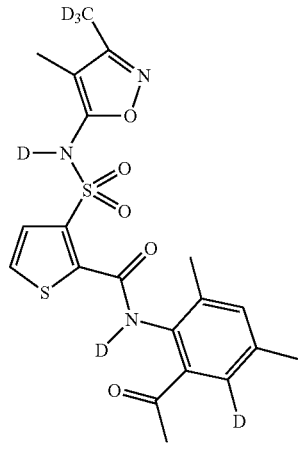

-continued
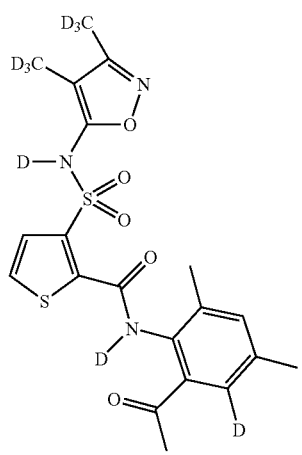
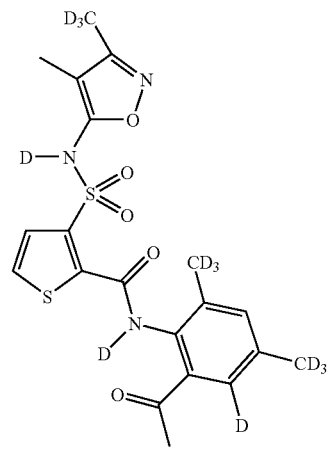
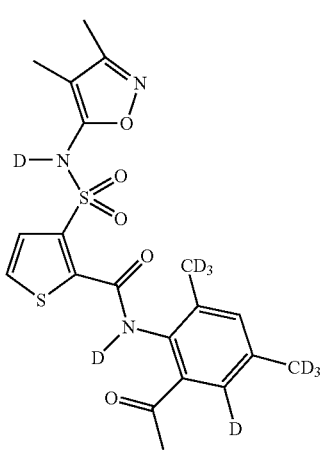
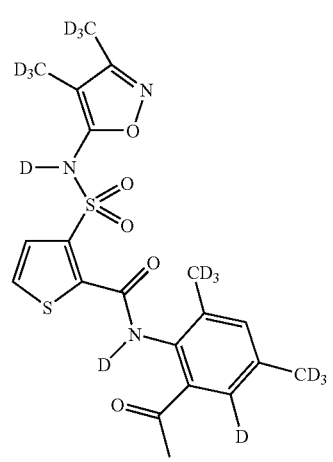
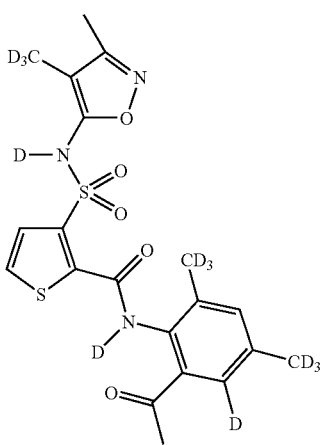
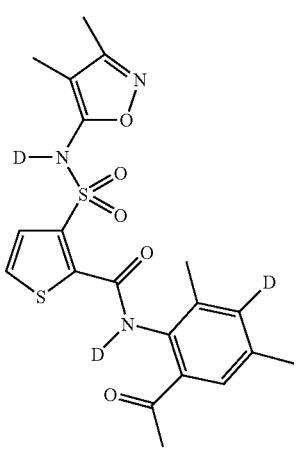

73
-continued
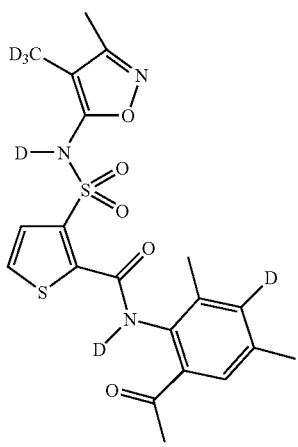
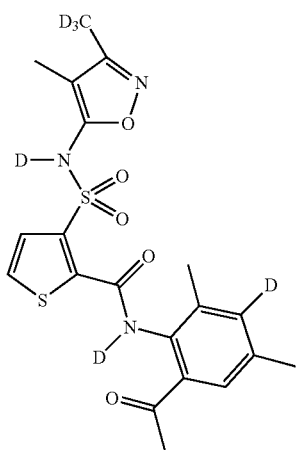
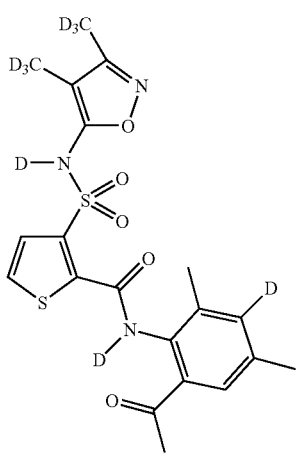
74
-continued
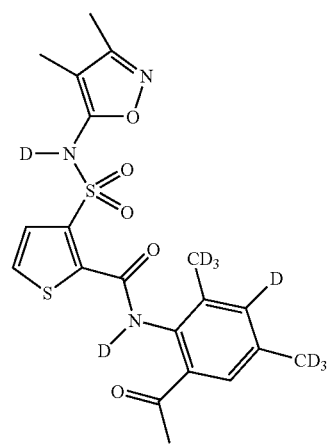
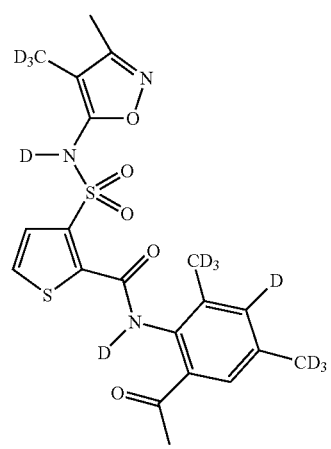
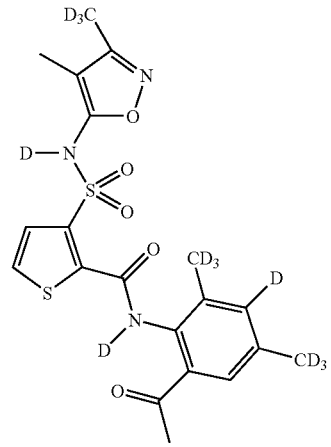

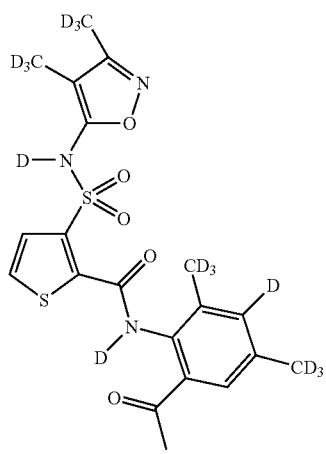
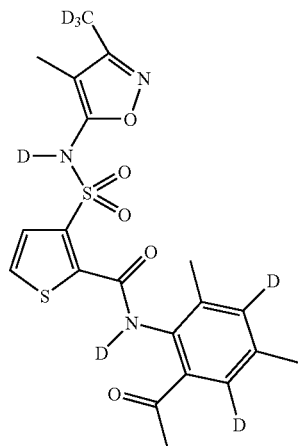
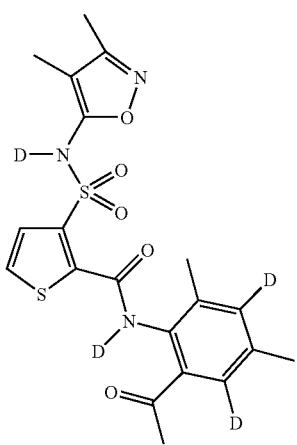
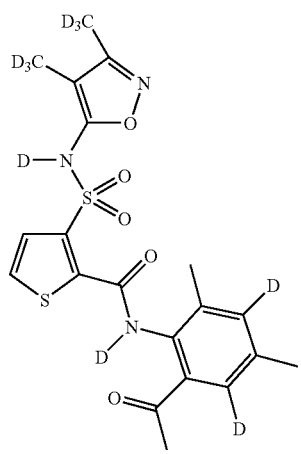
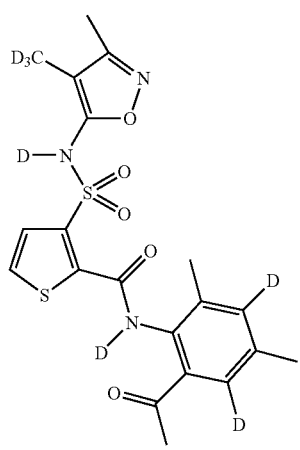
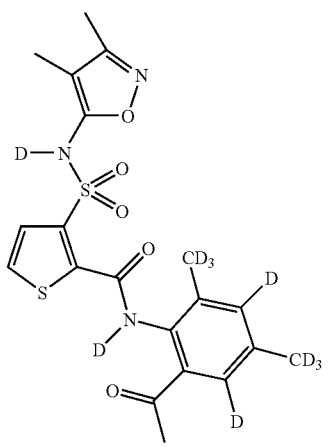

77
-continued
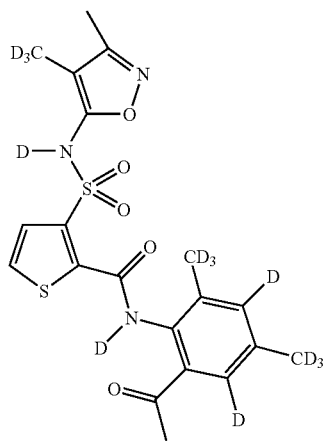
78
-continued
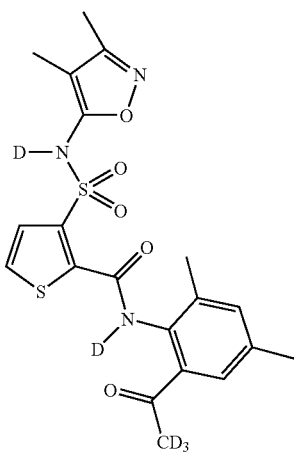

79
-continued
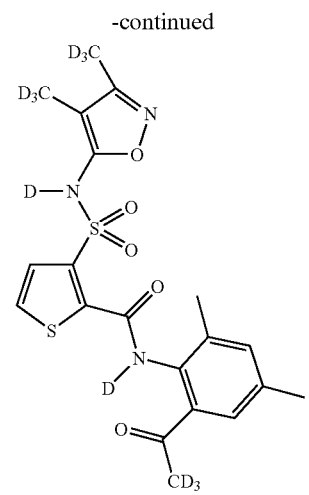
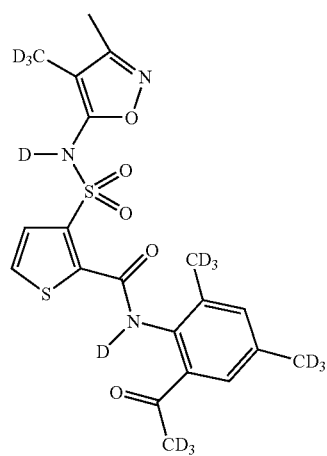
80
-continued
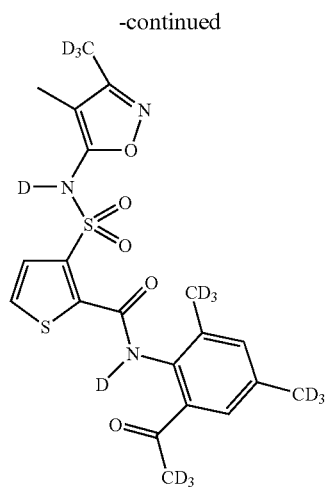
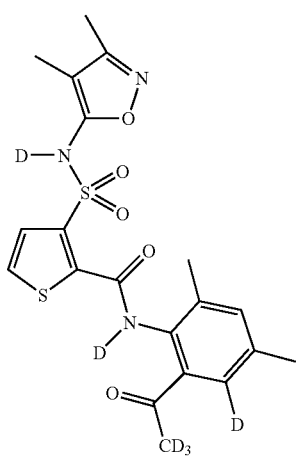

-continued
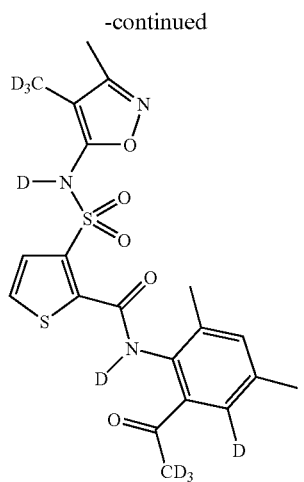
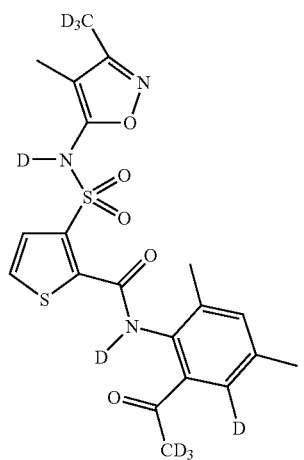
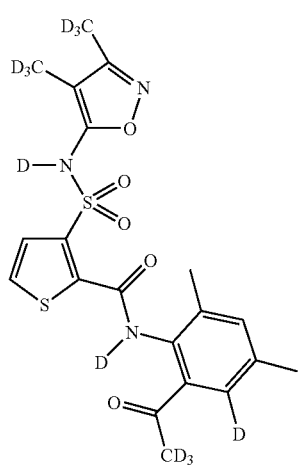
-continued
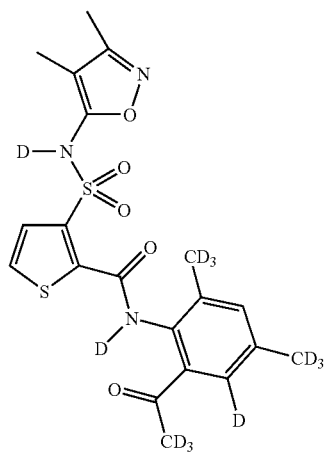
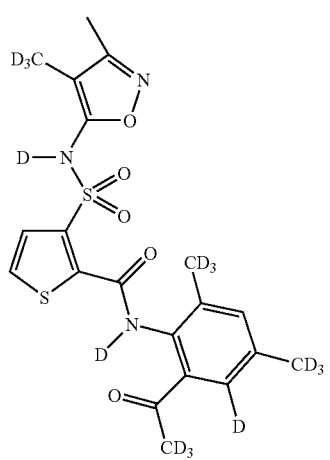
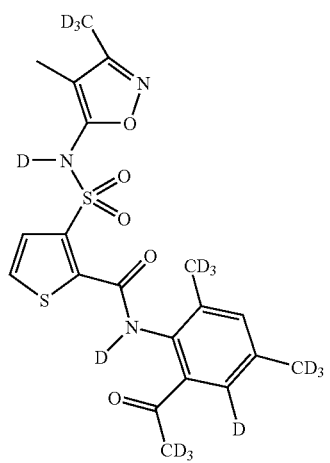

-continued
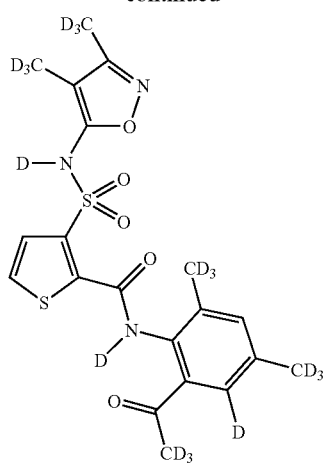
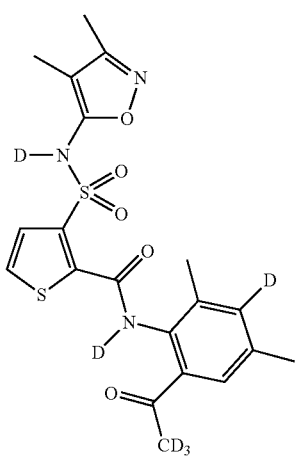
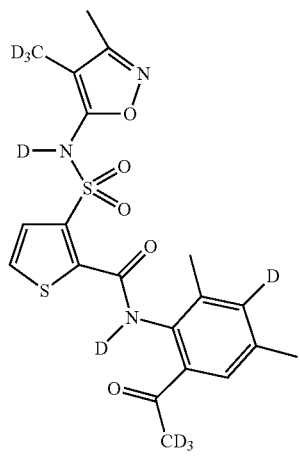
-continued
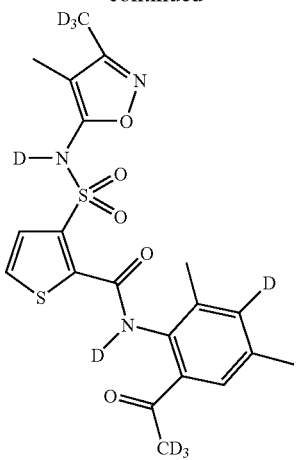
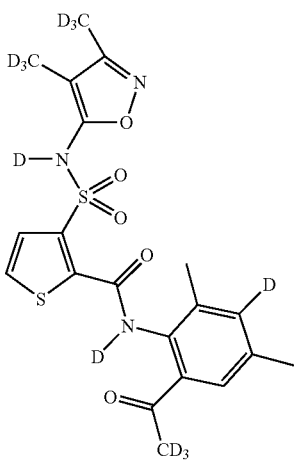
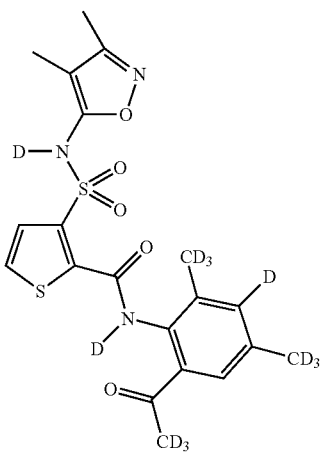

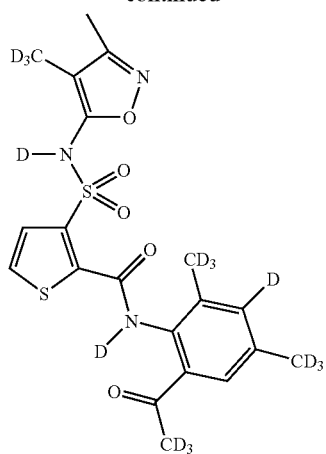
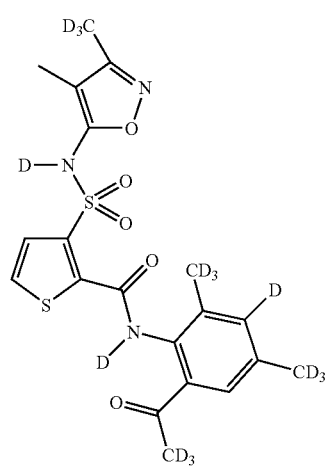
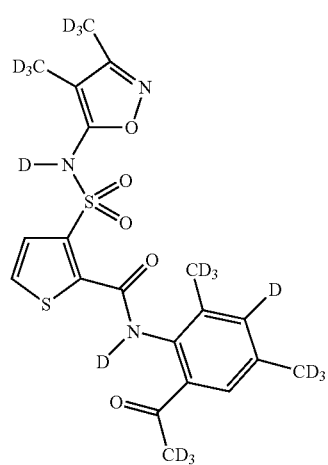
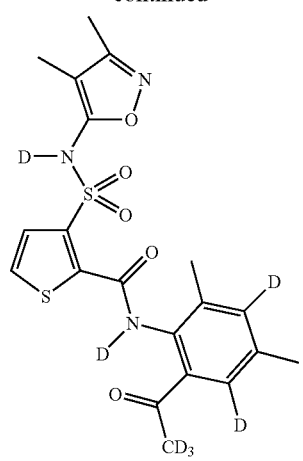
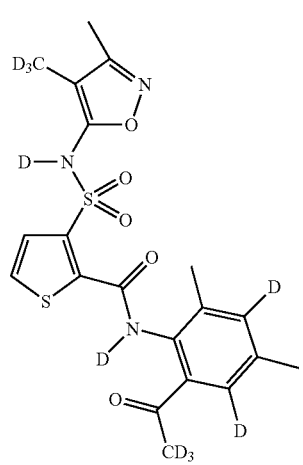
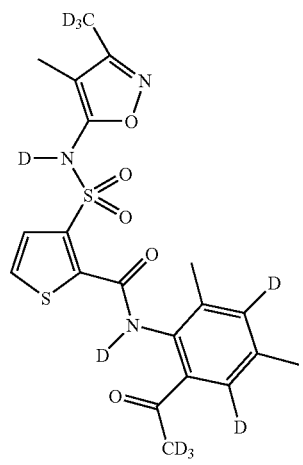

-continued
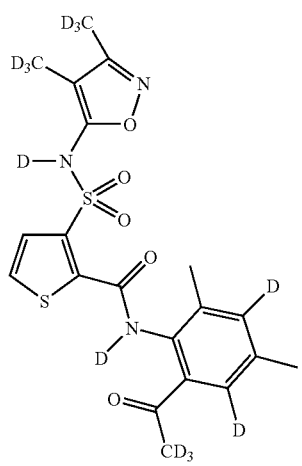
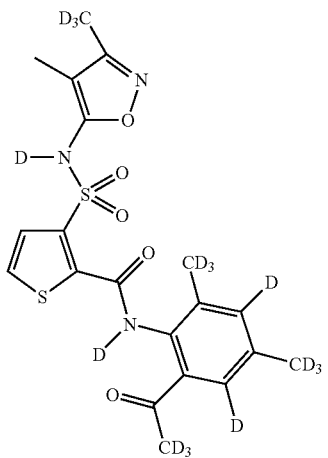
In yet another embodiment, the compound as disclosed herein is selected from the group consisting of:

-continued
89
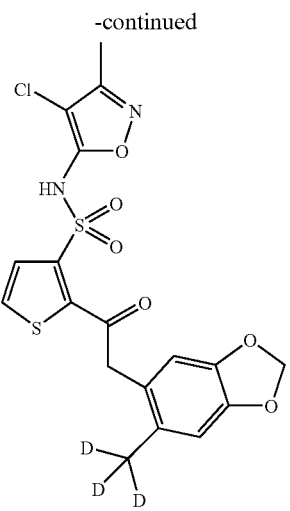
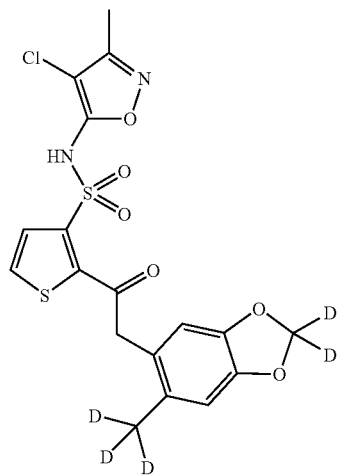
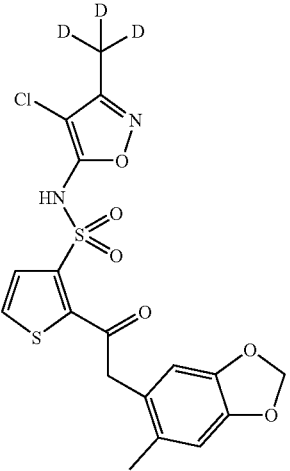
-continued
90
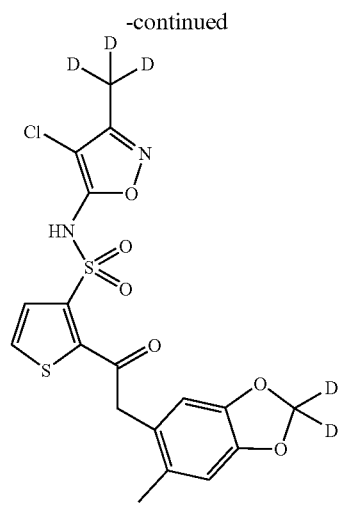
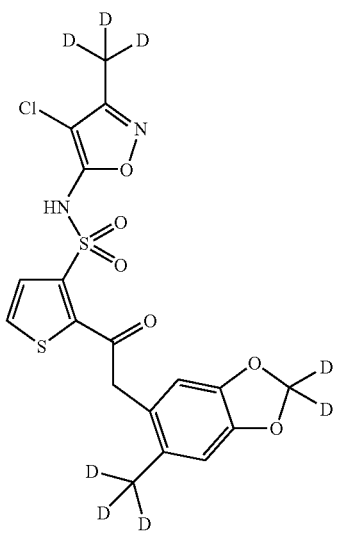

or a pharmaceutically acceptable salt, solvate, or prodrug thereof.

In another embodiment, at least one of the positions represented as D independently has deuterium enrichment of no less than about 1%, no less than about 5%, no less than about 10%, no less than about 20%, no less than about 50%, no less than about 70%, no less than about 80%, no less than about 90%, or no less than about 98%.

In a further embodiment, said compound is substantially a single enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, substantially an individual diastereomer, or a mixture of about 90% or more by weight of an individual diastereomer and about 10% or less by weight of any other diastereomer.

In certain embodiments, the compound as disclosed herein contains about 60% or more by weight of the (−)-enantiomer of the compound and about 40% or less by weight of (+)-enantiomer of the compound. In certain embodiments, the compound as disclosed herein contains about 70% or more by weight of the (−)-enantiomer of the compound and about 30% or less by weight of (+)-enantiomer of the compound. In certain embodiments, the compound as disclosed herein contains about 80% or more by weight of the (−)-enantiomer of the compound and about 20% or less by weight of (+)-enantiomer of the compound. In certain embodiments, the compound as disclosed herein contains about 90% or more by weight of the (−)-enantiomer of the compound and about 10% or less by weight of the (+)-enantiomer of the compound. In certain embodiments, the compound as disclosed herein contains about 95% or more by weight of the (−)-enantiomer of the compound and about 5% or less by weight of (+)-enantiomer of the compound. In certain embodiments, the compound as disclosed herein contains about 99% or more by weight of the (−)-enantiomer of the compound and about 1% or less by weight of (+)-enantiomer of the compound.

In certain embodiments, the compound as disclosed herein contains about 60% or more by weight of the (+)-enantiomer of the compound and about 40% or less by weight of (−)-enantiomer of the compound. In certain embodiments, the compound as disclosed herein contains about 70% or more by weight of the (+)-enantiomer of the compound and about 30% or less by weight of (−)-enantiomer of the compound. In certain embodiments, the compound as disclosed herein contains about 80% or more by weight of the (+)-enantiomer of the compound and about 20% or less by weight of (−)-enantiomer of the compound. In certain embodiments, the compound as disclosed herein contains about 90% or more by weight of the (+)-enantiomer of the compound and about 10% or less by weight of the (−)-enantiomer of the compound. In certain embodiments, the compound as disclosed herein contains about 95% or more by weight of the (+)-enantiomer of the compound and about 5% or less by weight of (−)-enantiomer of the compound. In certain embodiments, the compound as disclosed herein contains about 99% or more by weight of the (+)-enantiomer of the compound and about 1% or less by weight of (−)-enantiomer of the compound.

The deuterated compound as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

In certain embodiments, without being bound by any theory, the compound disclosed herein may expose a patient to a maximum of about 0.000005% $D_2O$ or about 0.00001% DHO, assuming that all of the C-D bonds in the compound as disclosed herein are metabolized and released as $D_2O$ or DHO. This quantity is a small fraction of the naturally occurring background levels of $D_2O$ or DHO in circulation. In certain embodiments, the levels of $D_2O$ shown to cause toxicity in animals is much greater than even the maximum limit of exposure because of the deuterium enriched compound as disclosed herein. Thus, in certain embodiments, the deuterium-enriched compound disclosed herein should not cause any additional toxicity because of the use of deuterium.

In one embodiment, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in Wu et al., *Journal of Medicinal Chemistry* 1997, 40(11), 1682-1689, Wu et al., *Synth. Commun.* 1999, 29(20), 3509-3516, and Wu et al., *Journal of Medicinal Chemistry* 1999, 42(22), 4485-4499, and references cited therein and routine modifications thereof. Compounds as disclosed herein can also be prepared as shown in any of the following schemes and routine modifications thereof.

For example, certain compounds as disclosed herein can be prepared as shown in Scheme 1.

Scheme 1

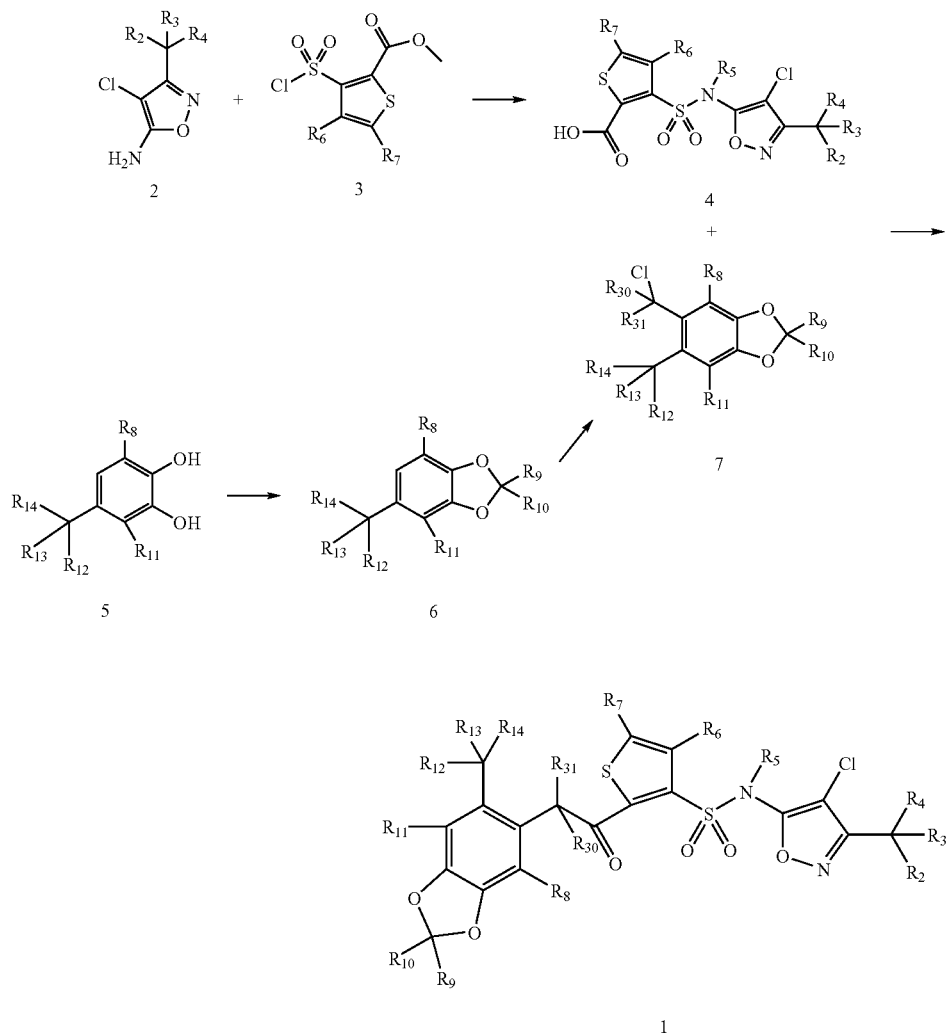

5-amino-isoxazole 2 reacts with thiophene-3-sulfonyl chloride 3, in the presence of a base, such as sodium hydride, in an appropriate solvent, such as anhydrous tetrahydrofuran, to give a thiophene-methyl ester, which is then treated with a base, such as sodium hydroxide, to give thiophene-carboxylic acid 4. Catechol 5 is treated with a base, such as cesium carbonate, in appropriate solvents, such dimethylformamide and dichloromethane, at an elevated temperature and under an inert atmosphere, such as nitrogen, to affored benzodioxole 6, which is then reacted with formaldehyde in the presence of an acid, such as hydrochloric acid, and in the presence of a catalyst, such as tetrabutylammonium bromide, in an appropriate solvent, such as ether, to yield chloromethyl-benzodioxole 7. Compound 4 is treated with coupling reagents, such as 1,1'-carbonyldiimidazole and N,O-dimethylhydroxylamine, in the presence of a base, such as imidazole, in an appropriate solvent, such as anhydrous tetrahydrofuran, to make a weinreb amide intermediate, which is then reacted with a Grignard reagent formed from compound 5, in an appropriate solvent, such as anhydrous tetrahydrofuran, to afford thiophene 8 of Formula I.

Deuterium can be incorporated to different positions synthetically, according to the synthetic procedures as shown in Scheme 1, by using appropriate deuterated intermediates. For example, to introduce deuterium at one or more positions selected from $R_2$, $R_3$, and $R_4$, 5-amino-4-chloro-3-methyl-isoxazole with the corresponding deuterium substitutions can be used. To introduce deuterium at one or more positions selected from $R_6$, and $R_7$, 2-(methoxycarbonyl)thiophene-3-sulfonyl chloride with the corresponding deuterium substitutions can be used. To introduce deuterium at one or more positions selected from $R_8$, $R_9$, $R_{10}$, $R_{11}$, $R_{12}$, $R_{13}$, $R_{14}$, $R_{30}$, and $R_{31}$, 5-(chloromethyl)-6-methylbenzo[d][1,3]dioxole with the corresponding deuterium substitutions can be used. These deuterated intermediates are either commercially available, or can be prepared by methods known to one of skill in the art or following procedures similar to those described in the Example section herein and routine modifications thereof.

Certain compounds of Formula I can be prepared as shown in Scheme 2.

Scheme 2

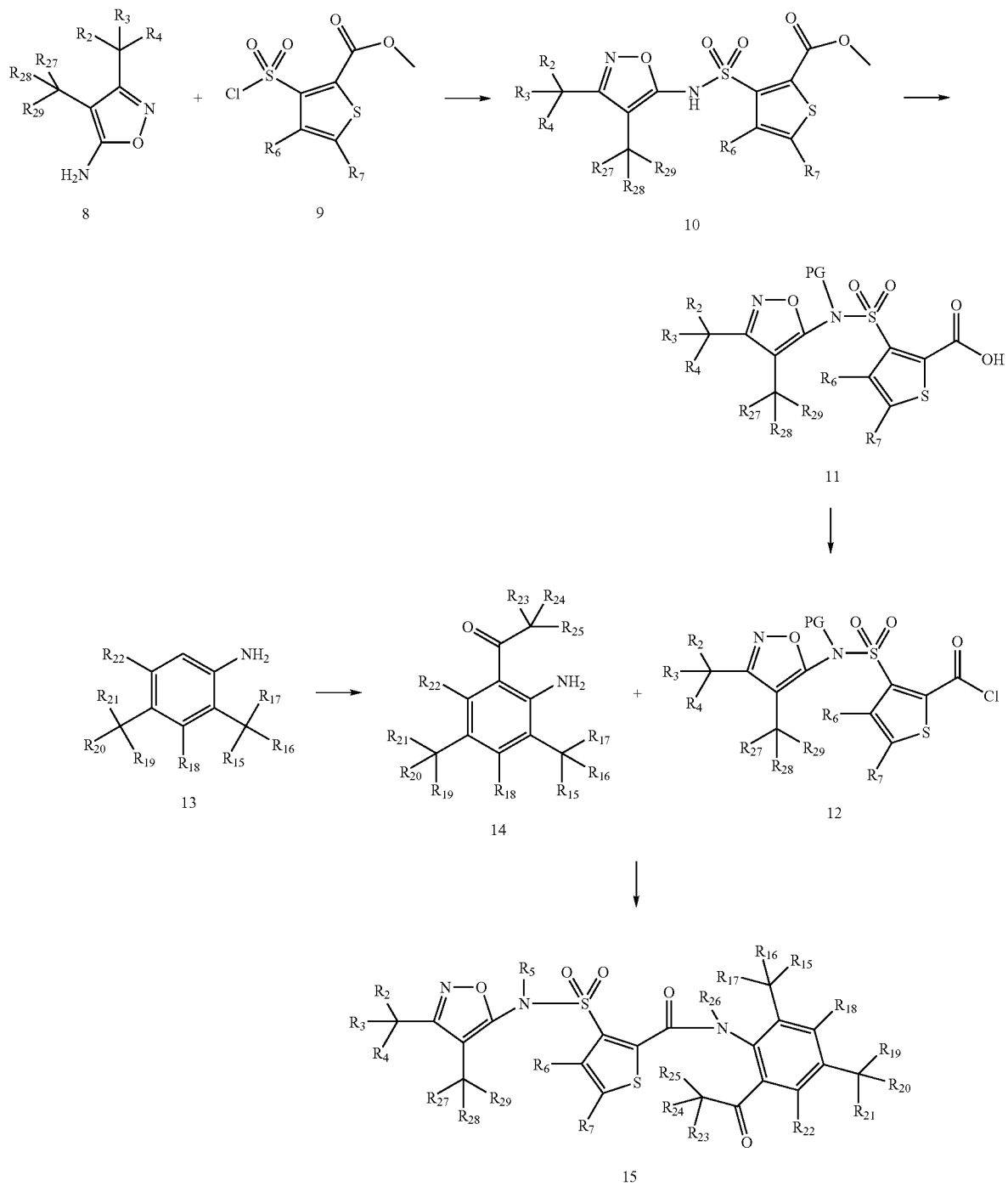

Amino-dimethylisoxazole 8 reacts with thiophene-3-sulfonyl chloride 9, in the presence of a base, such as sodium hydride, in an appropriate solvent, such as anhydrous tetrahydrofuran, to give a thiophene-methyl ester 10. Compound 10 is then reacted with a N-protecting group (PG), such as bromomethyl methyl ether, in an appropriate solvent, such as anyhydrous tetrahydrofuran, in the presence of a base, such as N,N-diisopropylethylamine to give a protected methyl ester thiopene intermediate, which is then treated with a base, such as sodium hydroxide, in an appropriate solvent, such as tetrahydrofuran, to give a protected thiophene carboxylic acid 11. Compound II reacts with a cholorinating agent, such as oxalyl chloride, in the presence of a catalyst, such as pyridine, in appropriate solvents, such as chloroform and terahydrofuran, to give thiophene carboxylic acid chloride 12. Aniline 13 is converted into acetophenone 14 by following the procedure disclosed in Wu, *Synth. Commun.* 1999, 29(20), 3509-3516, which then reacts with Compound II, in an appropriate solvent, such as anhydrous tetrahydrofuran, to give a protected thiophene intermediate, which is then deprotected by treating with an acid, such as hydrochloric acid, in an appropriate solvent, such as methanol, at an elevated temperature to afford thiophene 15 of Formula I.

Deuterium can be incorporated to different positions synthetically, according to the synthetic procedures as shown in Scheme 2, by using appropriate deuterated intermediates. For example, to introduce deuterium at one or more positions selected from $R_2$, $R_3$, $R_4$, $R_{27}$, $R_{28}$, and $R_{29}$, 5-amino-3,4-dimethylixoxazole with the corresponding deuterium substitutions can be used. To introduce deuterium at one or more positions selected from $R_6$, and $R_7$, 2-(methoxycarbonyl)thiophene-3-sulfonyl chloride with the corresponding deuterium substitutions can be used. To introduce deuterium at one or more positions selected from $R_{15}$, $R_{16}$, $R_{27}$, $R_{18}$, $R_{19}$, $R_{20}$, $R_{21}$, $R_{22}$, $R_{23}$, $R_{24}$, and $R_{25}$, 2-amino-3,5-dimethylacetophenone with the corresponding deuterium substitutions can be used. These deuterated intermediates are either commercially available, or can be prepared by methods known to one of skill in the art or following procedures similar to those described in the Example section herein and routine modifications thereof.

Exemplary conditions for forming and removing suitable N-protecting groups may be found in Greene and Wuts, Protective Groups in Organic Synthesis, $3^{rd}$ Ed., John Wiley & Sons, New York, N.Y., 1999. Suitable N-protecting groups include but are not limited to those selected from methoxymethyl (MOM), benzyloxymethyl (BOM), 2-(trimethylsilyl)ethoxymethyl (SEM), methoxyethoxymethyl (MEM), or t-butyl groups. In addition, the heteroaryl sulfonamide-NH moiety has reactivity similar to carboxylic acids, and accordingly, methods used to protect carboxylic acids may be applicable to protecting the nitrogen NH of the sulfonamides described herein. Exemplary conditions for forming and removing suitable carboxylic acid protecting groups may be found in Greene and Wuts, Protective Groups in Organic Synthesis, $3^{rd}$ Ed., John Wiley & Sons, New York, N.Y., 1999.

It is to be understood that the compounds disclosed herein may contain one or more chiral centers, chiral axes, and/or chiral planes, as described in "Stereochemistry of Carbon Compounds" Eliel and Wilen, John Wiley & Sons, New York, 1994, pp. 1119-1190. Such chiral centers, chiral axes, and chiral planes may be of either the (R) or (S) configuration, or may be a mixture thereof.

Another method for characterizing a composition containing a compound having at least one chiral center is by the effect of the composition on a beam of polarized light. When a beam of plane polarized light is passed through a solution of a chiral compound, the plane of polarization of the light that emerges is rotated relative to the original plane. This phenomenon is known as optical activity, and compounds that rotate the plane of polarized light are said to be optically active. One enantiomer of a compound will rotate the beam of polarized light in one direction, and the other enantiomer will rotate the beam of light in the opposite direction. The enantiomer that rotates the polarized light in the clockwise direction is the (+) enantiomer, and the enantiomer that rotates the polarized light in the counterclockwise direction is the (−) enantiomer. Included within the scope of the compositions described herein are compositions containing between 0 and 100% of the (+) and/or (−) enantiomer of compounds disclosed herein.

Where a compound as disclosed herein contains an alkenyl or alkenylene group, the compound may exist as one or mixture of geometric cis/trans (or Z/E) isomers. Where structural isomers are interconvertible via a low energy barrier, the compound disclosed herein may exist as a single tautomer or a mixture of tautomers. This can take the form of proton tautomerism in the compound disclosed herein that contains for example, an imino, keto, or oxime group; or so-called valence tautomerism in the compound that contain an aromatic moiety. It follows that a single compound may exhibit more than one type of isomerism.

The compounds disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When the compound disclosed herein contains an acidic or basic moiety, it may also disclosed as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound as disclosed herein may also be designed as a prodrug, which is a functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. DrugDelivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

Pharmaceutical Composition

Disclosed herein are pharmaceutical compositions comprising a compound as disclosed herein as an active ingredient, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof, in a pharmaceutically acceptable vehicle, carrier, diluent, or excipient, or a mixture thereof, in combination with one or more pharmaceutically acceptable excipients or carriers.

Disclosed herein are pharmaceutical compositions in modified release dosage forms, which comprise a compound as disclosed herein, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof; and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients or carriers.

Further disclosed herein are pharmaceutical compositions in enteric coated dosage forms, which comprise a compound as disclosed herein, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof; and one or more release controlling excipients or carriers for use in an enteric coated dosage form. The pharmaceutical compositions may also comprise non-release controlling excipients or carriers.

Further disclosed herein are pharmaceutical compositions in effervescent dosage forms, which comprise a compound as disclosed herein, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof; and one or more release controlling excipients or carriers for use in an enteric coated dosage form. The pharmaceutical compositions may also comprise non-release controlling excipients or carriers.

Additionally disclosed are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound as disclosed herein, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof; and one or more release controlling and non-release controlling excipients or carriers, such as those excipients or carriers suitable for a disruptable semi-permeable membrane and as swellable substances.

Disclosed herein also are pharmaceutical compositions in a dosage form for oral administration to a subject, which comprise a compound as disclosed herein, including a single enantiomer, a mixture of the (+)-enantiomer and the (−)-enantiomer, a mixture of about 90% or more by weight of the (−)-enantiomer and about 10% or less by weight of the (+)-enantiomer, a mixture of about 90% or more by weight of the (+)-enantiomer and about 10% or less by weight of the (−)-enantiomer, an individual diastereomer, or a mixture of diastereomers thereof, or a pharmaceutically acceptable salt, solvate, or prodrug thereof, and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

Disclosed herein are pharmaceutical compositions that comprise about 0.1 to about 1000 mg, about 1 to about 800 mg, about 2 to about 400 mg, about 1 mg, about 5 mg, about 10 mg, about 50 mg, about 100 mg, about 150 mg, about 200 mg, about 300 mg, about 500 mg, about 1000 mg of one or more compounds as disclosed herein, as film-coated tablets for oral administration. The pharmaceutical compositions further comprise microcrystalline cellulose, lactose monohydrate, hydroxypropyl methylcellulose, sodium starch glycolate, magnesium stearate, dibasic sodium phosphate, ascorbyl palmitate, edetate disodium dihydrate, monobasic sodium phosphatestearic acid, anatase titanium dioxide, yellow iron oxide, red iron oxide, and pharmaceutical talc.

The pharmaceutical compositions disclosed herein may be disclosed in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampoules, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The compound as disclosed herein may be administered alone, or in combination with one or more other compounds disclosed herein, one or more other active ingredients. The pharmaceutical compositions that comprise a compound disclosed herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease, disorder or condition.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

A. Oral Administration

The pharmaceutical compositions disclosed herein may be formulated in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions disclosed herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions disclosed herein varies upon the type of formulation, and is readily discernible to those of ordinary skill in the art. The pharmaceutical compositions disclosed herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions disclosed herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of nonaqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions disclosed herein may be formulated as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions disclosed herein may be formulated as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms disclosed herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions disclosed herein may be formulated in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) disclosed herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions disclosed herein for oral administration may be also formulated in the forms of liposomes, micelles, microspheres, or nanosystems. Micellar dosage forms can be prepared as described in U.S. Pat. No. 6,350,458.

The pharmaceutical compositions disclosed herein may be formulated as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions disclosed herein may be formulated as immediate or modified release dosage forms, including delayed-, sustained, pulsed-, controlled, targeted-, and programmed-release forms.

The pharmaceutical compositions disclosed herein may be co-formulated with other active ingredients which do not impair the desired therapeutic action, or with substances that supplement the desired action, such as drotrecogin-α, and hydrocortisone.

B. Parenteral Administration

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are formulated as ready-to-use sterile solutions. In another embodiment, the pharmaceutical compositions are formulated as sterile dry soluble products, including lyophilized powders and hypodermic tablets, to be reconstituted with a vehicle prior to use. In yet another embodiment, the pharmaceutical compositions are formulated as ready-to-use sterile suspensions. In yet another embodiment, the pharmaceutical compositions are formulated as sterile dry insoluble products to be reconstituted with a vehicle prior to use. In still another embodiment, the pharmaceutical compositions are formulated as ready-to-use sterile emulsions.

The pharmaceutical compositions disclosed herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions disclosed herein may be administered topically to the skin, orifices, or mucosa. The topical administration, as used herein, include (intra)dermal, conjuctival, intracorneal, intraocular, ophthalmic, auricular, transdermal, nasal, vaginal, uretheral, respiratory, and rectal administration.

The pharmaceutical compositions disclosed herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions disclosed herein may also comprise liposomes, micelles, microspheres, nanosystems, and mixtures thereof.

Pharmaceutically acceptable carriers and excipients suitable for use in the topical formulations disclosed herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryopretectants, lyoprotectants, thickening agents, and inert gases.

The pharmaceutical compositions may also be administered topically by electroporation, iontophoresis, phonophoresis, sonophoresis and microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions disclosed herein may be formulated in the forms of ointments, creams, and gels. Suitable ointment vehicles include oleaginous or hydrocarbon vehicles, including such as lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, Remington: The Science and Practice of Pharmacy, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, Carbopol®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions disclosed herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in Remington: The Science and Practice of Pharmacy, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions disclosed herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions disclosed herein may be administered ophthalmically in the forms of solutions, suspensions, ointments, emulsions, gel-forming solutions, powders for solutions, gels, ocular inserts, and implants.

The pharmaceutical compositions disclosed herein may be administered intranasally or by inhalation to the respiratory tract. The pharmaceutical compositions may be formulated in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be formulated as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient disclosed herein, a propellant as solvent; and/or a surfactant, such as sorbitan trioleate, oleic acid, or an oligolactic acid.

The pharmaceutical compositions disclosed herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions disclosed herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions disclosed herein for inhaled/intranasal administration may further comprise a suitable flavor, such as menthol and levomenthol, or sweeteners, such as saccharin or saccharin sodium.

The pharmaceutical compositions disclosed herein for topical administration may be formulated to be immediate release or modified release, including delayed-, sustained-, pulsed-, controlled-, targeted, and programmed release.

D. Modified Release

The pharmaceutical compositions disclosed herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions disclosed herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions disclosed herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(–)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions disclosed herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions disclosed herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s) and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Develop-*

*ment and Industrial Pharmacy* 2000, 26, 695-708; Verma et al., *J. Controlled Release* 2002, 79, 7-27).

In certain embodiments, the pharmaceutical compositions disclosed herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions disclosed herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions disclosed herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions disclosed herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

Methods of Use

Disclosed are methods for treating, preventing, or ameliorating one or more symptoms of an endothelin-mediated disorder, comprising administering to a subject having or being suspected to have such a disorder, a therapeutically effective amount of a compound as disclosed herein or a pharmaceutically acceptable salt, solvate, and prodrug thereof.

Endothelin-mediated disorders include, but are not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can be lessened, alleviated, or prevented by administering an endothelin receptor modulator. Endothelin-mediated disorders also include conditions that result from therapy with agents, such as erythropoietin and immunosuppressants, which elevate endothelin levels.

Also disclosed are methods of treating, preventing, or ameliorating one or more symptoms of a disorder associated with one or more endothelin receptors, including, $ET_A$ and $ET_B$, by administering to a subject having or being suspected to have such a disorder, a therapeutically effective amount of a compound as disclosed herein or a pharmaceutically acceptable salt, solvate, and prodrug thereof.

Further disclosed are methods of treating, preventing, or ameliorating one or more symptoms of a disorder responsive to modulation of one or more endothelin receptors, including $ET_A$ and $ET_B$, comprising administering to a subject having or being suspected to have such a disorder, a therapeutically effective amount of a compound as disclosed herein or a pharmaceutically acceptable salt, solvate, and prodrug thereof.

Furthermore, disclosed herein are methods of modulating the activity of one or more endothelin receptors, including $ET_A$ and $ET_B$, comprising contacting the receptor(s) with one or more of the compounds as disclosed herein or a pharmaceutically acceptable salt, solvate, and prodrug thereof. In one embodiment, the receptor(s) is expressed by a cell.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator, or for preventing such disorder, in a subject prone to the disorder; comprising administering to the subject a therapeutically effective amount of a compound of as disclosed herein or a pharmaceutically acceptable salt, solvate, and prodrug thereof.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator; or for preventing such a disorder, in a subject prone to the disorder; comprising administering to the subject a therapeutically effective amount of a compound as disclosed herein or a pharmaceutically acceptable salt, solvate, or prodrug thereof; so as to affect decreased inter-individual variation in plasma levels of the compound or a metabolite thereof, during the treatment of the disease as compared to the corresponding non-isotopically enriched compound.

In certain embodiments, the inter-individual variation in plasma levels of the compounds as disclosed herein, or metabolites thereof, is decreased by greater than about 5%, greater than about 10%, greater than about 20%, greater than about 30%, greater than about 40%, or by greater than about 50% as compared to the corresponding non-isotopically enriched compound.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator; or for preventing such a disorder, in a subject prone to the disorder; comprising administering to the subject a therapeutically effective amount of a compound as disclosed herein or a pharmaceutically acceptable salt, solvate, or prodrug thereof; so as to affect increased average plasma levels of the compound or decreased average plasma levels of at least one metabolite of the compound per dosage unit as compared to the corresponding non-isotopically enriched compound.

In certain embodiments, the average plasma levels of the compound as disclosed herein are increased by greater than about 5%, greater than about 10%, greater than about 20%, greater than about 30%, greater than about 40%, or greater than about 50% as compared to the corresponding non-isotopically enriched compounds.

In certain embodiments, the average plasma levels of a metabolite of the compound as disclosed herein are decreased by greater than about 5%, greater than about 10%, greater than about 20%, greater than about 30%, greater than about 40%, or greater than about 50% as compared to the corresponding non-isotopically enriched compounds Plasma levels of the compound as disclosed herein, or metabolites thereof, may be measured using the methods described by Li et al. (*Rapid Communications in Mass Spectrometry* 2005, 19, 1943-1950).

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator; or for preventing such disorder, in a subject prone to the disorder; comprising administering to the subject a therapeutically effective amount of a compound as disclosed herein or a pharmaceutically acceptable salt, solvate, or prodrug thereof; so as to affect a decreased inhibition of, and/or metabolism by at least one cytochrome $P_{450}$ or monoamine oxidase isoform in the subject during the treatment of the disease as compared to the corresponding non-isotopically enriched compound.

Examples of cytochrome $P_{450}$ isoforms in a mammalian subject include, but are not limited to, CYP1A1, CYP1A2, CYP1B1, CYP2A6, CYP2A13, CYP2B6, CYP2C8, CYP2C9, CYP2C18, CYP2C19, CYP2D6, CYP2E1, CYP2G1, CYP2J2, CYP2R1, CYP2S1, CYP3A4, CYP3A5, CYP3A5P1, CYP3A5P2, CYP3A7, CYP4A11, CYP4B1, CYP4F2, CYP4F3, CYP4F8, CYP4F11, CYP4F12, CYP4X1, CYP4Z1, CYP5A1, CYP7A1, CYP7B1, CYP8A1, CYP8B1, CYP11A1, CYP11B1, CYP11B2, CYP17, CYP19, CYP21, CYP24, CYP26A1, CYP26B1, CYP27A1, CYP27B1, CYP39, CYP46, and CYP51.

Examples of monoamine oxidase isoforms in a mammalian subject include, but are not limited to, $MAO_A$, and $MAO_B$.

In certain embodiments, the decrease in inhibition of the cytochrome $P_{450}$ or monoamine oxidase isoform by a compound as disclosed herein is greater than about 5%, greater than about 10%, greater than about 20%, greater than about 30%, greater than about 40%, or greater than about 50% as compared to the corresponding non-isotopically enriched compounds.

The inhibition of the cytochrome $P_{450}$ isoform is measured by the method of Ko et al. (*British Journal of Clinical Pharmacology*, 2000, 49, 343-351). The inhibition of the $MAO_A$ isoform is measured by the method of Weyler et al. (*J. Biol. Chem.* 1985, 260, 13199-13207). The inhibition of the $MAO_B$ isoform is measured by the method of Uebelhack et al. (*Pharmacopsychiatry*, 1998, 31, 187-192).

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator; or for preventing such disorder, in a subject prone to the disorder; comprising administering to the subject a therapeutically effective amount of a compound of a compound as disclosed herein or a pharmaceutically acceptable salt, solvate, or prodrug thereof; so as to affect a decreased metabolism via at least one polymorphically-expressed cytochrome $P_{450}$ isoform in the subject during the treatment of the disorder as compared to the corresponding non-isotopically enriched compound.

Examples of polymorphically-expressed cytochrome $P_{450}$ isoforms in a mammalian subject include, but are not limited to, CYP2C8, CYP2C9, CYP2C19, and CYP2D6.

In certain embodiments, the decrease in metabolism of the compound as disclosed herein by at least one polymorphically-expressed cytochrome $P_{450}$ isoforms cytochrome $P_{450}$ isoform is greater than about 5%, greater than about 10%, greater than about 20%, greater than about 30%, greater than about 40%, or greater than about 50% as compared to the corresponding non-isotopically enriched compound.

The metabolic activities of the cytochrome $P_{450}$ isoforms are measured by the method described in Example 9. The metabolic activities of the monoamine oxidase isoforms are measured by the methods described in Examples 10, 11, and 12.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator, or for preventing such disorder, in a subject prone to the disorder; comprising administering to the subject a therapeutically effective amount of a compound as disclosed herein or prodrug thereof; so as to affect at least one statistically-significantly improved disorder-control and/or disorder-eradication endpoint, as compared to the corresponding non-isotopically enriched compound.

Examples of statistically-significantly improved disorder-control and/or disorder-eradication endpoints include, but are not limited to, statistically-significant decrease in mean blood pressure, decrease in mean diastolic blood pressure, decrease in mean systolic blood pressure, decrease in pulmonary arterial pressure, increased survival rate, and an increase in the therapeutic index with respect to hepatotoxicity.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator, or for preventing such disorder, in a subject prone to the disorder; comprising administering to the subject a therapeutically effective amount of a compound disclosed herein or a pharmaceutically acceptable salt, solvate, or prodrug thereof; so as to affect an improved clinical effect as compared to the corresponding non-isotopically enriched compound. Examples of improved clinical effects include, but are not limited to, maintenance of clinical benefit, statistically-significant decrease in mean blood pressure, decrease in mean diastolic blood pressure, decrease in mean systolic blood pressure, decrease in pulmonary arterial pressure, increased survival rate, and an increase in the therapeutic index with respect to hepatotoxicity.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator, or for preventing such disorder, in a subject prone to the disorder; comprising administering to the subject a therapeutically effective amount of a compound as disclosed herein or a pharmaceutically acceptable salt, solvate, or prodrug thereof; so as to affect prevention of recurrence of abnormal cardiac parameters as the primary clinical benefit, which includes absence of statistically-significant abnormality in mean blood pressure, mean diastolic blood pressure, systolic blood pressure, and pulmonary arterial pressure, and maintenance of increased survival rate, and/or maintain absence of hepatotoxicity, as compared to the corresponding non-isotopically enriched compound.

Disclosed herein are methods for treating a subject, including a human, having or suspected of having a disorder involving, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator, or for preventing such disorder, in a subject prone to the disorder; comprising administering to the subject a therapeutically effective amount of a compound disclosed herein or a pharmaceutically acceptable salt, solvate, or prodrug thereof; so as to allow the treatment of, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction and/or any disorder which can lessened, alleviated, or prevented by administering an endothelin receptor modulator while reducing or eliminating deleterious changes in any diagnostic hepatobiliary function endpoints as compared to the corresponding non-isotopically enriched compound.

Examples of diagnostic hepatobiliary function endpoints include, but are not limited to, alanine aminotransferase ("ALT"), serum glutamic-pyruvic transaminase ("SGPT"), aspartate aminotransferase ("AST" or "SGOT"), ALT/AST ratios, serum aldolase, alkaline phosphatase ("ALP"), ammonia levels, bilirubin, gamma-glutamyl transpeptidase ("GGTP," "γ-GTP," or "GGT"), leucine aminopeptidase ("LAP"), liver biopsy, liver ultrasonography, liver nuclear scan, 5'-nucleotidase, and blood protein. Hepatobiliary endpoints are compared to the stated normal levels as given in "Diagnostic and Laboratory Test Reference", 4$^{th}$ edition, Mosby, 1999. These assays are run by accredited laboratories according to standard protocol.

Depending on the disorder to be treated and the subject's condition, the compound as disclosed herein may be administered by oral, parenteral (e.g., intramuscular, intraperitoneal, intravenous, ICV, intracistemal injection or infusion, subcutaneous injection, or implant), inhalation, nasal, vaginal, rectal, sublingual, or topical (e.g., transdermal or local) routes of administration, and may be formulated, alone or together, in suitable dosage unit with pharmaceutically acceptable carriers, adjuvants and vehicles appropriate for each route of administration.

The dose may be in the form of one, two, three, four, five, six, or more sub-doses that are administered at appropriate intervals per day. The dose or sub-doses can be administered in the form of dosage units containing from 0.1 to 500 milligram, from 0.1 to 200 milligrams, or from 0.5 to 100 milligram active ingredient(s) per dosage unit, and if the condition of the patient requires, the dose can, by way of alternative, be administered as a continuous infusion.

In certain embodiments, an appropriate dosage level is about 0.001 to about 100 mg per kg patient body weight per day (mg/kg per day), about 0.01 to about 50 mg/kg per day, about 0.01 to about 25 mg/kg per day, or about 0.05 to about 10 mg/kg per day, which may be administered in single or multiple doses. A suitable dosage level may be about 0.01 to 25 mg/kg per day, about 0.05 to 10 mg/kg per day, or about 0.1 to 5 mg/kg per day. Within this range the dosage may be 0.005 to 0.05, 0.05 to 0.5 or 0.5 to 5.0 mg/kg per day.

Combination Therapy

The compounds disclosed herein may also be combined or used in combination with other agents useful in the treatment, prevention, or amelioration of one or more symptoms of the disorders for which the compound disclosed herein are useful, including, but not limited to, hypertension, cardiovascular disease, cardiac disease, pulmonary hypertension, neonatal pulmonary hypertension, erythropoietin-mediated hypertension, respiratory disease, inflammatory disease, opthalmologic disease, gastroenteric disease, renal failure, endotoxin shock, menstrual disorder, obstetric condition, wound, laminitis, erectile dysfunction, menopause, osteoporosis, metabolic bone disorder, climacteric disorder, disorder associated with the reduction in ovarian function in middle-aged women, pre-eclampsia, management of labor during pregnancy, nitric oxide attenuated disorder, anaphylactic shock, interstitial lung disease, congestive heart failure, hemorrhagic shock, immunosuppressant-mediated renal vasoconstriction, any disorder which can lessened, alleviated, or prevented by administering an endothelin receptor modulator, and/or disorders that result from therapy with agents, such as erythropoietin and immunosuppressants, which elevate endothelin levels.

Such other agents, or drugs, may be administered, by a route and in an amount commonly used therefor, simultaneously or sequentially with an amine salt disclosed herein. When a compound as disclosed herein is used contemporaneously with one or more other drugs, a pharmaceutical composition containing such other drugs in addition to the compound disclosed herein may be utilized, but is not required. Accordingly, the pharmaceutical compositions disclosed herein include those that also contain one or more other active ingredients or therapeutic agents, in addition to the compound disclosed herein.

In certain embodiments, the compounds disclosed herein can be combined with one or more other compounds known to modulate the activity of one or more endothelin receptors, including $ET_A$ and $ET_B$. Non-limiting examples of other endothelin antagonists are those described in U.S. Pat. Nos. 6,852,745; 6,686,382; 6,683,103; 6,432,994; 6,248,767; 5,962,490; 5,783,705; 5,594,021; 5,591,761; 5,571821; and 5,514,691.

In certain embodiments, the compounds disclosed herein can be combined with one or more endothelin antagonist known in the art, including, but not limited to, Bosentan, cyclo(D-Glu-L-Ala-allo-D-Ile-L-Leu-D-Trp) (BE-18257B); cyclic pentapeptides related to BE-18257B, such as cyclo(D-Asp-Pro-D-Val-Leu-D-Trp) (BQ-123) (U.S. Pat. No. 5,114, 918; and EP A1 0 436 189); and other peptide and non-peptidic $ET_A$ antagonists that have been identified in, for example, U.S. Pat. Nos. 6,953,780; 6,946,481; 6,686,382; 6,683,103; 6,852,745; 6,835,741; 6,673,824; 6,670,367; 6,670,362; 6,432,994; 6,248,767; 5,962,490; 5,783,705; 5,594,021; 5,591,761; 5,571821; 5,514,691; 5,352,800; 5,352,659; 5,334,598; 5,248,807; 5,240,910; 5,198,548; 5,187,195; and 5,082,838.

These known endothelin antagonists also include other cyclic pentapeptides, acyltripeptides, hexapeptide analogs, anthraquinone derivatives, indanecarboxylic acids, N-pyriminylbenzenesulfonamides, benzenesulfonamides, naphthalenesulfonamides (Canadian Pat. App. Nos. 2,067,288 and 2,071,193; EP A1 0 569 193; EP A1 0 558 258; EP A1 0 436 189; U.S. Pat. Nos. 5,612,359; 5,594,021; 5,591,761; 5,571, 821; 5,514,696; 5,514,691; 5,464,853; 5,378,715; 5,270,313; 5,208,243; WO 96/31492; WO 97/27979; WO93/08799; Nakajima et al., *J. Antibiot.* 1991, 44, 1348-1356; Miyata et al., *J. Antibiot.* 1992, 45, 74-8; Ishikawa et al., *J. Med. Chem.* 1992, 35, 2139-2142; Cody et al., *Med. Chem. Res.* 1993, 3, 154-162; Miyata et al., *J. Antibiot.* 1992, 45, 1041-1046; Miyata et al., *J. Antibiot.* 1992, 45, 1029-1040; Fujimoto et al., *FEBS Lett.* 1992, 305, 41-44; EP A1 0 496 452; Clozel et al., *Nature* 1993, 365, 759-761; Nishikibe et al., *Life Sci.* 1993, 52, 717-724; and Benigni et al., *Kidney Int.* 1993, 44, 440-444).

Additional known endothelin antagonists include those described in DE 4341663; EP 743307; EP 733626; EP 713875; EP 682016; EP 658548; EP 633259; EP 628569; EP 617001; EP 601386; EP 555537; EP 552417; EP 526708; EP 510526; EP 496-452; EP 436189; GB 2295616; GB 2277446; GB 2276383; GB 2275926; GB 2266890; JP 8059635; JP 7330622; JP 7316188; JP 7258098; JP 7133254; JP 6256261; JP 6122625; U.S. Pat. Nos. 6,080,774; 5,780,473; 5,543,521; 5,965,732; 5,571,821; 5,559,105; 5,541,186; 5,482,960; 5,420,123; 5,389,620; 5,292,740; WO 96/33190; WO 96/33170; WO 96/31492; WO 96/30358; WO 96/23773; WO 96/22978; WO 96/20177; WO 96/19459; WO 96/19455; WO 96/15109; WO 96/12706; WO 96/11927; WO 96/11914; WO 96/09818; WO 96/08487; WO 96/08483; WO 96/08486; WO 96/07653; WO 96/06095; WO 96/04905; WO 95/35107; WO 95/33752; WO 95/33748; WO 95/26957; WO 95/26716; WO 95/26360; WO 95/15963; WO 95/15944; WO 95/13262; WO 95/12611; WO 95/05376; WO 95/08989; WO 95/08550; WO 95/05374; WO 95/05372; WO 95/04534; WO 95/04530; WO 95/03295; WO 95/03044; WO 94/25013; WO 94/24084; WO 94/21590; WO 94/21259; WO 94/14434; WO 94/03483; WO 94/02474; WO 93/25580; WO 93/23404; WO 93/21219; and WO 93/08799.

These known endothelin antagonists also include BQ-123 (Ihara et al., *Life Sciences* 1992, 50, 247-255); PD 156707 (Reynolds et al., *J. Pharm. Exper. Ther.* 1995, 273, 1410-1417); L-754,142 (Williams et al., *J. Pharm. Exper. Ther.* 1995, 275, 1518-1526); SB 209670 (Ohlstein et al., *Proc. Natl. Acad. Sci. USA* 1994, 91, 8052-8056); SB 217242 (Ohlstein et al., *J. Pharm. Exper. Ther.* 1996, 276, 609-615); A-127722 (Opgenorth et al., *J. Pharm. Exper. Ther.* 1996, 276, 473-481); TAK-044 (Masuda et al., *J. Pharm. Exper. Ther.* 1996, 279, 675-685 (1996).

In certain embodiments, the compounds disclosed herein can be combined with other compounds that are used in treatment of congestive heart failure, including, but not limited to, loop diuretics, such as bumetanide, furosemide, and torsemide; thiazide diuretics, such as chlorthalidone, hydrochlorothiazide (HCTZ), amiloride, and spironolactone; long-acting nitrates, such as glyceryl trinitrate, isosorbide dinitrate, isosorbide mononitrate, and molsidomin pentaerythritol tetranitrate; β-blockers, such as alprenolol, oxprenolol, pindolol, propranolol, timolol, sotalol, nadolol, mepindolol, carteolol, tertatolol, bopindolol, bupranolol, penbutolol, cloranolol, practolol, metoprolol, atenolol, acebutolol, betaxolol, bevantolol, bisoprolol, celiprolol, esmolol, epanolol, s-atenolol, nebivolol, talinolol, labetalol, and carvedilol; calcium channel blockers, such as amlodipine, felodipine, isradipine, nicardipine, nifedipine, nimodipine, nisoldipine, nitrendipine, lacidipine, nilvadipine, manidipine, barnidipine, lercanidipine, cilnidipine, benidipine, mibefradil, verapamil, gallopamil, diltiazem, fendiline, bepridil, lidoflazine, and perhexyline; renin inhibitors, such as aliskiren, remikiren; angiotensin converting enzyme (ACE) inhibitors, such as alacepril, benazepril, captopril, ceranapril, delapril, enalapril, fosinopril, lisinopril, moexipril, perindopril, quinapril, ramipril, spirapril, trandolapril, and zofenopril; angiotensin receptor blockers (ARBs), such as candesartan, eprosartan, irbesartan, losartan, olmesartan, tasosartan, telmisartan, valsartan; and aldosterone antagonists, such as spironolactone and eplerenone.

The compounds disclosed herein can also be administered in combination with other classes of compounds, including, but not limited to, endothelin converting enzyme (ECE) inhibitors, such as phosphoramidon; thromboxane receptor antagonists, such as ifetroban; potassium channel openers; thrombin inhibitors, such as hirudin; growth factor inhibitors, such as modulators of PDGF activity; platelet activating factor (PAF) antagonists; anti-platelet agents, such as GPIIb/IIIa blockers (e.g., abdximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopepsidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, or atavastatin or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothlazide, hydrochlorothiazide, flumethiazide, hydroflumethiazide, bendroflumethiazide, methylchlorothiazide, trichloromethiazide, polythiazide, benzothlazide, ethacrynic acid, tricrynafen, chlorthalidone, furosenilde, musolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g. metformin), glucosidase inhibitors (e.g., acarbose), insulins, meglitinides (e.g., repaglinide), sulfonylureas (e.g., glimepiride, glyburide, and glipizide), thiozolidinediones (e.g. troglitazone, rosiglitazone and pioglitazone), and PPAR-gamma agonists; mineralocorticoid receptor antagonists, such as spironolactone and eplerenone; growth hormone secretagogues; aP2 inhibitors; non-steroidal antiinflammatory drugs (NSAIDS), such as aspirin and ibuprofen; phosphodiesterase inhibitors, such as PDE III inhibitors (e.g., cilostazol) and PDE V inhibitors (e.g., sildenafil, tadalafil, vardenafil); protein tyrosine kinase inhibitors; antiinflammatories; antiproliferatives, such as methotrexate, FK506 (tacrolimus, Prograf), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrridine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, and octreotide acetate; microtubule-disruptor agents, such as ecteinascidins; microtubule-stablizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathiprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin, and carboplatin.

These other therapeutic agents may be used, for example, in the amounts indicated in the Physicians' Desk Reference (PDR) or as otherwise determined by one of ordinary skill in the art.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers can be formed from a variety of materials such as glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprise a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but are not limited to, buffers, diluents, filters, needles, syringes; carrier, package, container, vial and/ or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself, a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein. These other therapeutic agents may be used, for example, in the amounts indicated in the Physicians' Desk Reference (PDR) or as otherwise determined by one of ordinary skill in the art.

The invention is further illustrated by the following examples:

Example 1

2-[2-(6-Methyl-benzo[1,3]dioxol-5-yl)-acetyl]-thiophene-3-sulfonic acid (4-chloro-3-methyl-isoxazol-5-yl)-amide Step 1

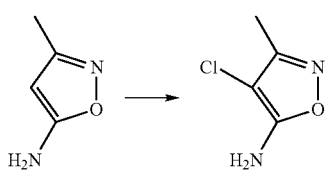

5-amino-4-chloro-3-methylisoxazole: At about 0° C., N-chlorosuccinimide (1.85 g, 10.2 mmol) was slowly added to a solution of 5-amino-3-methylisoxazole (1 g, 10.2 mmol) in 20 mL of dichloromethane. Under continuous stirring, the mixture was maintained at about 0° C. for about 1 hour and then at ambient temperature for about 2 hours. The mixture was washed with aqueous 1N sodium hydroxide. After standard extractive work up, the residue was washed with hexane to afford the product 5-amino-4-chloro-3-methylisoxazole (0.5 g, 37%). $^1$H NMR (300 MHz, CDCl$_3$) δ 4.64 (br. s, 2H), 2.17 (s, 3H).

Step 2

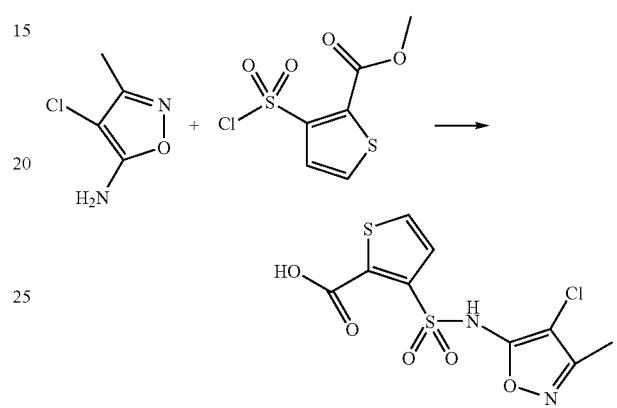

3-(4-Chloro-3-methyl-isoxazol-5-ylsulfamoyl)-thiophene-2-carboxylic acid: At about 0° C., sodium hydride (60% dispersion in mineral oil, 458 mg, 19 mmol) was added to a solution of 5-amino-4-chloro-3-methylisoxazole (1.1 g, 8.3 mmol) in anhydrous tetrahydrofuran (30 mL). The resulting mixture was stirred for about 10 minutes and 2-(methoxycarbonyl)thiophene-3-sulfonyl chloride (1.95 g, 8.11 mmol) was slowly added. Under continuous stirring, the mixture was maintained at ambient temperature for about 4 hours. The mixture was then diluted with hexanes (30 mL) and the resulting precipitate was filtered and washed with hexanes. The precipitate was then dissolved in 1 N sodium hydroxide and stirred at ambient temperature for about 1 hour. After acidifying to pH ~2 with 2 N hydrochloric acid, the resulting precipitate was filtered, washed with water, and dried in vacuo to give the desired product 3-[(4-chloro-3-methyl-5-isoxazolyl)sulfamoyl]-2-thiophenecarboxylic acid (1.2 g, 45%) as a yellow powder. $^1$H NMR (300 MHz, CD$_3$OD) δ 7.82 (d, J=5.4 Hz, 1H), 7.53 (d, J=5.4 Hz, 1H), 2.24 (s, 3H); LC-MS: m/z=323 (MH)$^+$.

Step 3

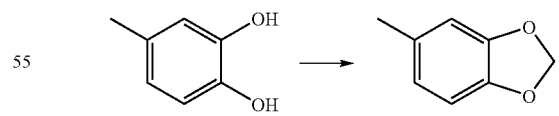

5-Methyl-benzo[1,3]dioxole: 4-methylcatechol (15 g, 120.9 mmol) was added to a suspension of cesium carbonate (50 g, 154 mmol) in dimethylformamide (60 mL). The mixture was put under vacuum and purged with nitrogen three times. At ambient temperature, dichloromethane (15.4 g, 181.3 mmol) was added, and then the reaction mixture was heated at about 110° C. for about 2 hours. After cooling to ambient temperature, the reaction was quenched with water (500 mL) and extracted with ether-pentane (1:1 ratio, 3×500

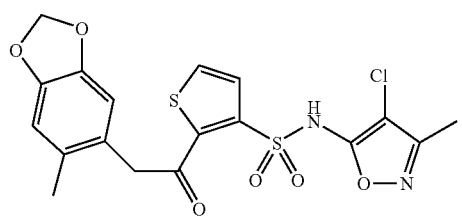

mL). The combined organic layers were washed with water (3×1000 mL), dried over anhydrous magnesium sulfate, filtered and concentrated in vacuo to afford the desired product (50 g, 30%). $^1$H NMR (300 MHz, CDCl$_3$) δ 6.71-6.59 (m, 3H), 5.88 (s, 2H), 2.27 (s, 3H); GC-MS: m/z=136 (MH)$^+$.

Step 4

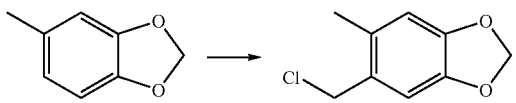

5-(Chloromethyl)-6-methylbenzo[d][1,3]dioxole: At about 0° C., 5-methylbenzo[d][1,3]dioxole (500 mg, 3.68 mmol) and formaldehyde (37% in water, 0.7 mL) were sequentially added to a mixture of dichloromethane (6.8 mL), tetrabutylammonium bromide (80 mg) and concentrated hydrochloric acid (6.5 mL). Under continuous stirring, the mixture was maintained at about 0° C. for about 1 hour and then at ambient temperature for about 4 hours. The mixture was diluted with ether (100 mL). After standard extractive workup, the resulting solid residue was heated with hexanes (100 mL) and the insolubles were removed by filtration. The filtrate was concentrated to give desired product (420 mg, 62%). $^1$H NMR (300 MHz, CDCl$_3$) δ 6.89 (s, 1H), 6.69 (s, 1H), 5.94 (s, 3H), 4.56 (s, 2H), 2.35 (s, 3H); GC-MS: m/z=184 (MH)$^+$.

Step 5

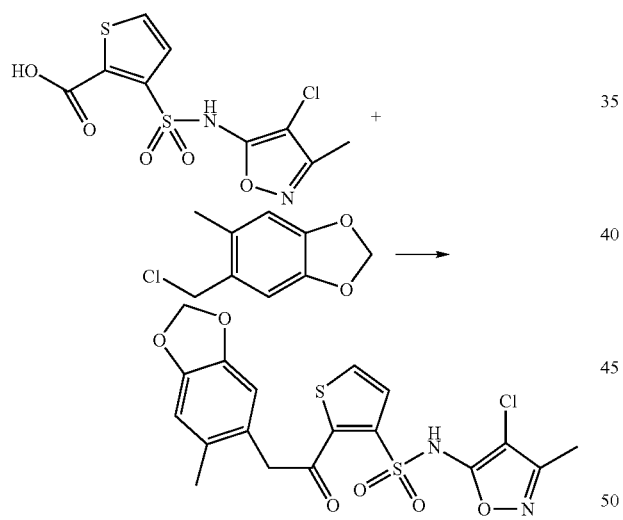

2-[2-(6-Methyl-benzo[1,3]dioxol-5-yl)-acetyl]-thiophene-3-sulfonic acid (4-chloro-3-methyl-isoxazol-5-yl)-amide: 1,1'-carbonyldiimidazole (600 mg) was added to a solution of 3-[(4-chloro-3-methyl-5-isoxazolyl)sulfamoyl]-2-thiophenecarboxylic acid (900 mg, 2.79 mmol) in anhydrous tetrahydrofuran (20 mL). The mixture was stirred at ambient temperature for about 15 minutes and then sequentially treated with imidazole (380 mg, 5.58 mmol) and N,O-dimethylhydroxylamine hydrochloride (420 mg, 4.3 mmol). Under continuous stirring, the mixture was maintained at ambient temperature for about 4 hours. The solvent was removed in vacuo and the residue was partitioned between ethyl acetate (100 mL) and 1 N hydrochloric acid (30 mL). The organic layer was dried over anhydrous magnesium sulfate, filtered and concentrated. The resulting residue was treated with toluene and re-concentrated. The resulting red oil was dissolved in anhydrous tetrahydrofuran (20 mL), cooled to about 0° C., and then treated with a Grignard reagent prepared from 5-chloromethyl-6-methyl-benzo[1,3]dioxole (800 mg, 4.36 mmol) and magnesium turnings (826 mg, 34.4 mmol) in tetrahydrofuran (50 mL). Under continuous stirring, the mixture was maintained at about 0° C. for about 1 hour and then at ambient temperature for about 2 hours. At about 0° C., the reaction mixture was quenched with a mixture of concentrated hydrochloric acid (20 mL) and methanol (50 mL). The mixture was stirred at about 0° C. for about 10 minutes, and then concentrated in vacuo. The aqueous residue was partitioned between ethyl acetate (100 mL) and 1 N hydrochloric acid (30 mL). The crude product was isolated using standard extractive work up and purified by prep-TLC (eluted with CH$_2$Cl$_2$:MeOH=7:1) to give 2-[2-(6-methyl-benzo[1,3]dioxol-5-yl)-acetyl]-thiophene-3-sulfonic acid (4-chloro-3-methyl-isoxazol-5-yl) amide (150 mg, 30%) as a yellow solid. $^1$H NMR (300 MHz, CD$_3$OD) δ 7.77 (d, J=5.1 Hz, 1H), 7.40 (d, J=5.1 Hz, 1H), 6.74 (d, J=4.2 Hz, 2H), 5.94 (s, 3H), 4.76 (s, 2H), 2.04 (s, 3H), 1.99 (s, 3H); ESI-MS: m/z=455 (MH)$^+$; HPLC purity: 95%.

Example 2 d$_2$-2-[2-(6-Methyl-benzo[1,3]dioxol-5-yl)-acetyl]-thiophene-3-sulfonic acid (4-chloro-3-methyl-isoxazol-5-yl)-amide

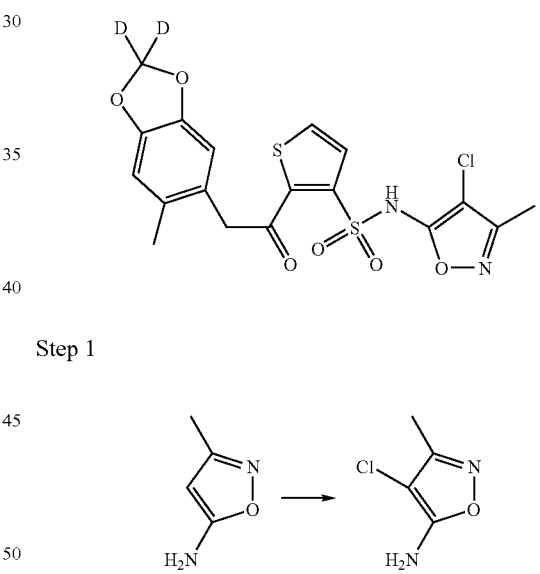

Step 1

5-amino-4-chloro-3-methylisoxazole: The title compound was made by following the procedure set forth in Example 1, step 1.

Step 2

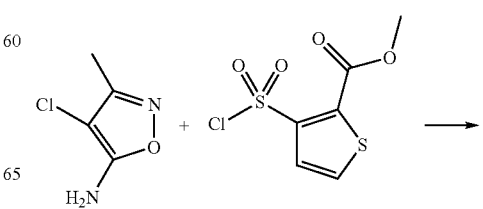

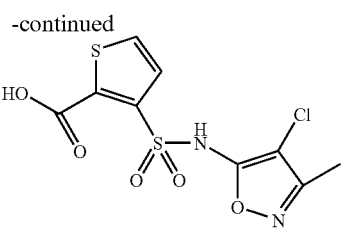

3-(4-Chloro-3-methyl-isoxazol-5-ylsulfamoyl)-thiophene-2-carboxylic acid: The title compound was made by following the procedure set forth in Example 1, step 2.

Step 3

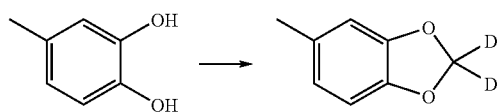

$d_2$-5-Methyl-benzo[1,3]-dioxole: 4-methylcatechol (5 g, 40.3 mmol) was added to a suspension of cesium carbonate (20 g, 61 mmol) in dimethylformamide (60 mL). The mixture was put under vacuum and purged with nitrogen three times. $d_2$-Dichloromethane (3.7 g, 61 mmol) was then added at ambient temperature, and the mixture was heated at about 110° C. for about 2 hours. After cooling to ambient temperature, the reaction mixture was partitioned between water (400 mL) and ether-pentane (1:1 ratio, 600 mL). The organic layer was extracted, washed with water (3×200 mL), dried over anhydrous magnesium sulfate, filtered and concentrated in vacuo to afford the desired product (2 g, 37%). $^1$H NMR (300 MHz, CDCl$_3$) δ 6.71-6.59 (m, 3H), 2.27 (s, 3H).

Step 4

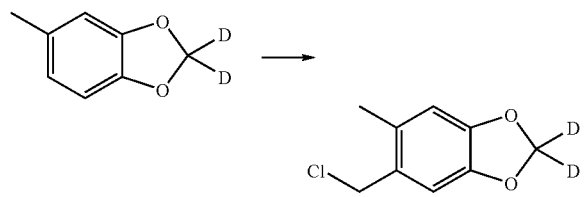

$d_2$-5-(Chloromethyl)-6-methylbenzo[d][1,3]-dioxole: At about 0° C., $d_2$-5-Methylbenzo[d][1,3]dioxole (2 g, 14.5 mmol) and formaldehyde (37% in water, 4 mL) were sequentially added to a mixture of dichloromethane (26 mL), tetrabutylammonium bromide (320 mg) and concentrated hydrochloric acid (26 mL). Under continuos stirring, the mixture was maintained at about 0° C. for about 1 hour and then at ambient temperature for 4 hours. After standard extractive workup, the resulting solid residue was heated with hexanes (100 mL) and the insolubles were removed by filtration. The filtrate was concentrated in vacuo to give desired product (2 g, 74%). $^1$H NMR (300 MHz, CDCl$_3$) δ 6.80 (s, 1H), 6.67 (s, 1H), 4.54 (s, 2H), 2.33 (s, 3H); GC-MS: m/z=184 (MH)$^+$.

Step 5

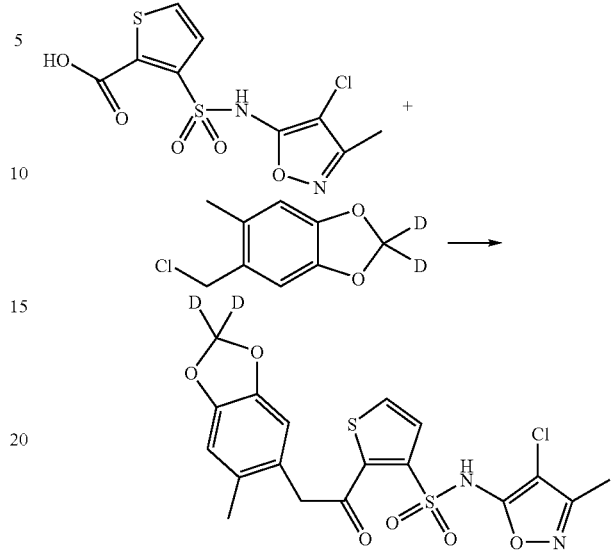

$d_2$-2-[2-(6-Methyl-benzo[1,3]dioxol-5-yl)-acetyl]-thiophene-3-sulfonic acid (4-chloro-3-methyl-isoxazol-5-yl)-amide: 1,1'-carbonyldiimidazole (250 mg) was added to a solution of 3-[(4-chloro-3-methyl-5-isoxazolyl)sulfamoyl]-2-thiophenecarboxylic acid (400 mg, 10.1 mmol) in anhydrous tetrahydrofuran (20 mL). The resulting mixture was stirred at ambient temperature for about 15 minutes and then sequentially treated with imidazole (168 mg, 2.5 mmol) and N,O-dimethylhydroxylamine hydrochloride (184 mg, 1.89 mmol). Under continuous stirring, the mixture was maintained at ambient temperature for about 4 hours. The solvent was removed in vacuo and the residue was partitioned between ethyl acetate (100 mL) and 1 N hydrochloric acid (30 mL). The organic layer was extracted, dried over anhydrous magnesium sulfate, filtered, and concentrated. The residue was treated with toluene (30 mL) and re-concentrated. The resulting red oil was dissolved in anhydrous tetrahydrofuran (20 mL), cooled to about 0° C. in an ice-bath, and treated with a Grignard reagent prepared from $d_2$-5-chloromethyl-6-methyl-benzo[1,3]dioxole (800 mg, 4.29 mmol) and magnesium turnings (826 mg, 34.4 mmol) in tetrahydrofuran (50 mL). Under continuous stirring, the mixture was maintained at about 0° C. for about 1 hour and then at ambient temperature for about 2 hours. At about 0° C., the reaction mixture was quenched with a mixture of concentrated hydrochloric acid (20 mL) and methanol (50 mL). After continuous stirring at about 0° C. for about 10 minutes, the reaction mixture was concentrated in vacuo. The aqueous residue was partitioned between ethyl acetate (100 mL) and 1 N hydrochloric acid (30 mL). The crude product was isolated using standard extractive work up and purified by prep-TLC (eluted with CH$_2$Cl$_2$: MeOH=7:1) to give $d_2$-2-[2-(6-methyl-benzo[1,3]dioxol-5-yl)-acetyl]-thiophene-3-sulfonic acid (4-chloro-3-methyl-isoxazol-5-yl) amide (120 mg, 24%) as a yellow solid. $^1$H NMR (300 MHz, CD$_3$OD) δ 7.75 (d, J=5.1 Hz, 1H), 7.40 (d, J=5.1 Hz, 1H), 6.72 (d, J=3.9 Hz, 2H), 4.76 (s, 2H), 2.04 (s, 3H), 1.99 (s, 3H); ESI-MS: m/z=457 (MH)$^+$; HPLC purity: 95%.

Example 3 d₃-2-[2-(6-Methyl-benzo[1,3]dioxol-5-yl)-acetyl]-thiophene-3-sulfonic acid (4-chloro-3-methyl-isoxazol-5-yl)-amide

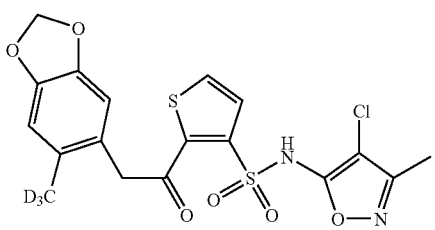

Step 1

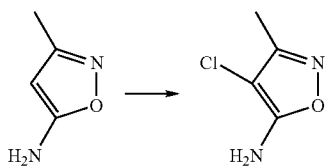

5-amino-4-chloro-3-methylisoxazole: The title compound was made by following the procedure set forth in Example 1, step 1.

Step 2

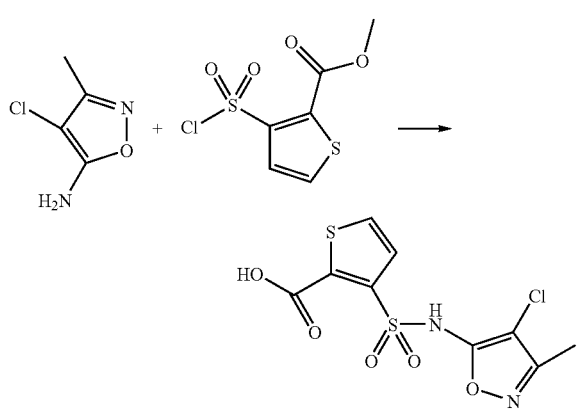

3-(4-Chloro-3-methyl-isoxazol-5-ylsulfamoyl)-thiophene-2-carboxylic acid: The title compound was made by following the procedure set forth in Example 1, step 2.

Step 3

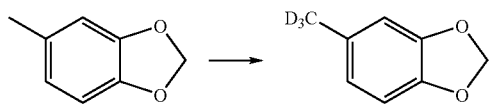

d₃-5-Methyl-benzo[1,3]dioxole: A mixture of 5-methyl-benzo[d][1,3]dioxole (1.25 g, 9.2 mmol), 10% palladium on carbon (251 mg), sodium formate (376 mg) and deuterium oxide (5 mL) was heated at about 135° C. for about 48 hours. The mixture was cooled to ambient temperature, extracted with pentane (3×50 mL), and the solvent removed in vacuo to afford the product d₃-5-methyl-benzo[1,3]dioxole (1.0 g, 80%). ¹H NMR (300 MHz, CDCl₃) δ 6.72-6.60 (m, 3H), 5.90 (s, 2H).

Step 4

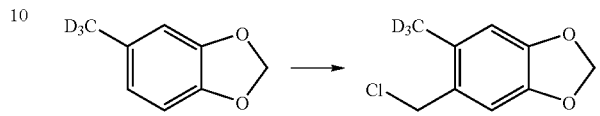

d₃-5-(Chloromethyl)-6-methylbenzo[d][1,3]dioxole: At about 0° C., d₃-5-methylbenzo[d][1,3]dioxole (900 mg, 6.47 mmol) and formaldehyde (37% in water, 1.5 mL) were sequentially added to a mixture of dichloromethane (13 mL), tetrabutylammonium bromide (160 mg) and concentrated hydrochloric acid (13 mL). Under continuous stirring, the resulting mixture was maintained at about 0° C. for about 1 hour and then at ambient temperature for about 4 hours. The mixture was diluted with ether (100 mL). After standard extractive workup, the solid residue was heated with hexanes (100 mL), and the insolubles were removed by filtration. The filtrate was concentrated in vacuo to give desired product (800 mg, 67%). ¹H NMR (300 MHz, CDCl₃) δ 6.80 (s, 1H), 6.70 (s, 1H), 5.94 (s, 3H), 4.57 (s, 2H).

Step 5

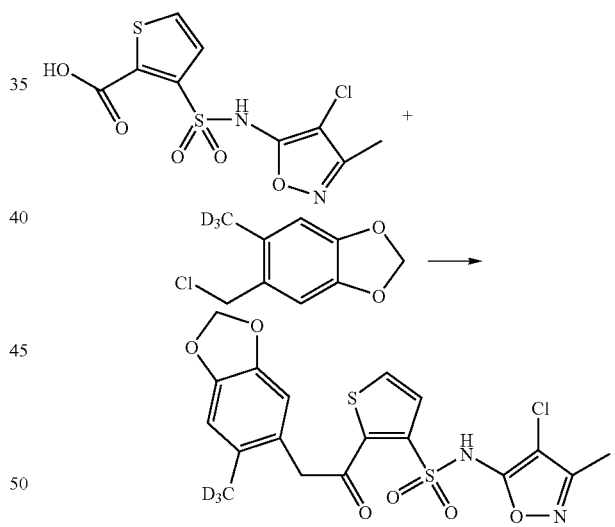

d₃-2-[2-(6-Methyl-benzo[1,3]dioxol-5-yl)-acetyl]-thiophene-3-sulfonic acid (4-chloro-3-methyl-isoxazol-5-yl)-amide: 1,1'-carbonyldiimidazole (250 mg) was added to a solution of 3-[(4-chloro-3-methyl-5-isoxazolyl)sulfamoyl]-2-thiophenecarboxylic acid (400 mg, 10.1 mmol) in anhydrous tetrahydrofuran (20 mL). Under continuous stirring, the mixture was maintained at ambient temperature for about 15 minutes, imidazole (168 mg, 2.5 mmol) and N,O-dimethylhydroxylamine hydrochloride (184 mg, 1.89 mmol) were sequentially added, and the mixture was maintained at ambient temperature for about 4 hours. The solvent was removed in vacuo and the residue was partitioned between ethyl acetate (100 mL) and 1 N hydrochloric acid (30 mL). The organic layer was separated and dried over anhydrous magnesium sulfate, filtered and concentrated. The residue was treated with toluene (20 mL) and re-concentrated. The resulting red oil was dissolved in anhydrous tetrahydrofuran (20 mL), cooled to about 0° C., and treated with a Grignard reagent prepared from $d_3$-5-chloromethyl-6-methyl-benzo[1,3]dioxole (800 mg, 4.29 mmol) and magnesium turnings (826 mg, 34.4 mmol) in tetrahydrofuran (50 mL). Under continuous stirring, the reaction mixture was maintained at about 0° C. for about 1 hour, and then at ambient temperature for about 2 hours. At about 0° C., the reaction mixture was quenched with a mixture of concentrated hydrochloric acid (20 mL) and methanol (50 mL). After stirring at about 0° C. for about 10 minutes, the reaction mixture was concentrated in vacuo. The aqueous residue was partitioned between ethyl acetate (100 mL) and 1 N hydrochloric acid (30 mL). The crude product was isolated using standard extractive work up and purified by prep-TLC (eluted with $CH_2Cl_2$: MeOH=7:1) to give $d_3$-2-[2-(6-methyl-benzo[1,3]dioxol-5-yl)-acetyl]-thiophene-3-sulfonic acid (4-chloro-3-methyl-isoxazol-5-yl) amide (40 mg, 10%) as a yellow solid. $^1$H NMR (300 MHz, $CD_3OD$) δ 7.75 (d, J=5.4 Hz, 1H), 7.40 (d, J=5.1 Hz, 1H), 6.72 (d, J=4.2 Hz, 2H), 5.93 (s, 3H), 4.76 (s, 2H), 1.99 (s, 3H); ESI-MS: m/z=458(MH)$^+$; HPLC purity: 96%.

Example 4

$d_5$-2-[2-(6-Methyl-benzo[1,3]dioxol-5-yl)-acetyl]-thiophene-3-sulfonic acid (4-chloro-3-methyl-isoxazol-5-yl)-amide

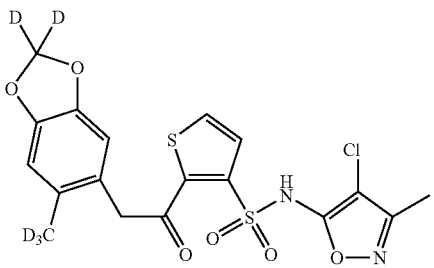

Step 1

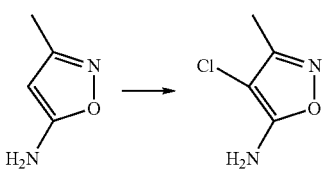

5-amino-4-chloro-3-methylisoxazole: The title compound was made by following the procedure set forth in Example 1, step 1.

Step 2

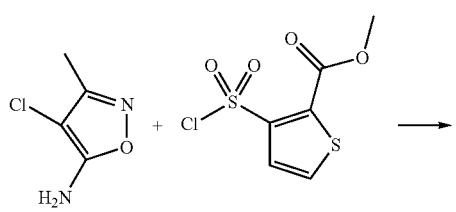

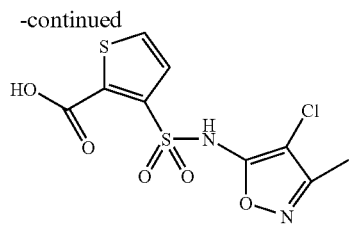

3-(4-Chloro-3-methyl-isoxazol-5-ylsulfamoyl)-thiophene-2-carboxylic acid: The title compound was made by following the procedure set forth in Example 1, step 2.

Step 3

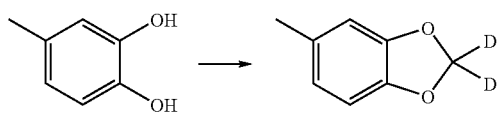

$d_2$-5-Methyl-benzo[1,3]dioxole: The title compound was made by following the procedure set forth in Example 2, step 3.

Step 4

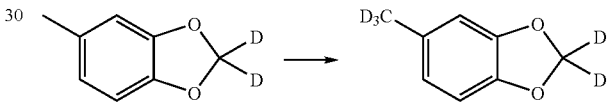

$d_5$-5-Methyl-benzo[1,3]dioxole: A mixture of $d_2$-5-methylbenzo[d]-[1,3]dioxole (2.2 g, 16.2 mmol), 10% palladium on carbon (500 mg), sodium formate (800 mg) and deuterium oxide (10 mL) was heated at about 135° C. for about 48 hours. The reaction mixture was cooled to ambient temperature, extracted with pentane (3×50 mL), and the solvent was removed in vacuo to afford the product $d_5$-5-methyl-benzo[1,3]dioxole (800 mg, 30%), which was used directly in next reaction without further purification.

Step 5

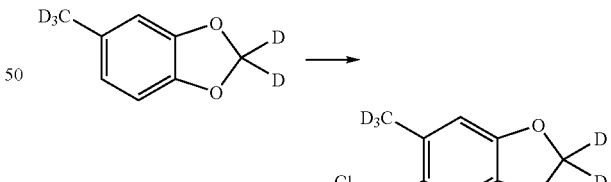

$d_5$-5-(Chloromethyl)-6-methylbenzo[d][1,3]dioxole: At about 0° C., $d_5$-5-methylbenzo[d]-[1,3]dioxole (800 mg, 5.67 mmol) and formaldehyde (37% in water, 0.5 mL) were sequentially added to a mixture of dichloromethane (5 mL), tetrabutylammonium bromide (120 mg) and concentrated hydrochloric acid (5 mL). Under continuous stirring, the resulting mixture was maintained at about 0° C. for about 1 hour and then at ambient temperature for about 4 hours. The reaction mixture was diluted with ether (100 mL). After standard extractive workup the resulting solid was heated with hexanes (100 mL), and the insolubles were removed by filtration. The filtrate was concentrated in vacuo to give desired product (780 mg, 76%). $^1$H NMR (300 MHz, CDCl$_3$) δ 6.78 (s, 1H), 6.66 (s, 1H), 4.57 (s, 2H).

Step 6

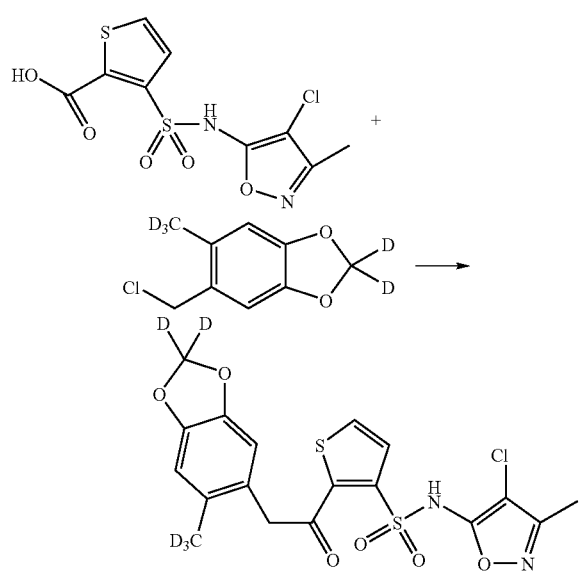

$d_5$-2-[2-(6-Methyl-benzo[1,3]-dioxol-5-yl)-acetyl]-thiophene-3-sulfonic acid (4-chloro-3-methyl-isoxazol-5-yl)-amide: 1,1'-carbonyldiimidazole (18.8 mg) was added to a solution of 3-[(4-chloro-3-methyl-5-isoxazolyl)sulfamoyl]-2-thiophenecarboxylic acid (300 mg, 7.5 mmol) in anhydrous tetrahydrofuran (20 mL). Under continuous stirring, the mixture was maintained at ambient temperature for about 15 minutes, imidazole (126 mg, 18.8 mmol) and N,O-dimethylhydroxylamine hydrochloride (138 mg, 1.42 mmol) were sequentially added, and the mixture was maintained at ambient temperature for about 4 hours. The solvent was removed in vacuo and the residue was partitioned between ethyl acetate (100 mL) and 1 N hydrochloric acid (30 mL). The organic layer was dried over anhydrous magnesium sulfate, filtered and concentrated. The residue was treated with toluene and re-concentrated. The resulting red oil was dissolved in anhydrous tetrahydrofuran (20 mL), cooled to about 0° C. and treated with a Grignard reagent prepared from $d_5$-5-chloromethyl-6-methyl-benzo[1,3]dioxole (750 mg, 3.97 mmol) and magnesium turnings (800 mg, 32 mmol) in tetrahydrofuran (50 mL). Under continuous stirring, the reaction mixture was maintained at about 0° C. for about 1 hour, and then at ambient temperature for about 2 hours. At about 0° C., the reaction mixture was quenched with a mixture of concentrated hydrochloric acid (20 mL) and methanol (50 mL). After stirring at about 0° C. for about 10 minutes, the reaction mixture was concentrated in vacuo. The aqueous residue was partitioned between ethyl acetate (100 mL) and 1 N hydrochloric acid (30 mL). The crude product was isolated using standard extractive work up and purified by prep-TLC (eluted with CH$_2$Cl$_2$:MeOH=7:1) to give $d_5$-2-[2-(6-methyl-benzo[1,3]dioxol-5-yl)-acetyl]-thiophene-3-sulfonic acid (4-chloro-3-methyl-isoxazol-5-yl) amide (90 mg, 25%) as a yellow solid. $^1$H NMR (300 MHz, CD$_3$OD) δ 7.75 (d, J=5.4 Hz, 1H), 7.40 (d, J=5.1 Hz, 1H), 6.72 (d, J=4.2 Hz, 2H), 4.76 (s, 2H), 1.99 (s, 3H); ESI-MS: m/z=460 (MH)$^+$; HPLC purity: 98%.

Example 6

$d_{11}$-2-[2-(6-Methyl-benzo[1,3]dioxol-5-yl)-acetyl]-thiophene-3-sulfonic acid (4-chloro-3-methyl isoxazol-5-yl)-amide

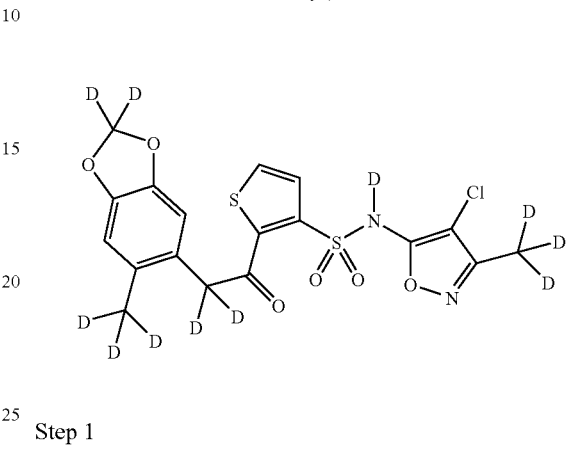

Step 1

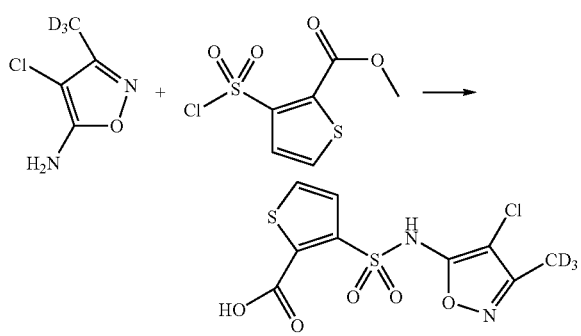

$d_3$-5-Amino-4-chloro-3-methylisoxazole: A mixture of 5-amino-4-chloro-3-methylisoxazole (10 mmol, Wako Pure Chemical Industries, Ltd. Jersey City, N.J.) and 10% palladium on carbon (240 mg) in deuterium oxide (40 mL) is degassed by bubbling a stream of nitrogen into the mixture for about 2 minutes. Sodium formate (400 mg) is added, the vessel is sealed and the reaction is heated to 80-160° C. for 5-48 hours. The mixture is cooled, extracted with ethyl acetate, dried and concentrated under reduced pressure to give the desired product $d_3$-5-amino-4-chloro-3-methylisoxazole.

Step 2

$d_3$-3-(4-Chloro-3-methyl-isoxazol-5-ylsulfamoyl)-thiophene-2-carboxylic acid: The procedure is carried out as in Wu et al., *Journal of Medicinal Chemistry* 1997, 40(11), 1682-1689. Sodium hydride (60% dispersion in mineral oil, 1.50 g, 37.4 mmol) is added to a solution of $d_3$-5-amino-4-chloro-3-methylisoxazole (17.7 mmol) in anhydrous tetrahydrofuran (60 mL) at about 0° C. The resulting mixture is stirred for about 10 minutes and 2-(methoxycarbonyl) thiophene-3-sulfonyl chloride (3.0 g, 12.5 mmol, Oakwood Products, Inc. West Columbia, S.C.) is added dropwise. The reaction is stirred at ambient temperature for about 4 hours, diluted with hexanes (60 mL), and the resulting precipitate is filtered and washed with hexanes. The precipitate is then dissolved in 1 N sodium hydroxide and stirred at ambient temperature for about 1 hour. After acidifying to pH ~2 with 2 N hydrochloric acid, the resulting precipitate is filtered, washed with water, and dried under vacuum, to give the title compound as a yellow powder.

Step 3

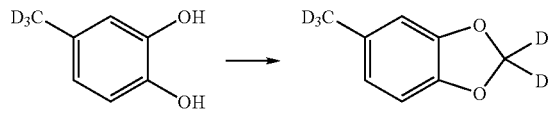

$d_3$-5-Methyl-benzo[1,3]dioxole: $d_3$-4-Methylcatechol (23.9 mmol, Cambridge Isotopes laboratories, Inc. Andover, Mass.) is added to a suspension of cesium carbonate (11.6 g, 35.6 mmol) in dimethylformamide (60 mL). The mixture is evacuated and flushed with nitrogen three times. $d_2$-Dichloromethane (2.29 mL, 26.3 mmol, 99.9% D) is added at ambient temperature, the reaction mixture is heated at about 110° C. for about 2 hours, cooled to ambient temperature, and partitioned between water and ether-pentane. The title product is isolated using standard extractive work up.

Step 4

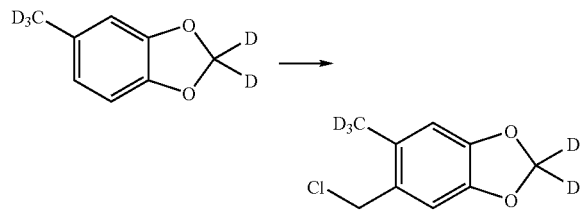

$d_5$-5-(Chloromethyl)-6-methylbenzo[d][1,3]dioxole: The procedure is carried out as in Wu et al., *Journal of Medicinal Chemistry* 1997, 40(11), 1690-1697. At about 0° C., $d_5$-5-Methylbenzo[d]-[1,3]dioxole (81 mmol) and formaldehyde (30% in water, 20 mL, 267 mmol) are sequentially added to a mixture of ether (100 mL) and concentrated hydrochloric acid (100 mL). Under continuous stirring, the mixture is maintained at about 0° C. for about 1 hour and then at ambient temperature for about 4 hours. The mixture is diluted with ether (100 mL). After standard extractive workup the solid residue is heated with hexanes (100 mL), and the insolubles are removed by filtration. The filtrate is concentrated to give a mixture of $d_5$-5-methylbenzo[d]-[1,3]dioxole and $d_5$-5-(chloromethyl)-6-methylbenzo-[d][1,3]dioxole (7:3) as a white solid.

Step 5

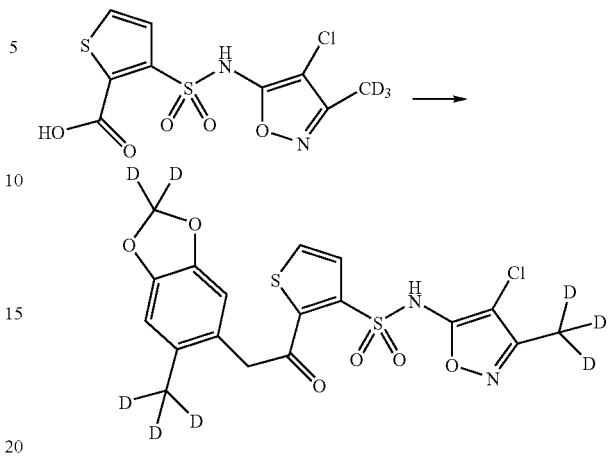

$d_8$-2-[2-(6-Methyl-benzo[1.3]dioxol-5-yl)-acetyl]-thiophene-3-sulfonic acid (4-chloro-3-methyl-isoxazol-5-yl)-amide: The procedure is carried out as in Wu et al., *Journal of Medicinal Chemistry* 1997, 40(11), 1690-1697. 1,1'-Carbonyldiimidazole (2.76 g, 17.04 mmol) is added to a solution of $d_3$-3-[(4-chloro-3-methyl-5-isoxazolyl)sulfamoyl]-2-thiophenecarboxylic acid (15.49 mmol) in anhydrous tetrahydrofuran (70 mL). The mixture is stirred at ambient temperature for about 15 minutes before imidazole (2.11 g, 30.98 mmol) and N,O-dimethylhydroxylamine hydrochloride (2.31 g, 23.24 mmol) are sequentially added. Under continuous stirring, the mixture is maintained at ambient temperature for about 4 hours, the solvent is removed in vacuo, and the residue is partitioned between ethyl acetate and 1 N hydrochloric acid. The organic layer is dried over magnesium sulfate and concentrated. The residue is treated with toluene and re-concentrated. The resulting red oil is dissolved in dry tetrahydrofuran (20 mL) and treated at about 0° C. with a Grignard reagent prepared from $d_5$-5-chloromethyl-6-methyl-benzo[1,3]dioxole (82.02 mmol) and magnesium turnings (2.3 g, 95.69 mmol) in tetrahydrofuran (100 mL). Under continuous stirring, the mixture is maintained at about 0° C. for about 1 hour, and then at ambient temperature for about 2 hours. While cooling, the reaction is quenched with a mixture of concentrated hydrochloric acid (20 mL) and methanol (50 mL). The mixture is stirred at about 0° C. for about 10 minutes, and then concentrated. The aqueous residue is partitioned between ethyl acetate and 1 N hydrochloric acid. The crude product is isolated using standard extractive work up and purified by preparative HPLC to affored the title compound as a yellow solid.

Step 6

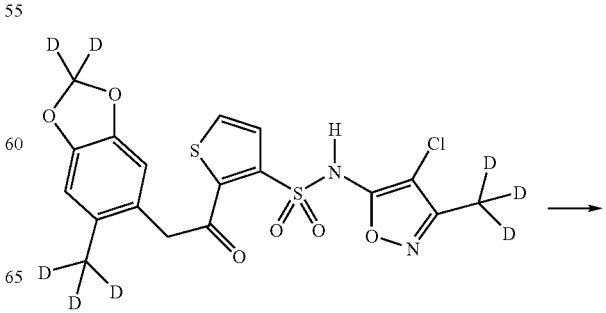

-continued

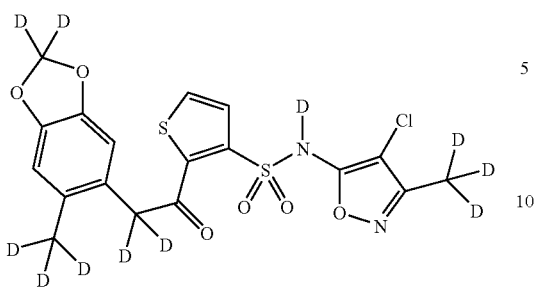

d₁₁-2-[2-(6-Methyl-benzo[1.3]dioxol-5-yl)-acetyl]-thiophene-3-sulfonic acid (4-chloro-3-methyl-isoxazol-5-yl)-amide: d₈-2-[2-(6-Methyl-benzo[1,3]dioxol-5-yl)-acetyl]-thiophene-3-sulfonic acid (4-chloro-3-methyl-isoxazol-5-yl)-amide (0.014 mmol) is taken up in 0.5 ml of d₄-methanol and added dropwise to a 0.1M solution of sodium carbonate in deuterium oxide (pH=11.4). Under continuous stirring, the solution is maintained at ambient temperature for 1-96 hours, diluted with ethyl acetate, washed with brine and dried over anhydrous magnesium sulfate. The solvent is removed in vacuo to yield the product d₁₁-2-[2-(6-methyl-benzo[1,3]dioxol-5-yl)-acetyl]-thiophene-3-sulfonic acid (4-chloro-3-methyl-isoxazol-5-yl)-amide.

Example 7 d₁₇-3-(3,4-Dimethyl-isoxazol-5-ylsulfamoyl)-thiophene-2-carboxylic acid (2-acetyl-4,6-dimethylphenyl)-amide

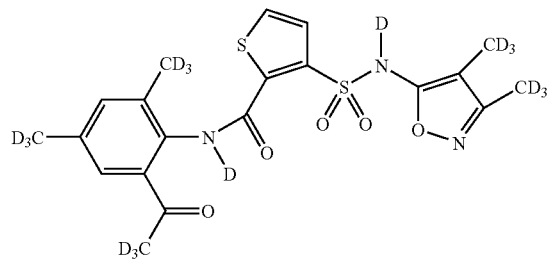

Step 1

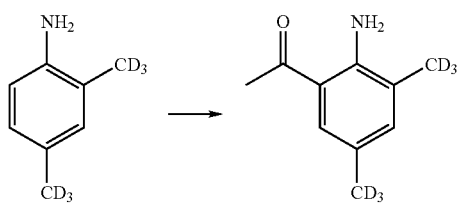

d₆-2-Amino-3,5-dimethylacetophenone: The procedure is carried out as in Wu et al., *Synth. Commun.* 1999, 29(20), 3509-3516. d₆-2,4-Dimethylaniline is available from C/D/N Isotopes Inc. (Pointe-Claire, Quebec).

Step 2

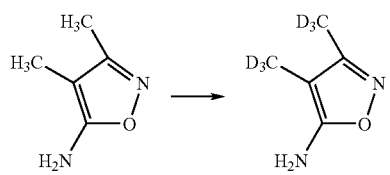

d₆-5-Amino-3,4-dimethylisoxazole: A mixture of 5-amino-3,4-dimethylisoxazole (10 mmol, Sigma-Aldrich) and 10% palladium on carbon (240 mg) in deuterium oxide (40 mL) is degassed by bubbling a stream of nitrogen into the mixture for about 2 minutes. Sodium formate (400 mg) is added, the vessel is sealed and the reaction is heated to 80-160° C. for 5-48 hours. The mixture is cooled, extracted with ethyl acetate, dried and concentrated under reduced pressure to give the desired product d₆-5-amino-3,4-dimethylisoxazole.

Step 3

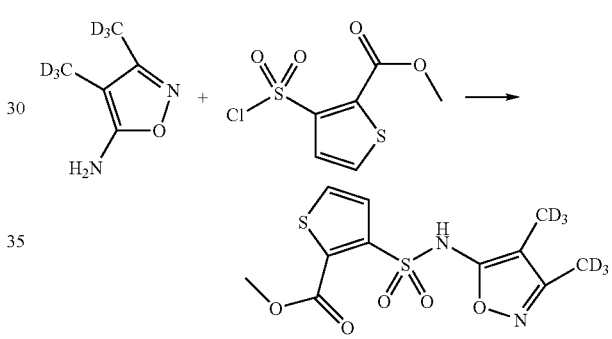

d₆-3-(3,4-Dimethyl-isoxazol-5-ylsulfamoyl)-thiophene-2-carboxylic acid methyl ester: The procedure is carried out as in Wu et al., *Journal of Medicinal Chemistry* 1997, 40(11), 1682-1689. Sodium hydride (60% dispersion in mineral oil, 1.50 g, 37.4 mmol) is added to a solution of d₃-5-amino-4-chloro-3-methylisoxazole (17.7 mmol) in anhydrous tetrahydrofuran (60 mL) at about 0° C. Under continuous stirring, the resulting mixture is maintained at about 0° C. for about 10 minutes, and 2-(methoxycarbonyl)thiophene-3-sulfonyl chloride (3.0 g, 12.5 mmol, Oakwood Products, Inc. West Columbia, S.C.) is added dropwise. Under continuous stirring, the reaction mixture is maintained at ambient temperature for about 4 hours, the mixture is diluted with hexanes (60 mL), the resulting precipitate is filtered and washed with hexanes, and dried in vacuo to give the title compound.

Step 4

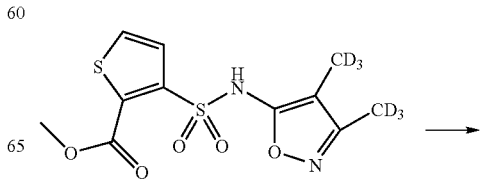

-continued

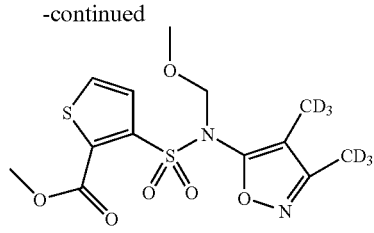

d$_6$-3-[(3,4-Dimethyl-isoxazol-5-yl)-methoxymethyl-sulfamoyl]-thiophene-2-carboxylic acid methyl ester: The procedure is carried out as in Wu et al., *Journal of Medicinal Chemistry* 1999, 42(22), 4485-4499. N,N-diisopropylethylamine (1.9 g, 15.0 mmol) and bromomethyl methyl ether (1.5 g, 12.0 mmol) are sequentially added to a solution of d$_6$-3-(3,4-dimethyl-isoxazol-5-ylsulfamoyl)-thiophene-2-carboxylic acid methyl ester (10.0 mmol) in anhydrous tetrahydrofuran (50 mL) at about 0° C. Under continuous stirring, the reaction is maintained at about 0° C. for about 2 hours, and then at ambient temperature for about 6 hours. Morpholine (0.87 g, 10.0 mmol) is added (to scavenge the excess bromomethyl methyl ether), and the mixture is maintained at ambient temperature and stirred for about hour. The mixture is concentrated, and the resulting residue is dissolved in ethyl acetate (200 mL) and washed with 1 N hydrochloric acid (2×150 mL). The organic layer is dried over magnesium sulfate and concentrated to give d$_6$-3-[(3,4-dimethyl-isoxazol-5-yl)-methoxymethyl-sulfamoyl]-thiophene-2-carboxylic acid methyl ester.

Step 5

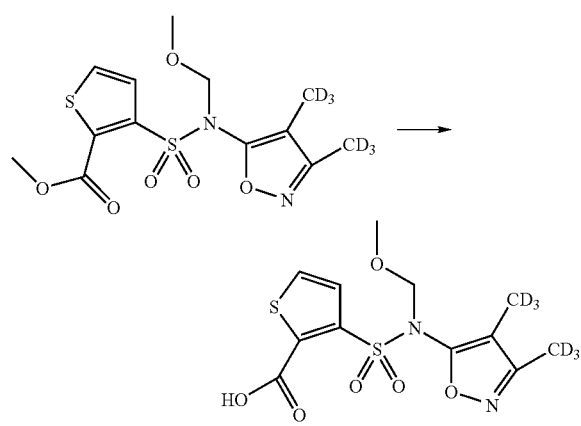

d$_6$-3-[(3,4-Dimethyl-isoxazol-5-yl)-methoxymethyl-sulfamoyl]-thiophene-2-carboxylic acid: The procedure is carried out as in Wu et al., *Journal of Medicinal Chemistry* 1999, 42(22), 4485-4499. 1 N sodium hydroxide (30 mL) is added to a solution of d$_6$-3-[(3,4-dimethyl-isoxazol-5-yl)-methoxymethyl-sulfamoyl]-thiophene-2-carboxylic acid methyl ester (7.8 mmol) in tetrahydrofuran (30 mL). Under continuous stirring, the resulting mixture is maintained at ambient temperature for about 3 hours, and then partitioned between 1 N hydrochloric acid (200 mL) and ethyl acetate (200 mL). The organic layer is dried with magnesium sulfate and concentrated to give the title compound.

Step 6

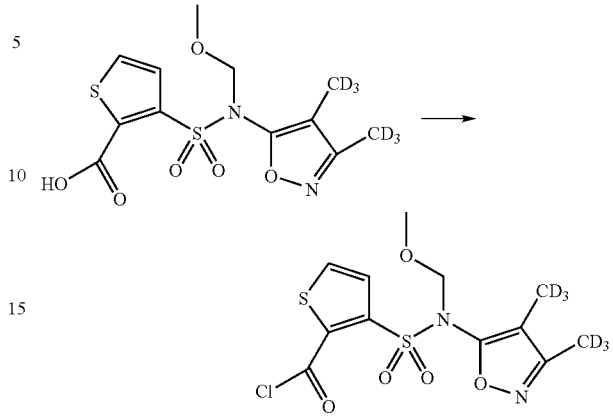

d$_6$-3-[(3,4-Dimethyl-isoxazol-5-yl)-methoxymethyl-sulfamoyl]-thiophene-2-carboxylic acid chloride: The procedure is carried out as in Wu et al, *Journal of Medicinal Chemistry* 1999, 42(22), 4485-4499. At 0° C., a catalytic amount of pyridine and oxalyl chloride (2 M in dichloromethane, 4.5 mL, 9.0 mmol) are sequentially added to a solution of d$_6$-3-[(3,4-dimethyl-isoxazol-5-yl)-methoxymethyl-sulfamoyl]-thiophene-2-carboxylic acid (4.1 mmol) in a mixture of tetrahydrofuran (10 mL) and chloroform (5 mL). Under continuous stirring, the mixture is maintained at ambient temperature for about 15 hours, and then concentrated in vacuo to afford the title compound.

Step 7

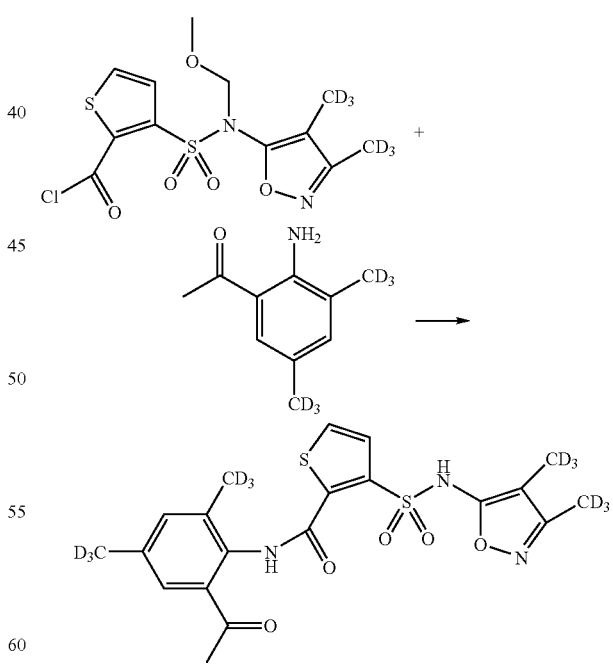

d$_{12}$-3-(3,4-Dimethyl-isoxazol-5-ylsulfamoyl)-thiophene-2-carboxylic acid (2-acetyl-4,6-dimethylphenyl)-amide: The procedure is carried out as in Wu et al., *Journal of Medicinal Chemistry* 1999, 42(22), 4485-4499. d$_6$-3-[(3,4-dimethyl-isoxazol-5-yl)-methoxymethyl-sulfamoyl]-thiophene-2-carboxylic acid chloride (2.54 mmol) is added to a solution of d₆-2-amino-3,5-dimethylacetophenone (10.15 mmol) in anhydrous tetrahydrofuran (30 mL). Under continuous stirring, the mixture is maintained at ambient temperature for about 15 hours, and then concentrated in vacuo. The resulting residue is partitioned between 1 N hydrochloric acid (200 mL) and ethyl acetate (200 mL). The organic layer is concentrated, the residue is dissolved in methanol (20 mL), and concentrated hydrochloric acid (10 mL) is added. The reaction is heated at about 70° C. for about 2 hours, cooled to ambient temperature, and then poured into iced water (250 mL). The resulting brown precipitate is collected by filtration, and then purified by reverse-phase HPLC to afford the title compound.

Step 8

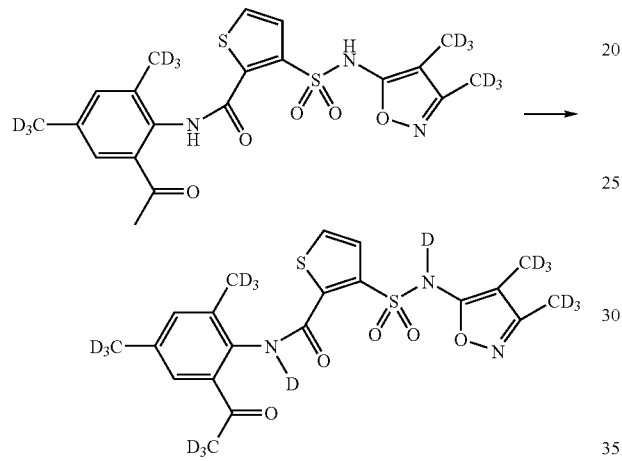

$d_{17}$-3-(3,4-Dimethyl-isoxazol-5-ylsulfamoyl)-thiophene-2-carboxylic acid (2-acetyl-4,6-dimethylphenyl)-amide: The procedure is carried out as in Example 6, step 6, but substituting $d_{12}$-3-(3,4-Dimethyl-isoxazol-5-ylsulfamoyl)-thiophene-2-carboxylic acid (2-acetyl-4,6-dimethylphenyl)-amide for $d_8$-2-[2-(6-Methyl-benzo[1,3]dioxol-5-yl)-acetyl]-thiophene-3-sulfonic acid (4-chloro-3-methyl-isoxazol-5-yl)-amide.

The following compounds can generally be made using the methods described above. It is expected that these compounds when made will have activity similar to those that have been made in the examples above.

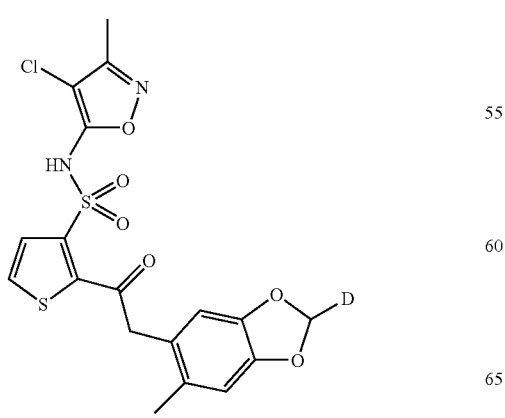

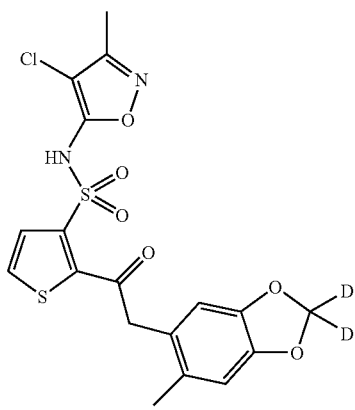

-continued

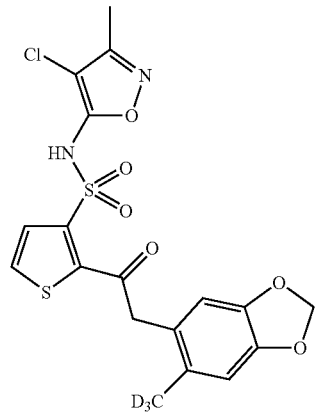

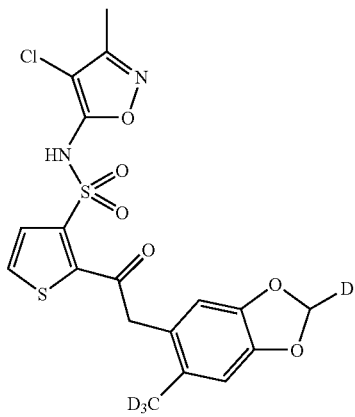

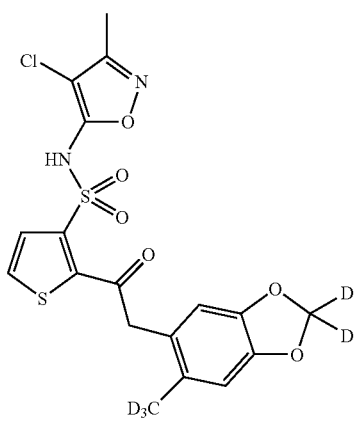

143
-continued
144
-continued
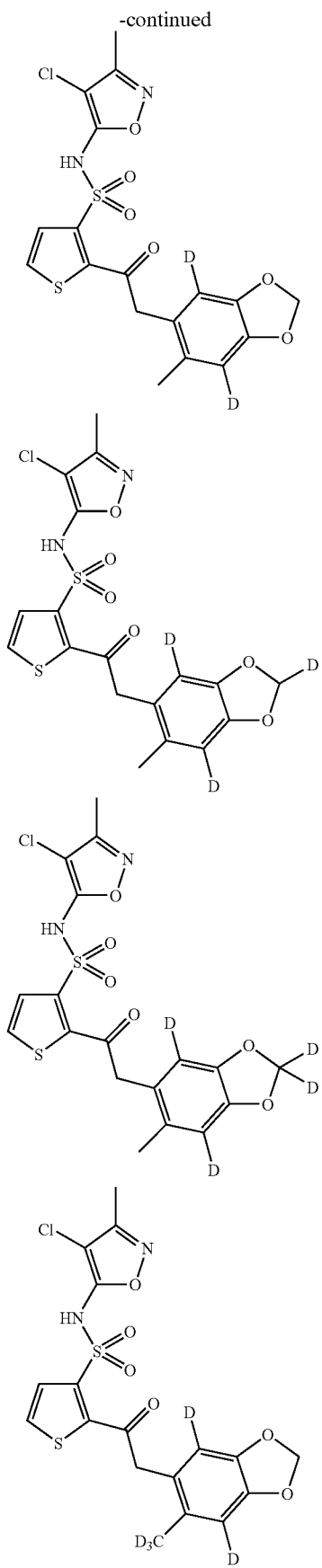
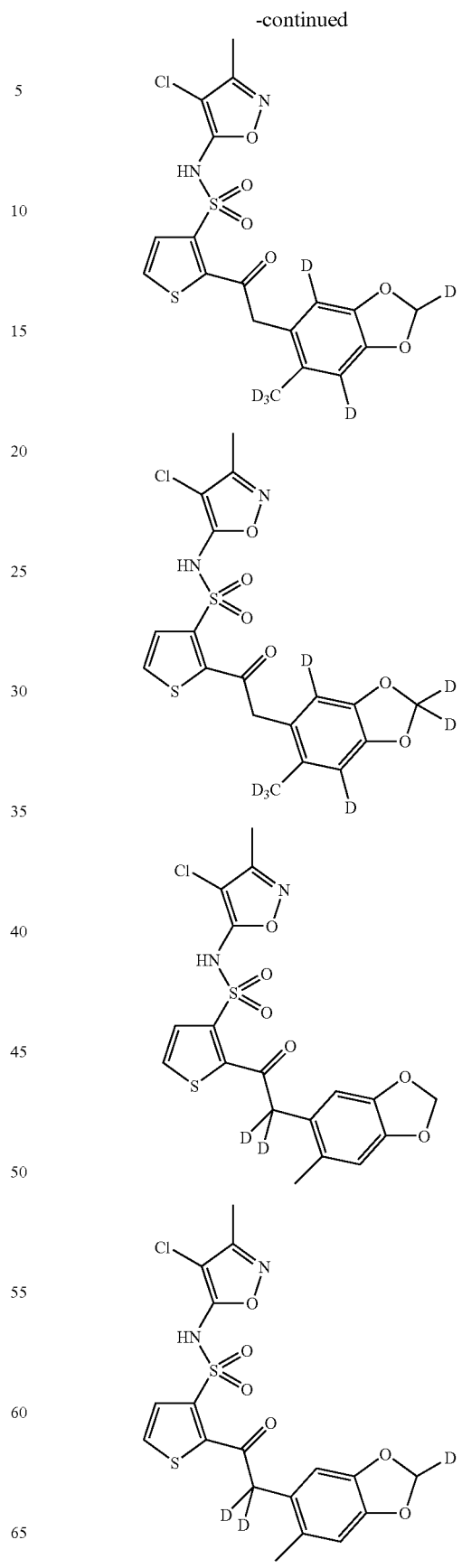

-continued
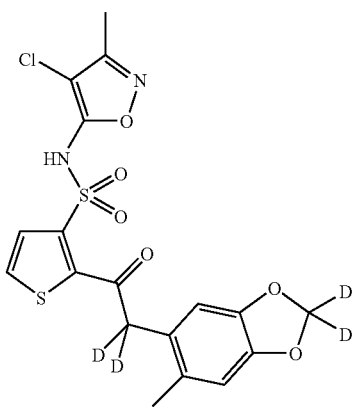
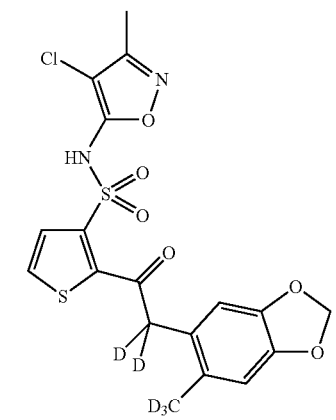
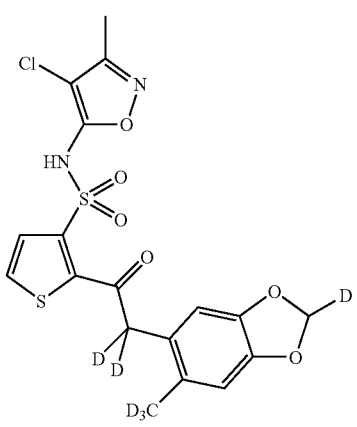
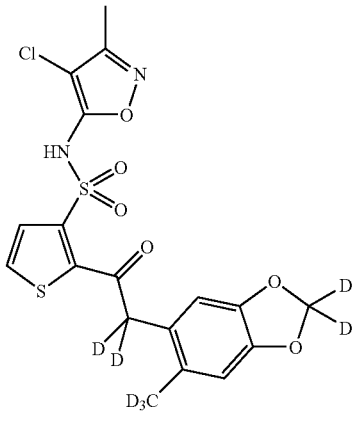
-continued
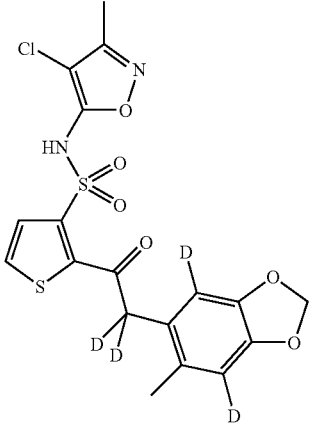
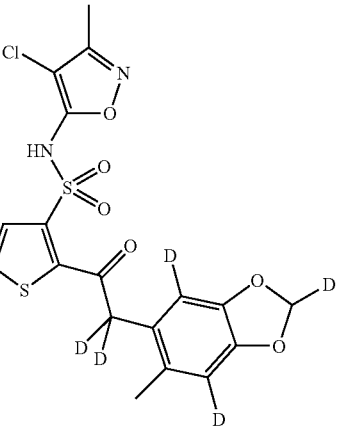
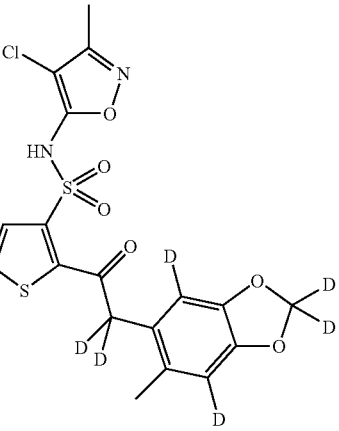
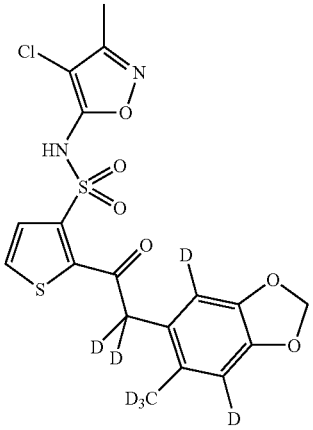

147
-continued
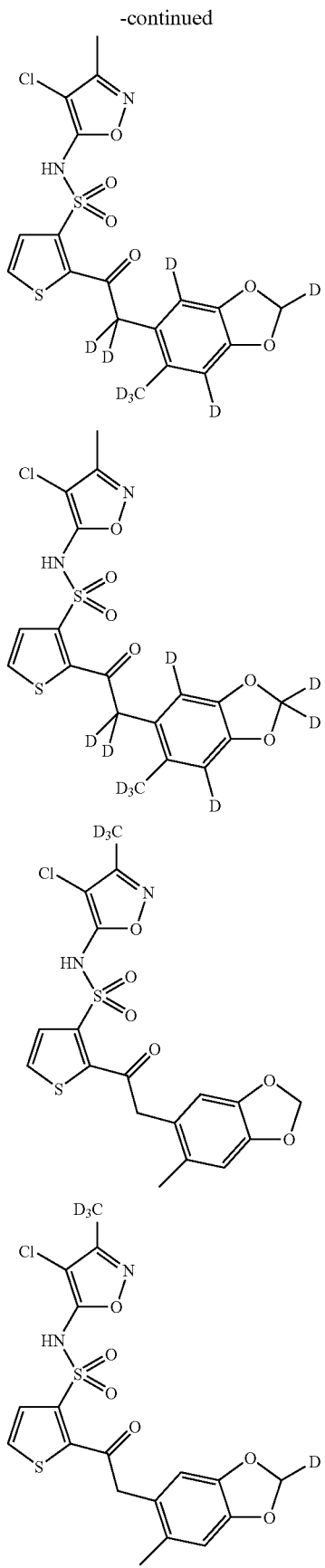
148
-continued
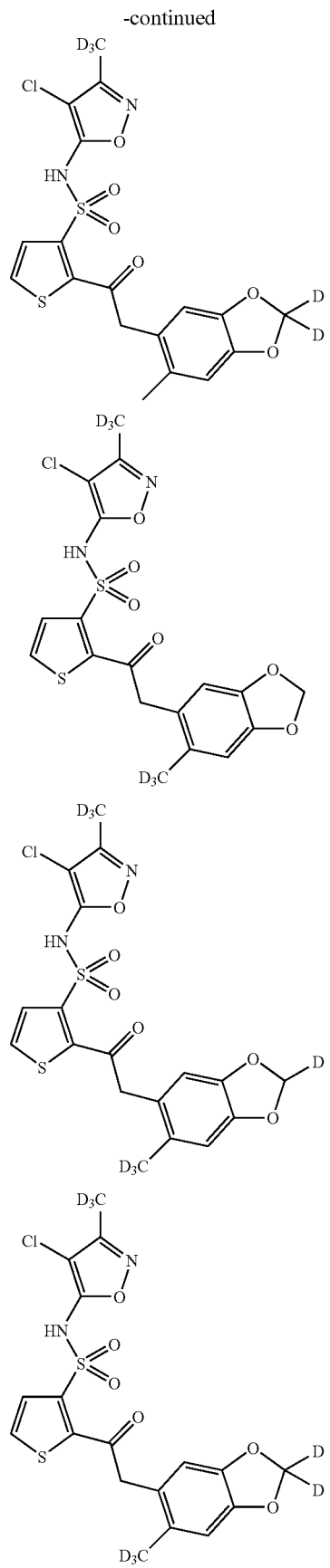

-continued
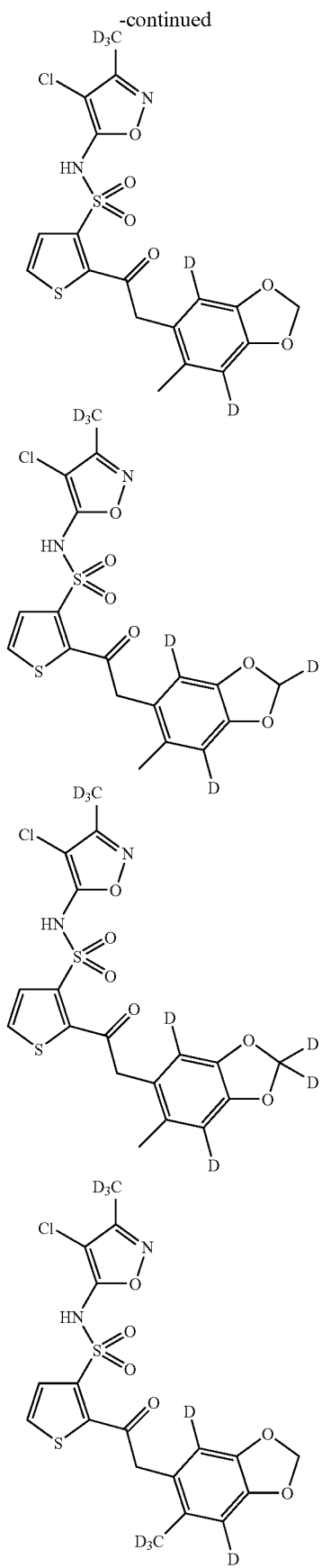
-continued
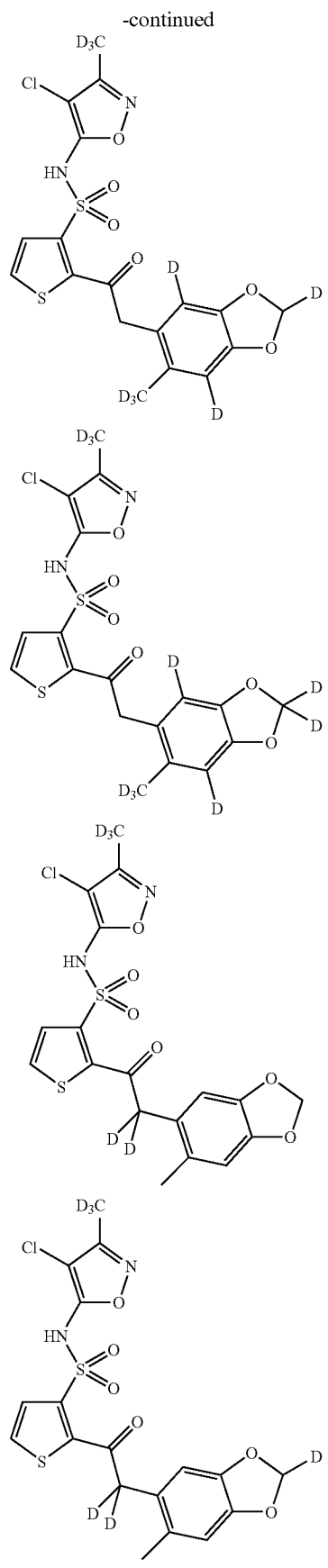

-continued
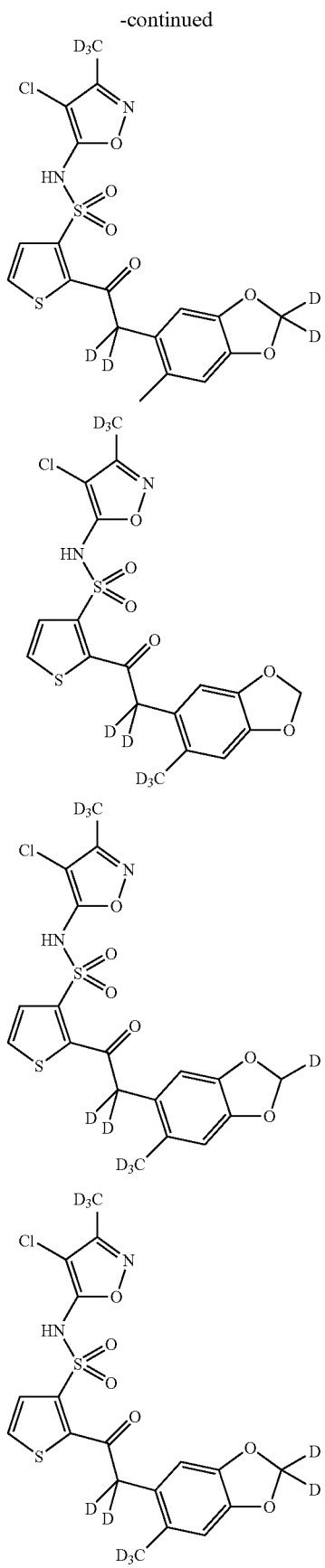
-continued
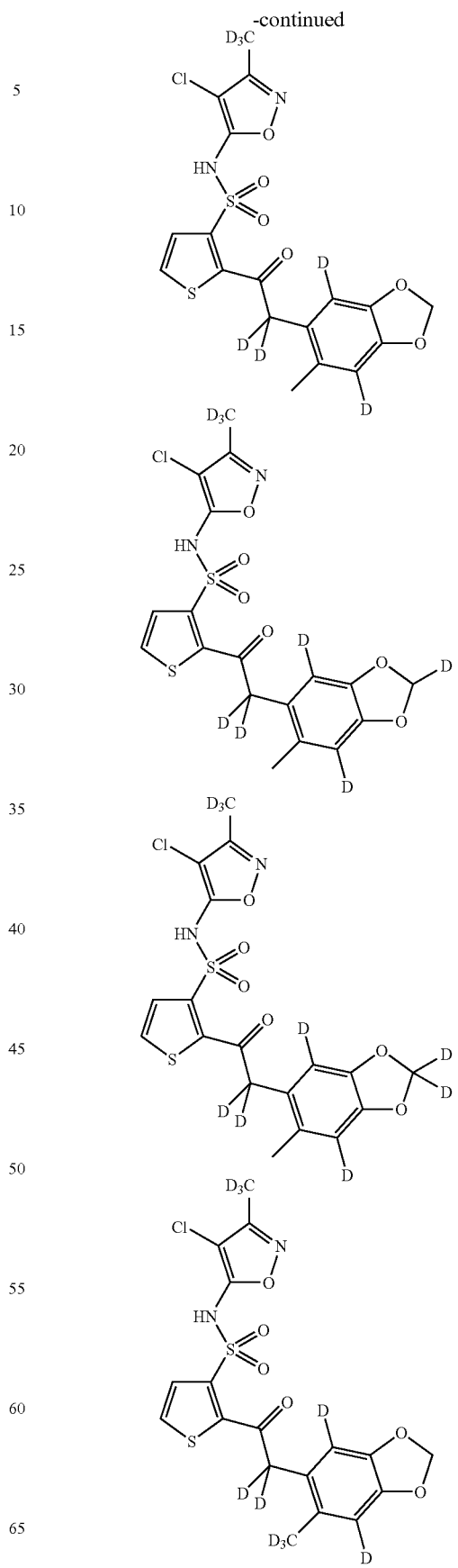

-continued
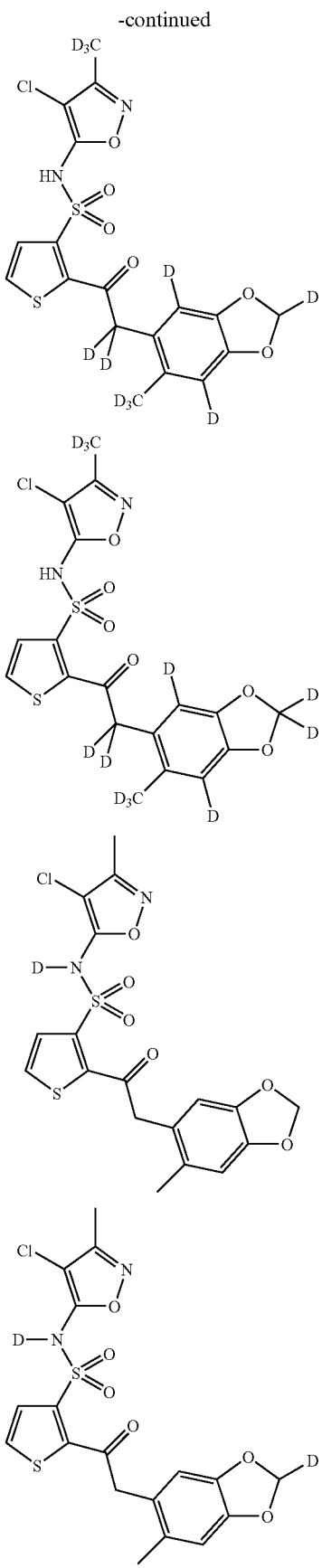
-continued
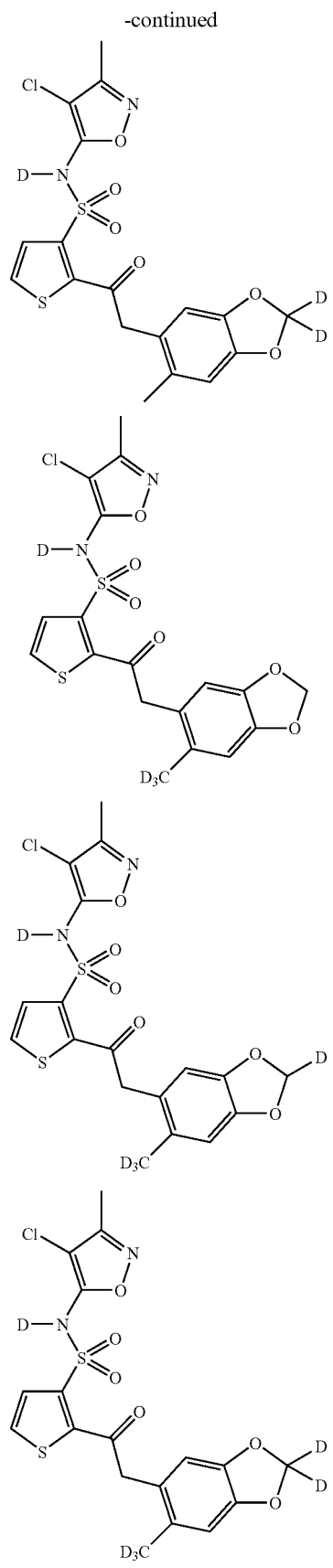

-continued
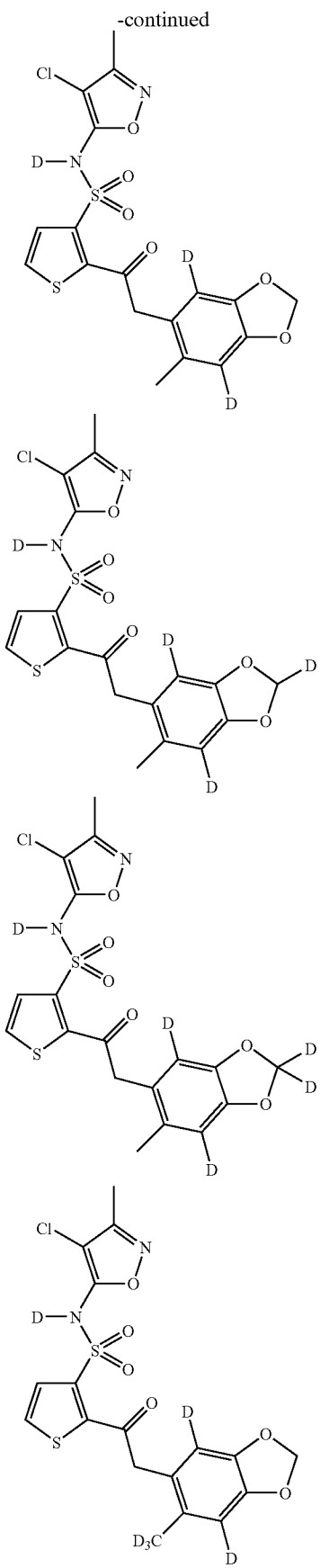
-continued
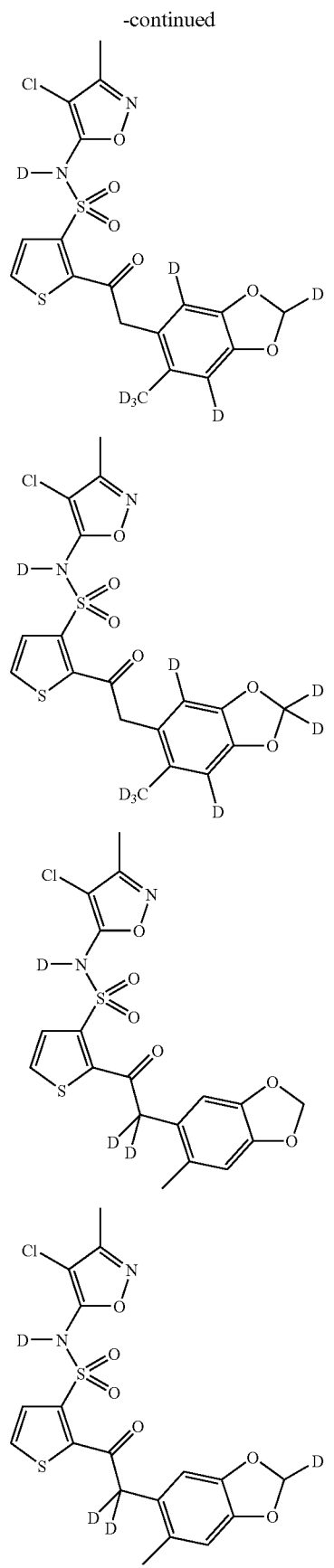

-continued
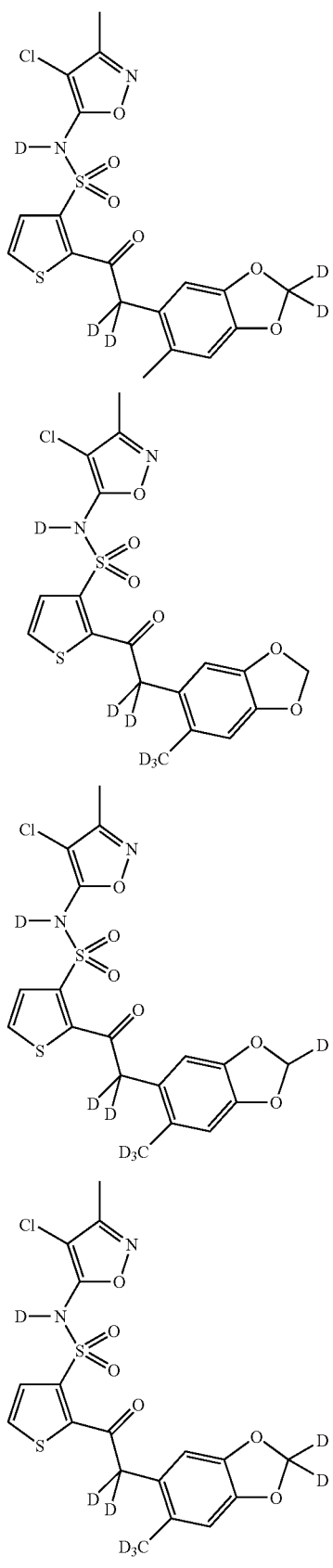
-continued
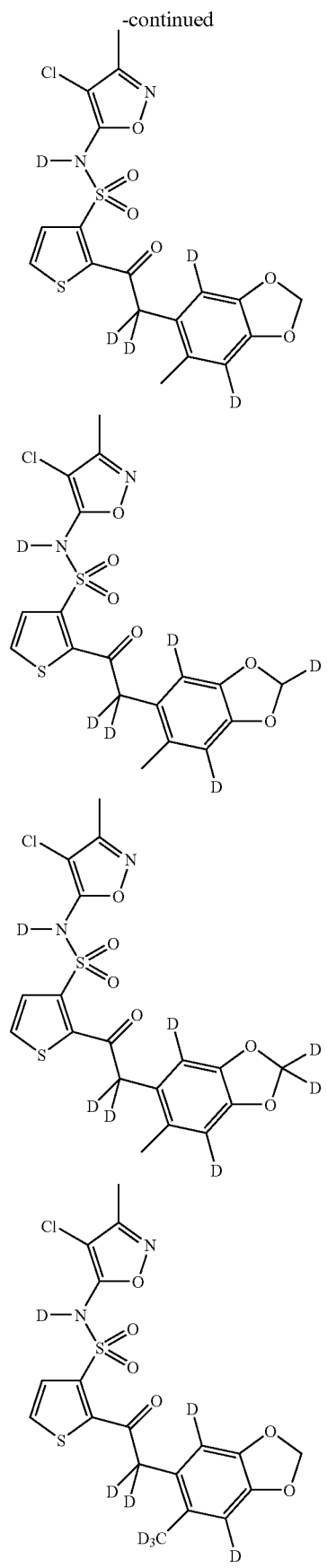

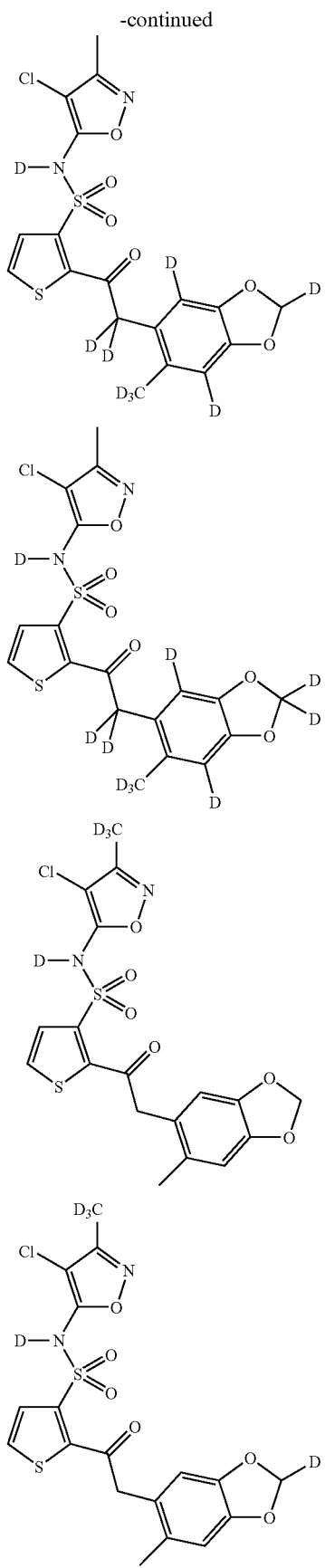
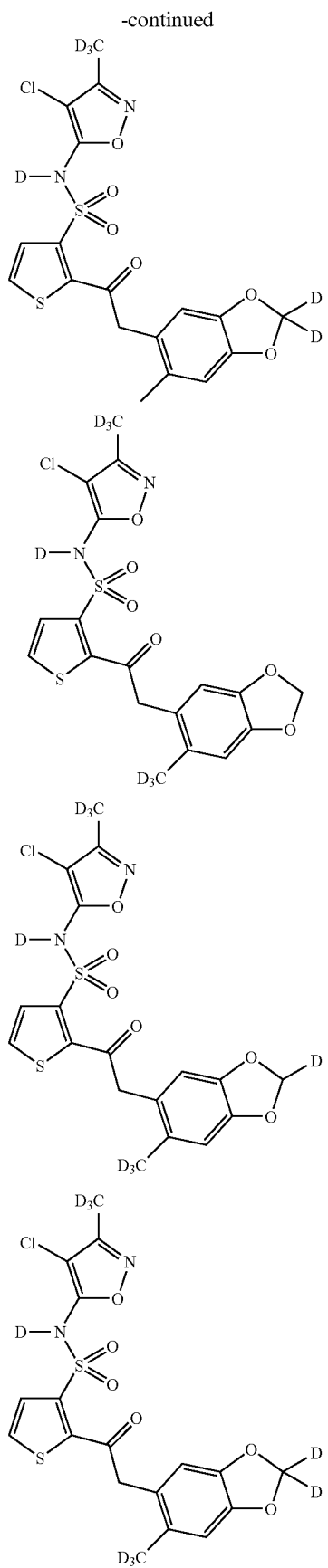

161
-continued
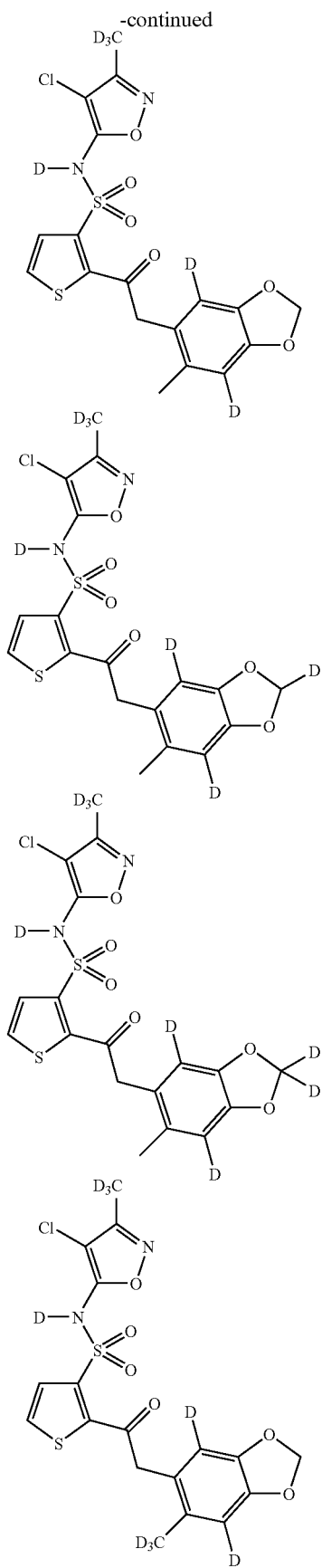
162
-continued
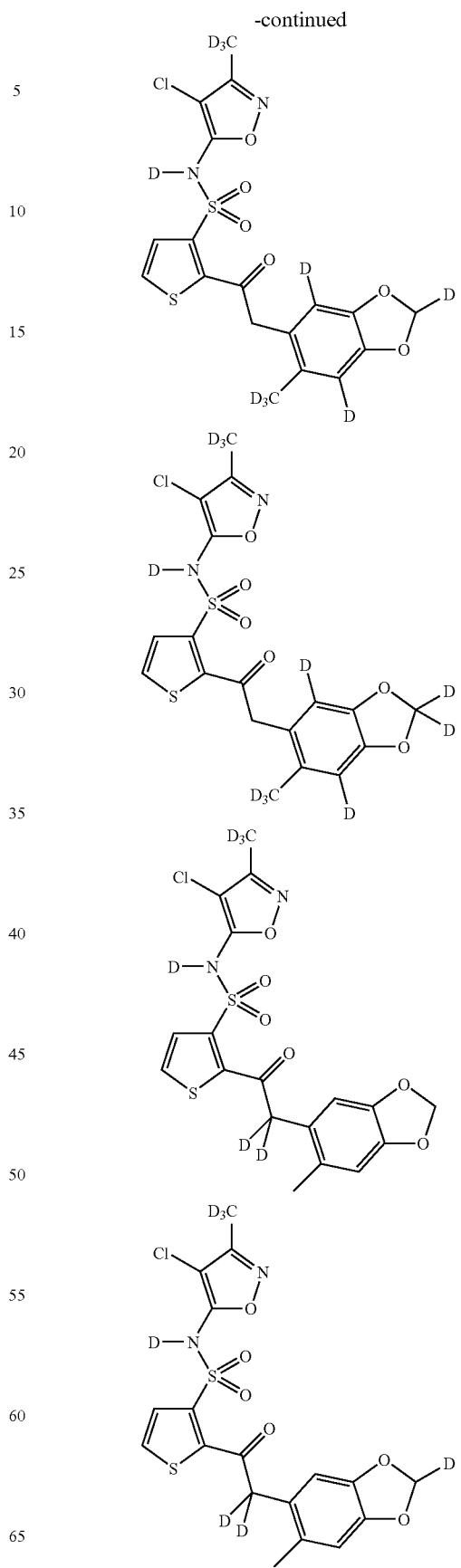

163
-continued
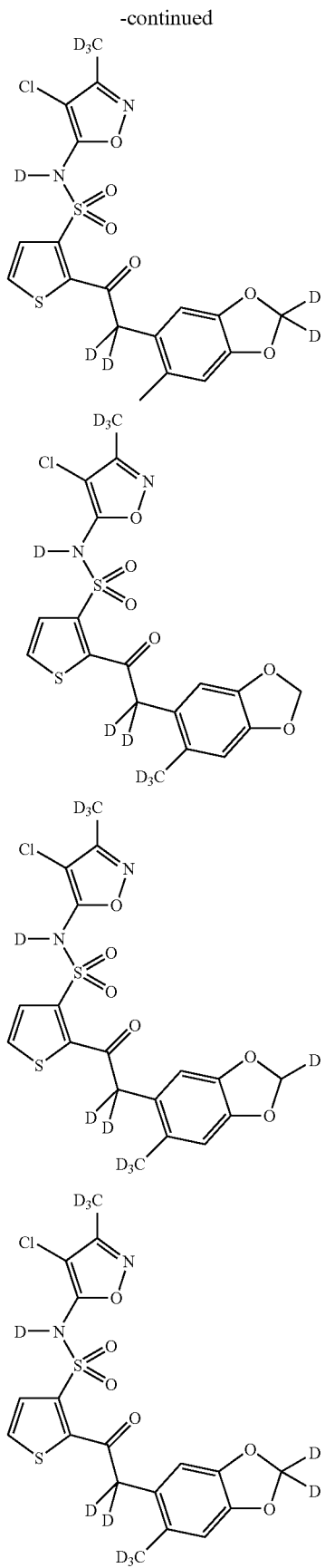
164
-continued
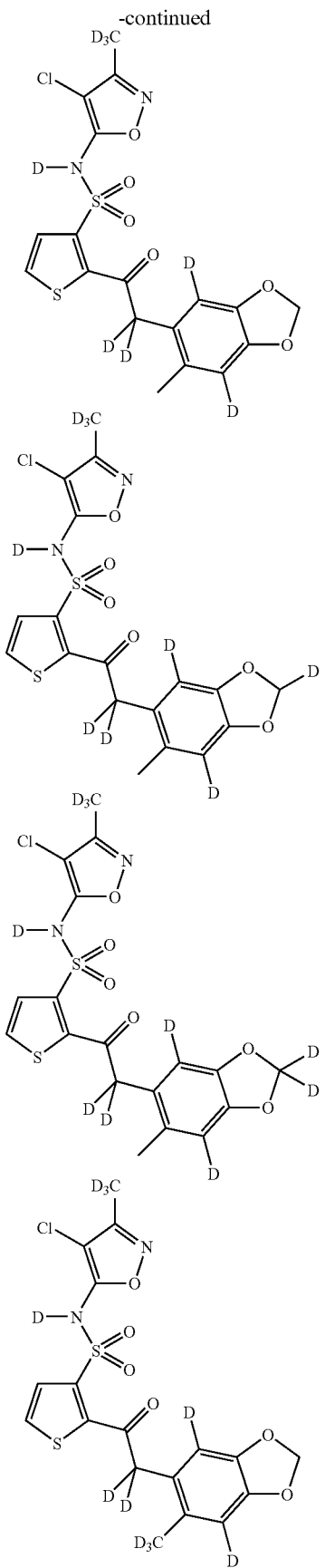

165
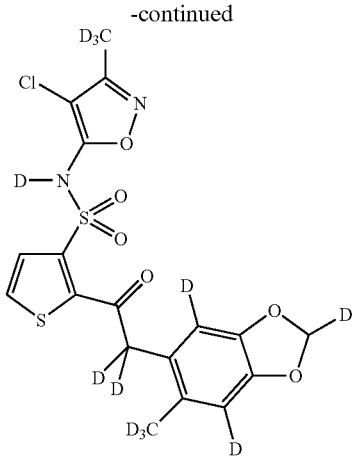
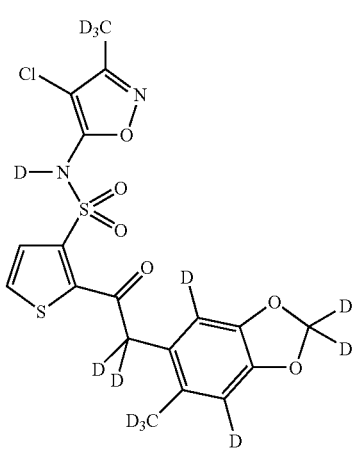
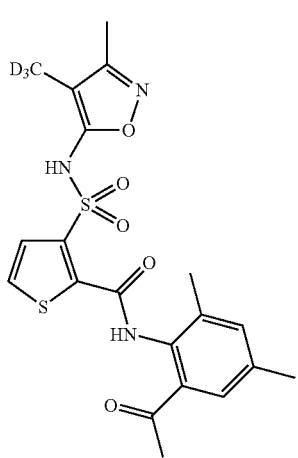
166
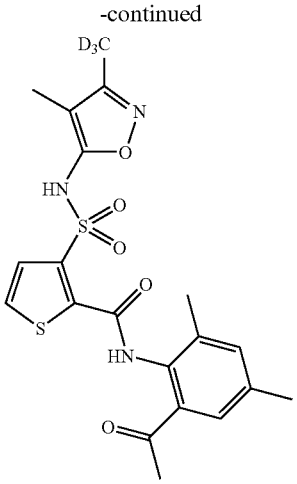
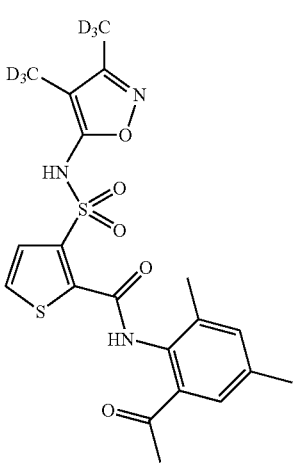
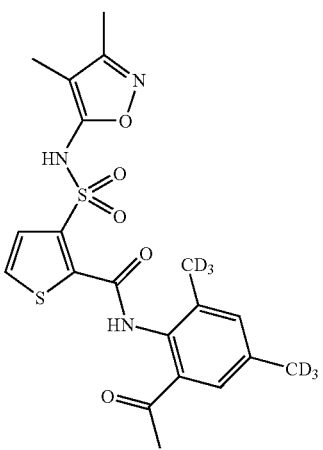

167
-continued
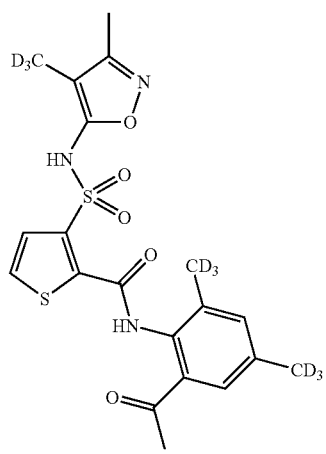
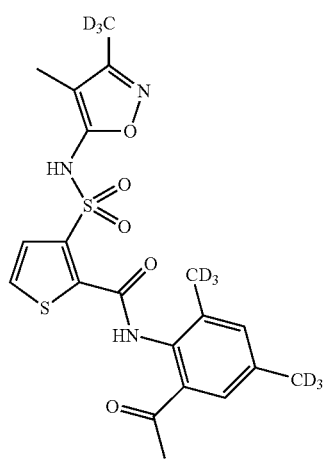
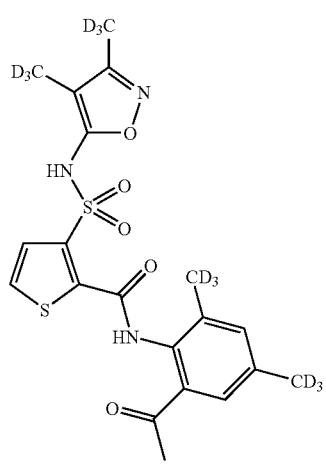
168
-continued
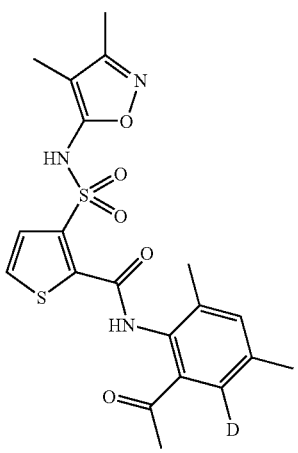
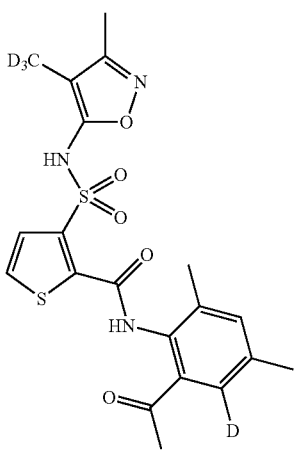
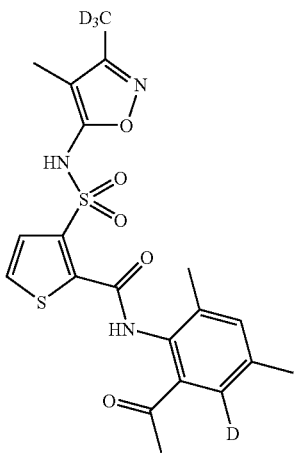

-continued
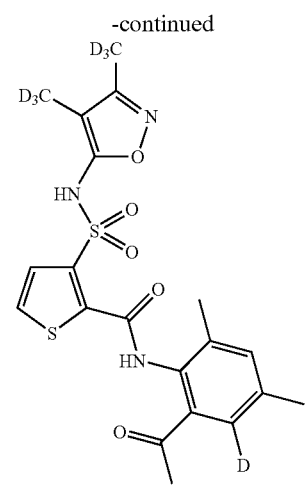
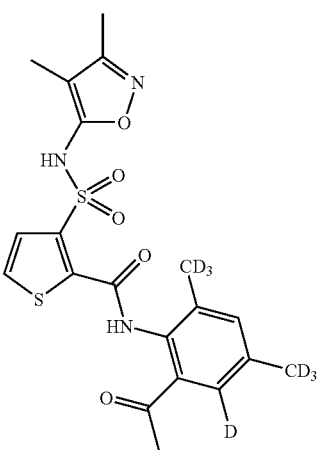
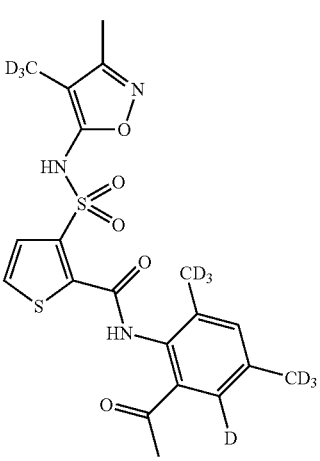
-continued
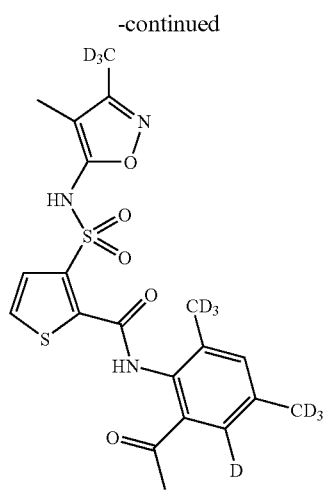
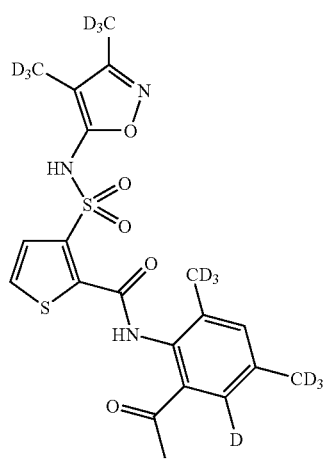
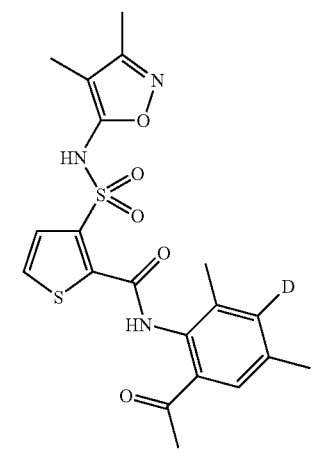

-continued
171
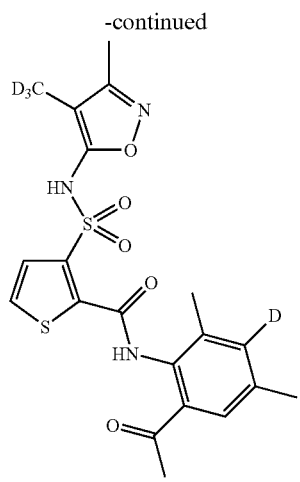
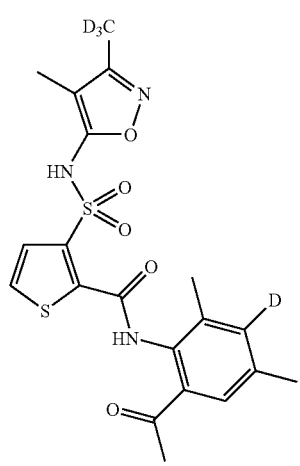
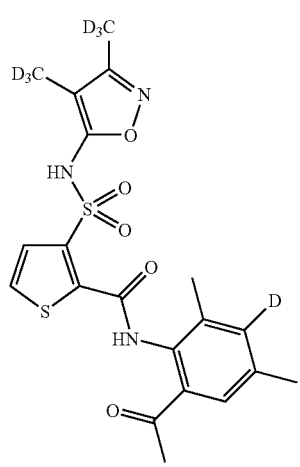
-continued
172
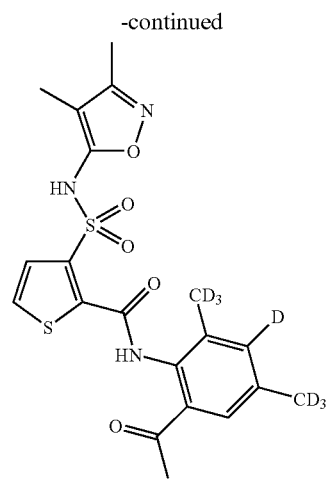
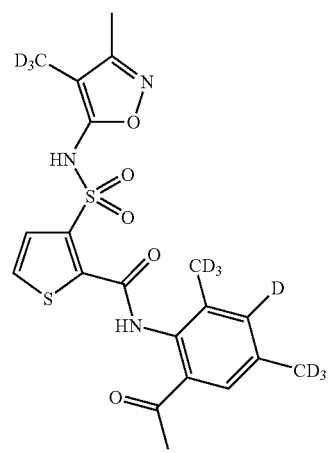
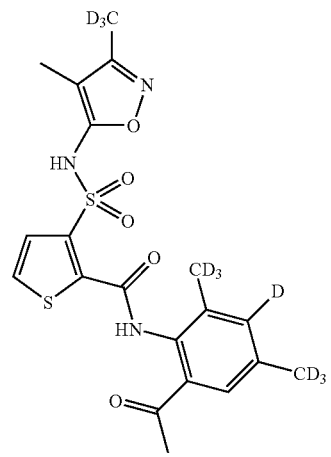

-continued
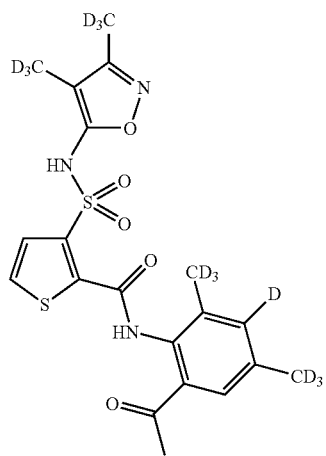
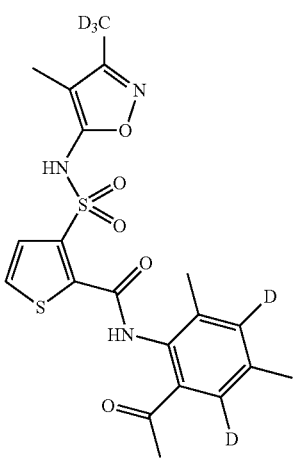
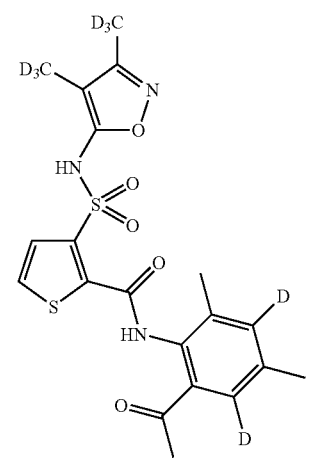
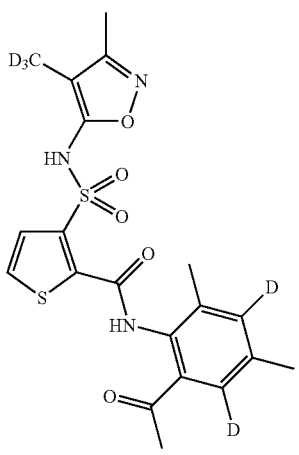
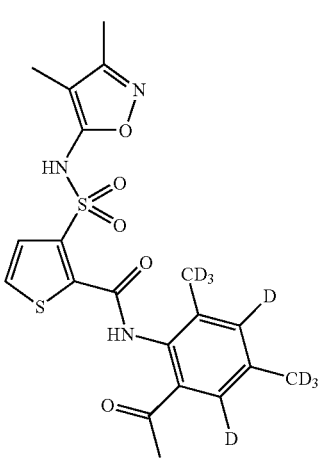

175
-continued
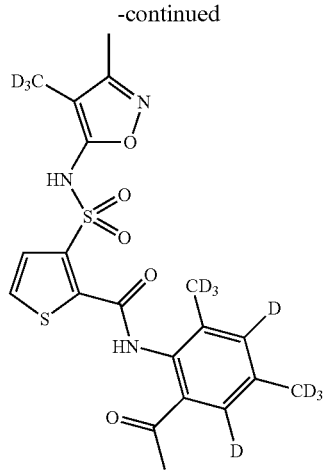
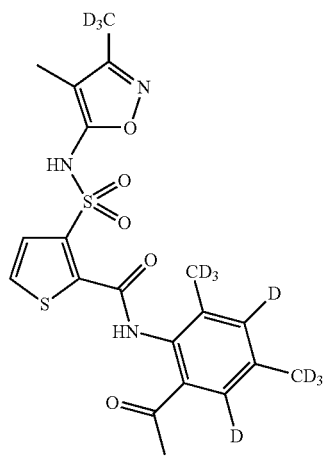
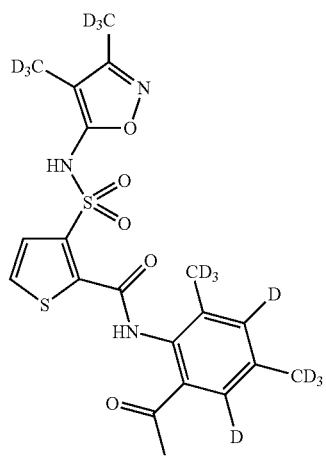
176
-continued
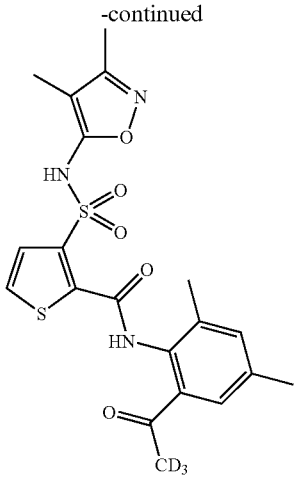
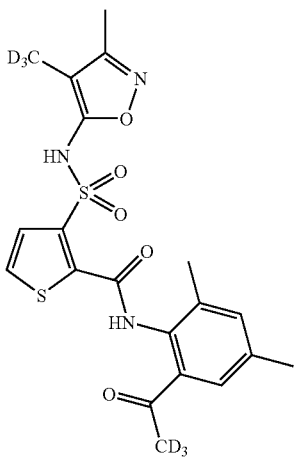
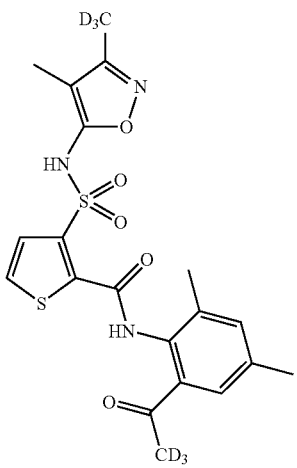

-continued
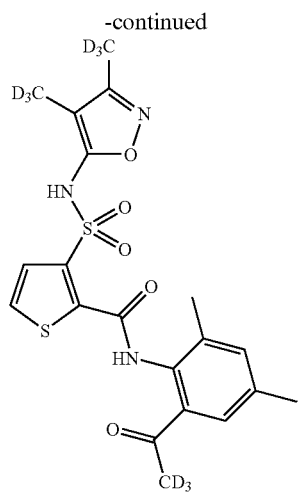
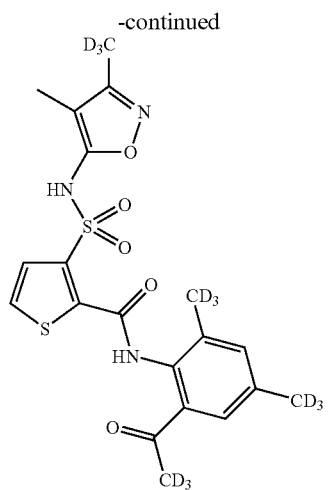
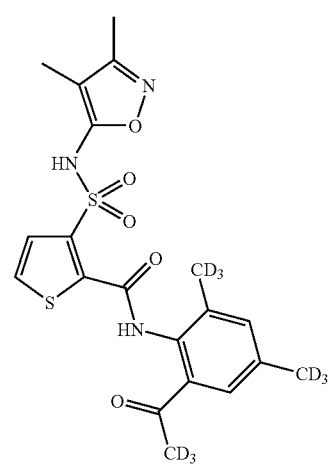
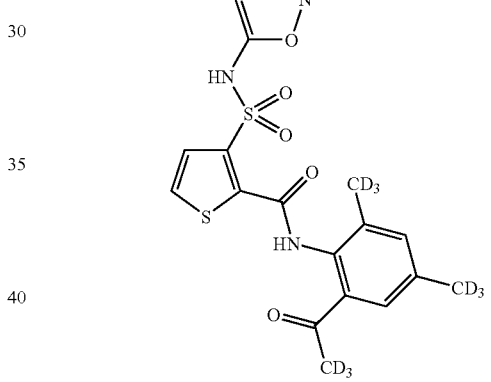
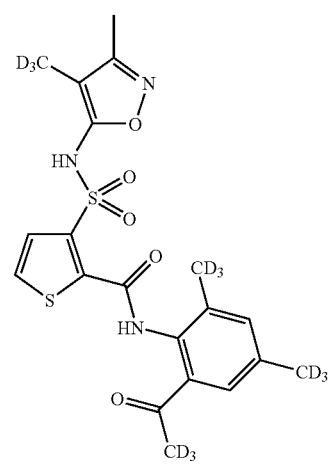
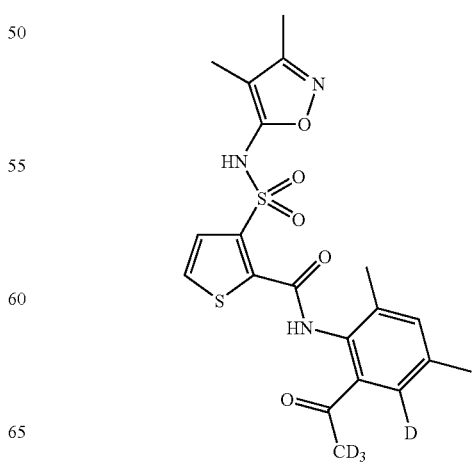

-continued
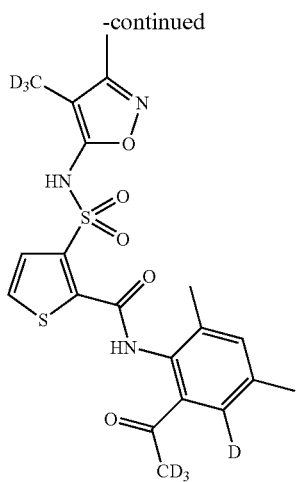
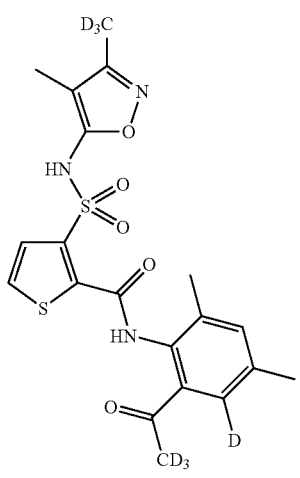
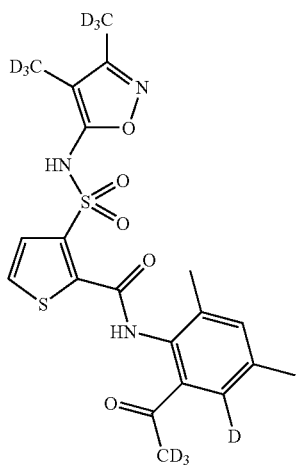
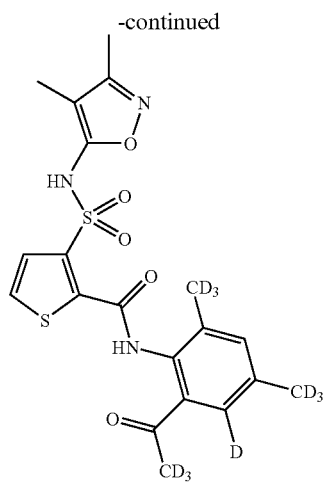
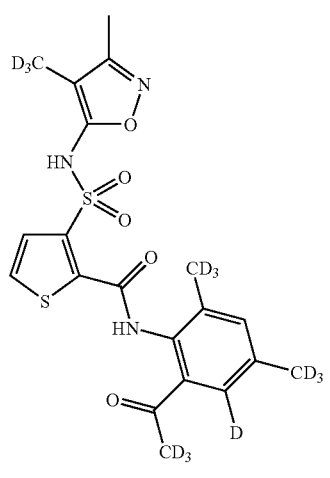
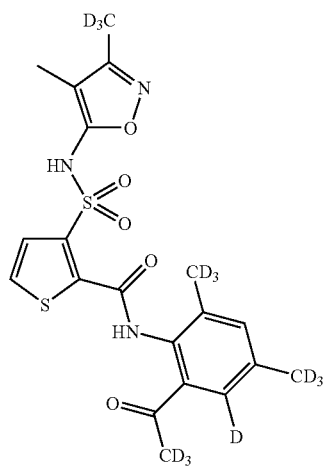

-continued
181
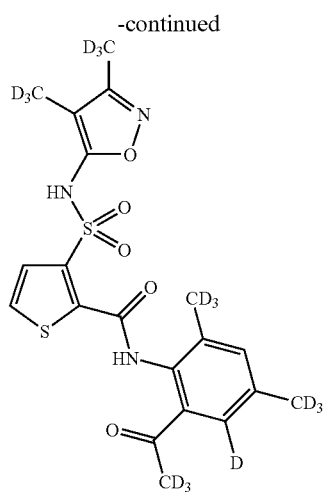
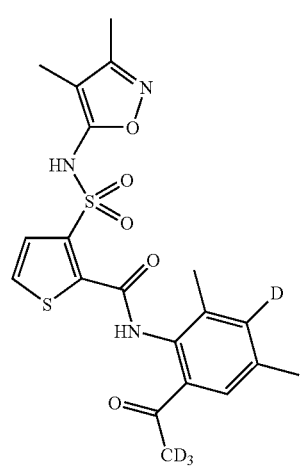
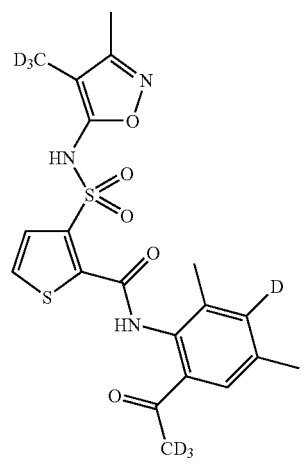
182
-continued
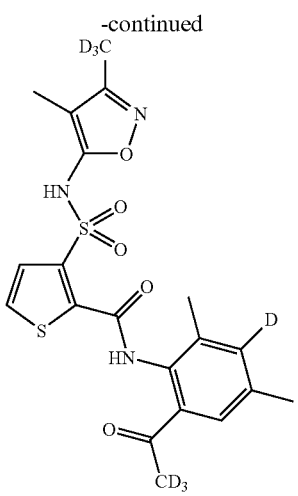
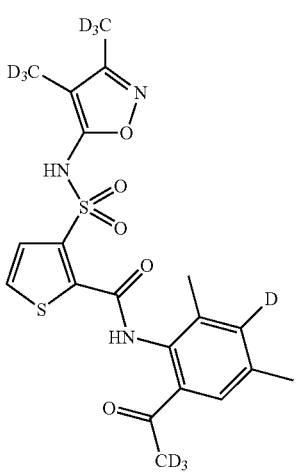
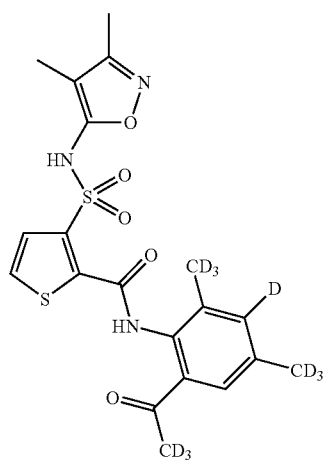

-continued
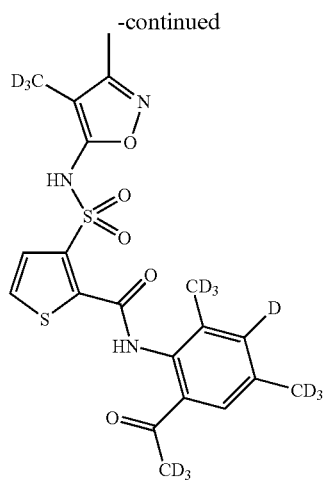
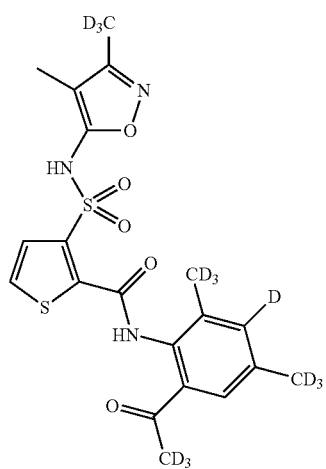
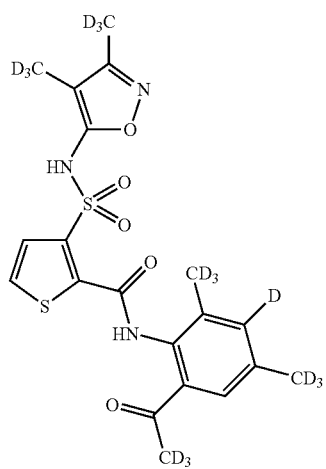
-continued
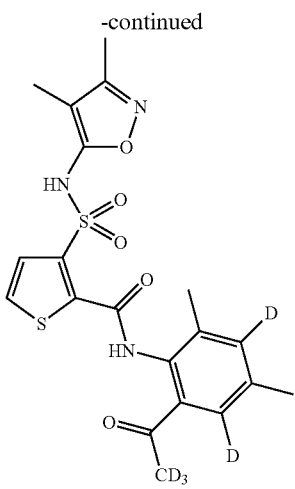
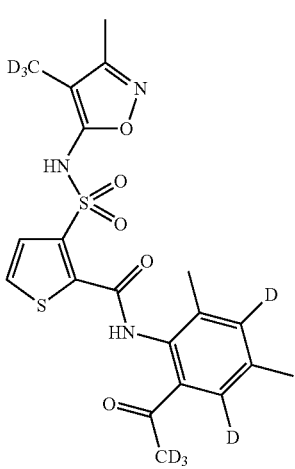
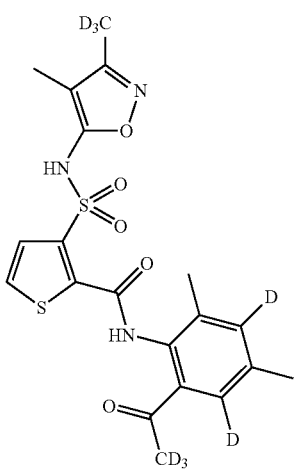

185
-continued
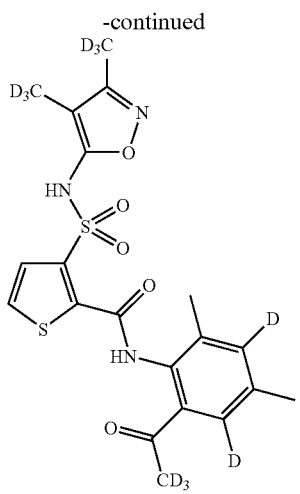
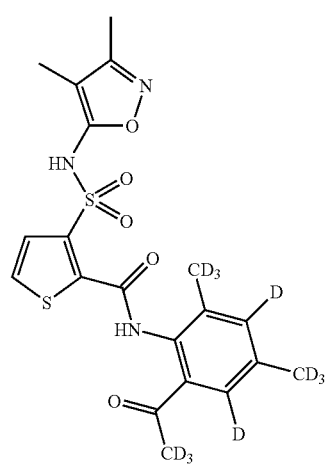
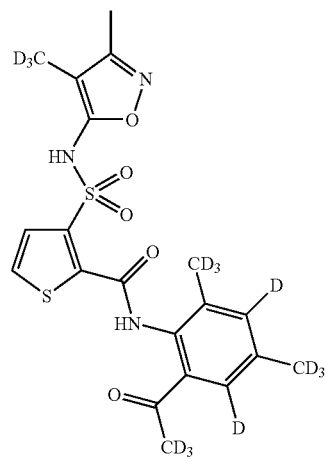
186
-continued
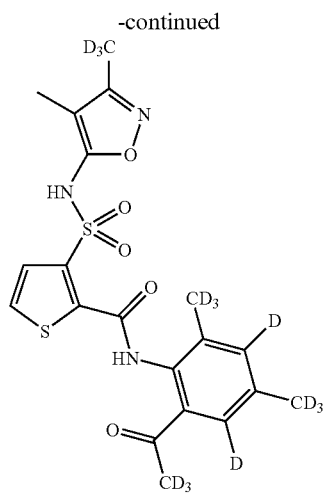
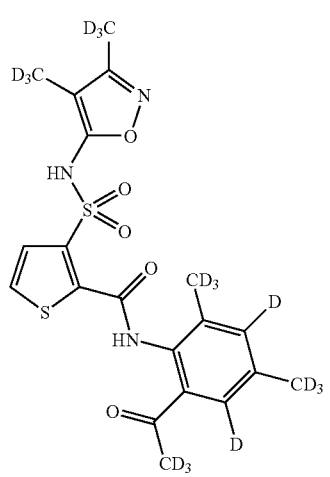
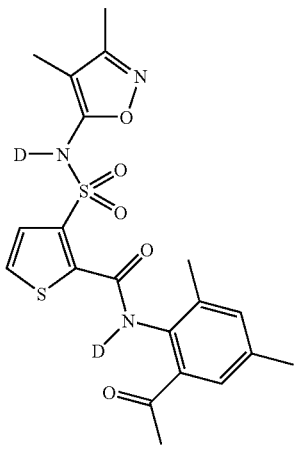

187
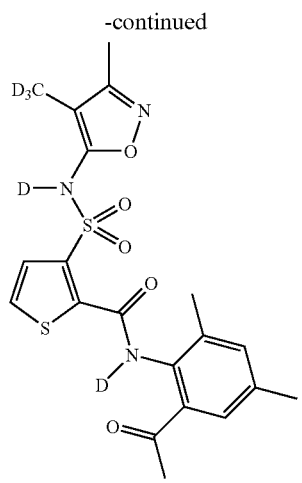
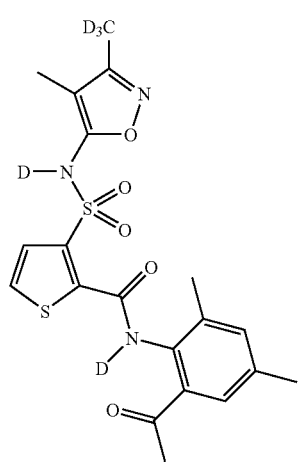
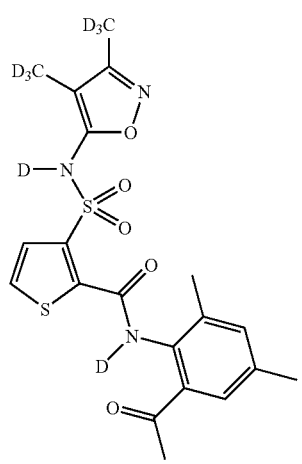
188
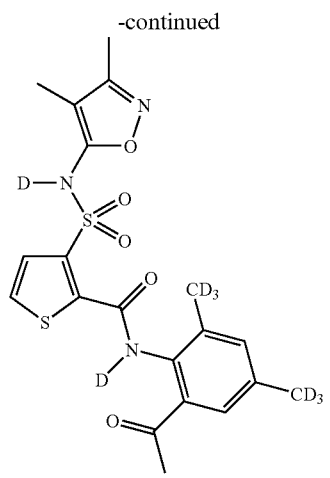
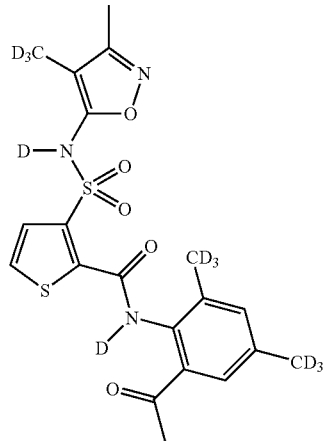
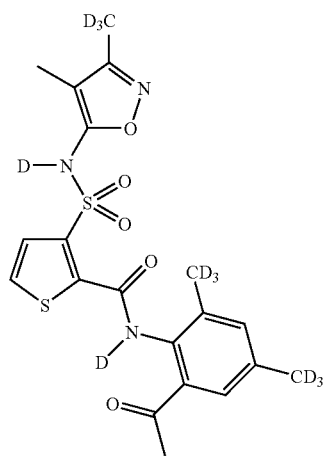

189
-continued
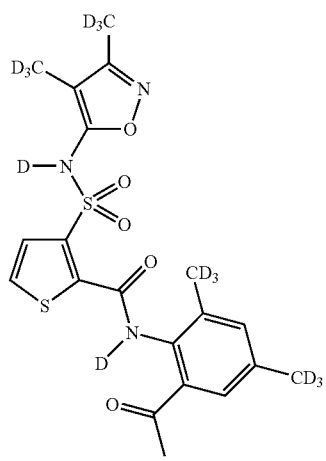
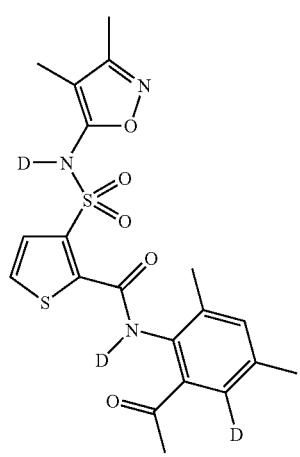
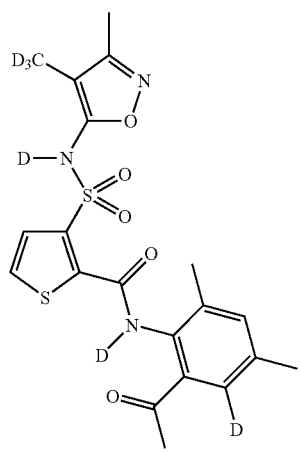
190
-continued
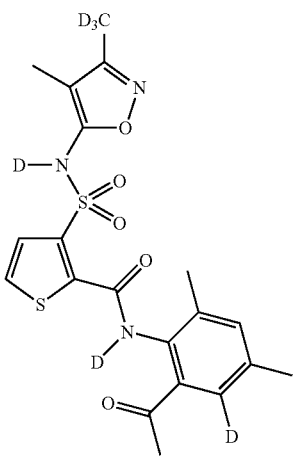
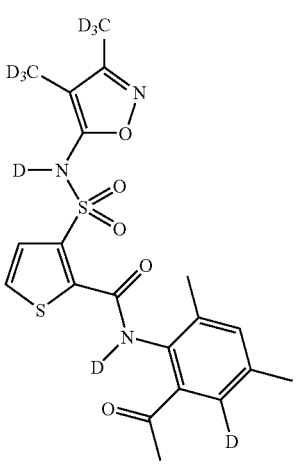
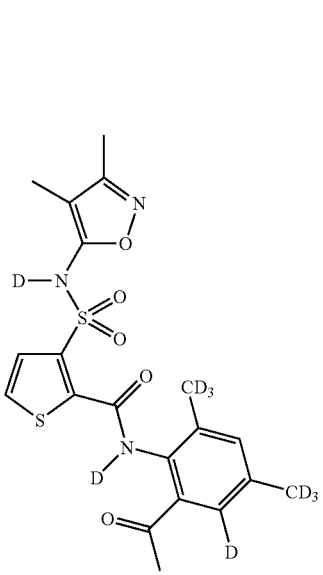

-continued
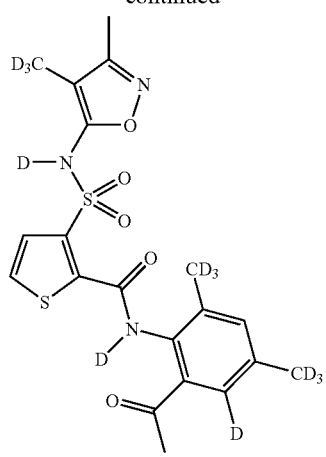
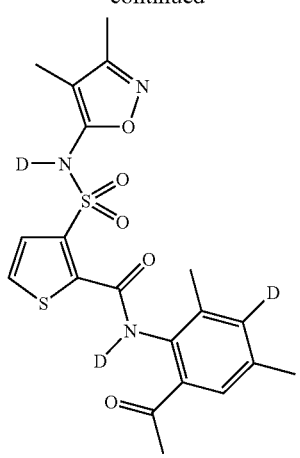
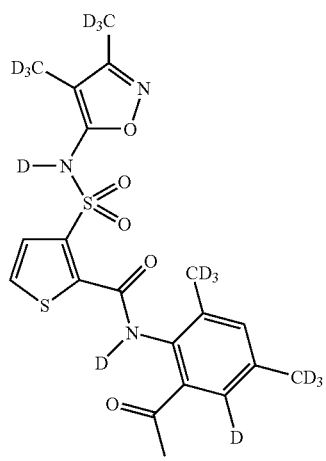
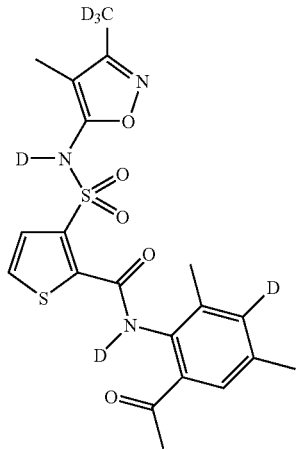

-continued
193
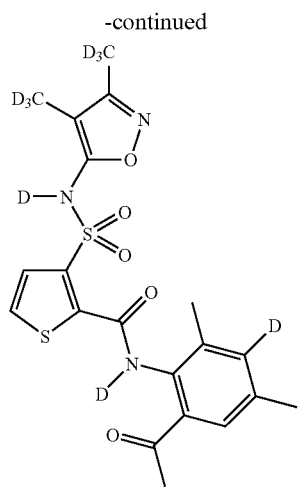
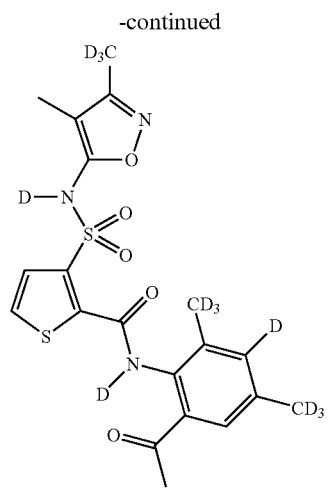
194
-continued
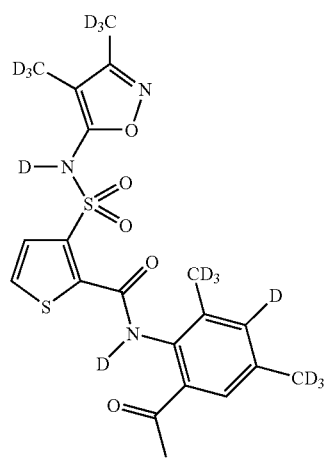
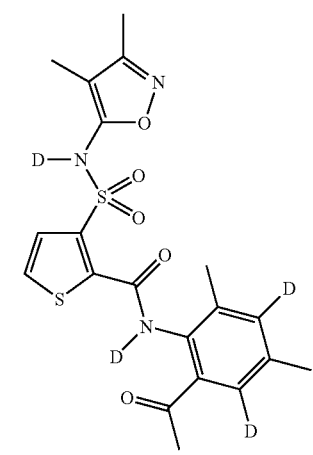

-continued
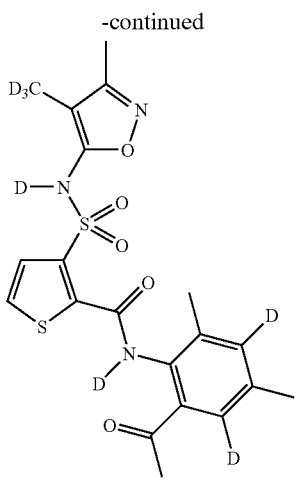
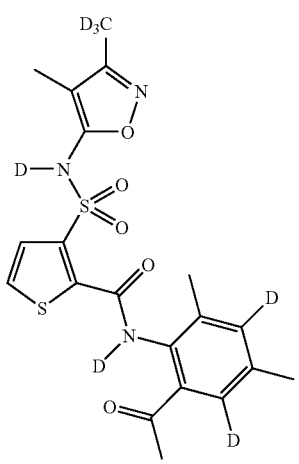
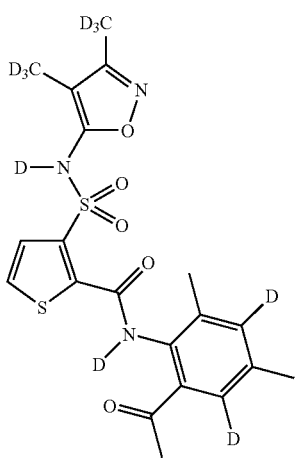
-continued
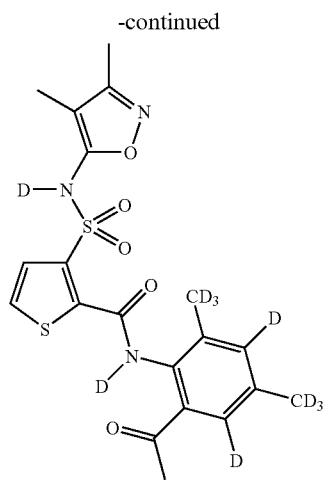
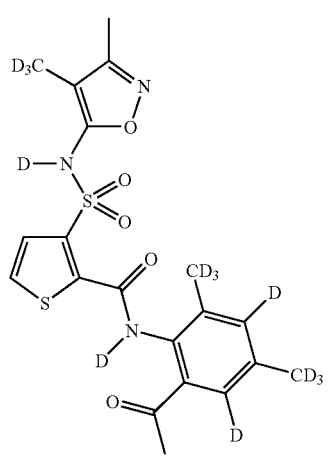
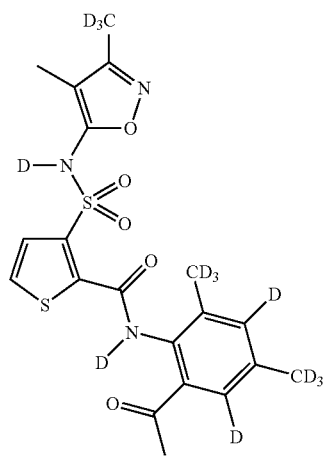

-continued
197
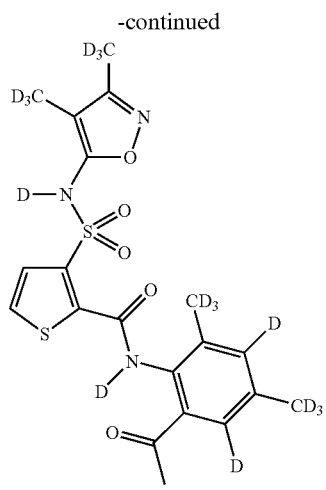
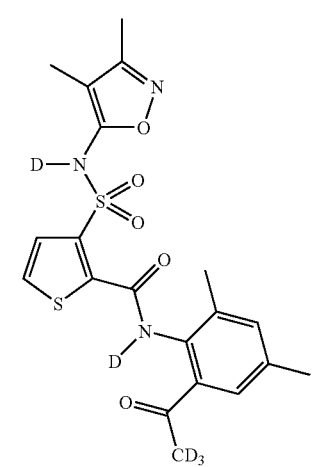
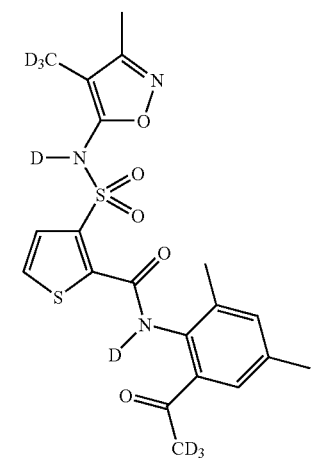
198
-continued
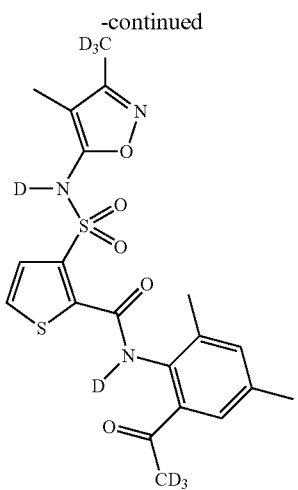
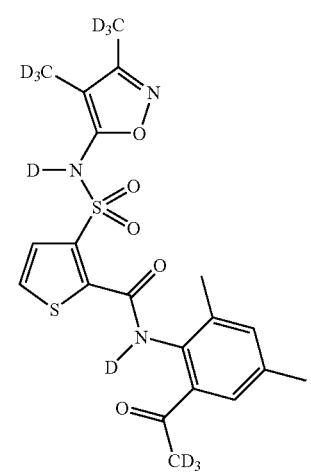
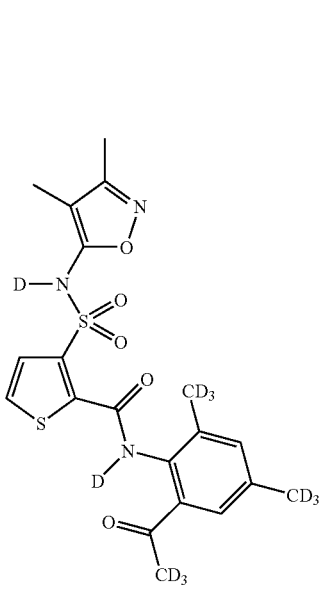

-continued
199
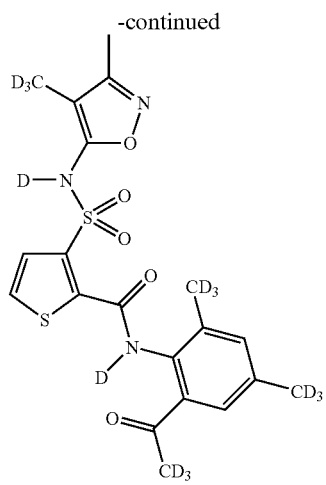
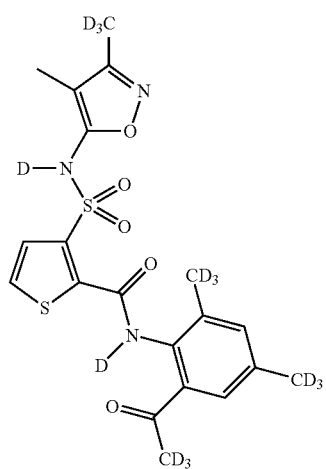
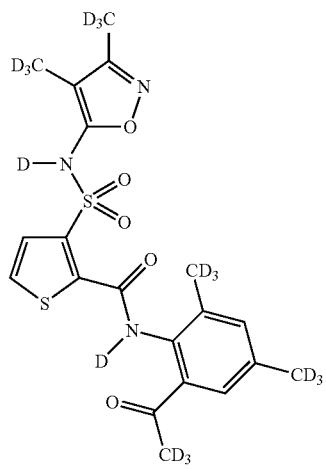
-continued
200
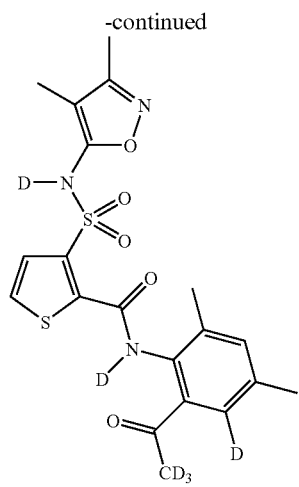
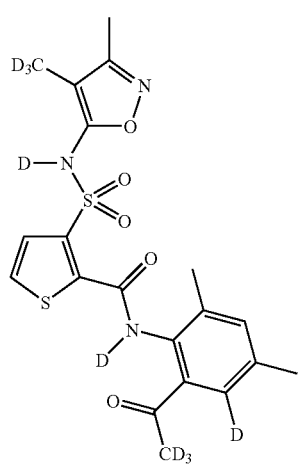
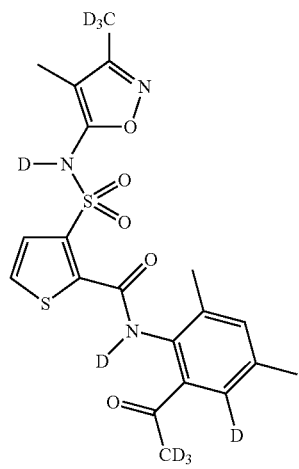

-continued
201
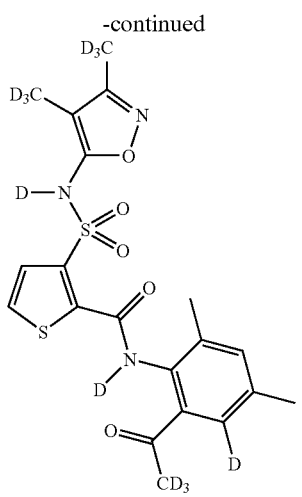
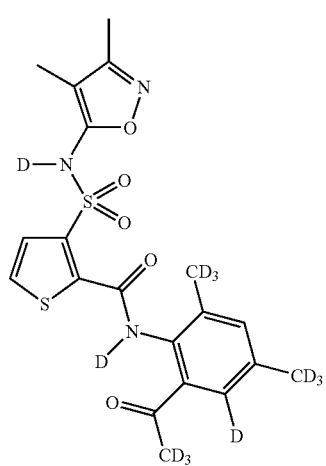
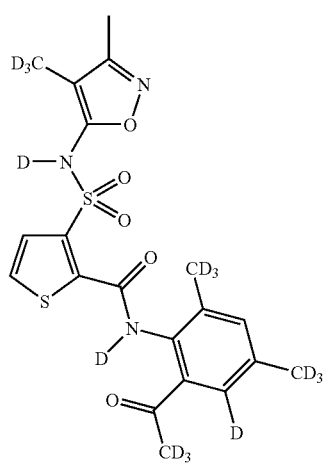
-continued
202
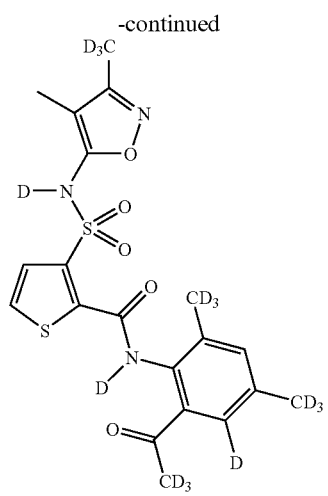
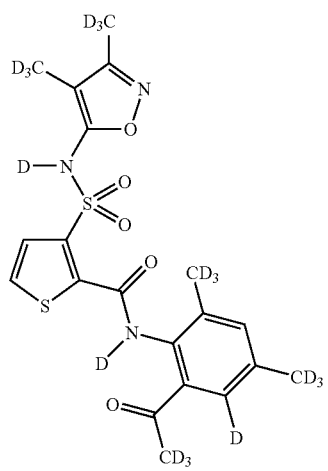
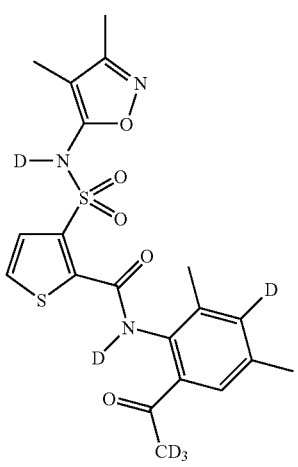

203
-continued
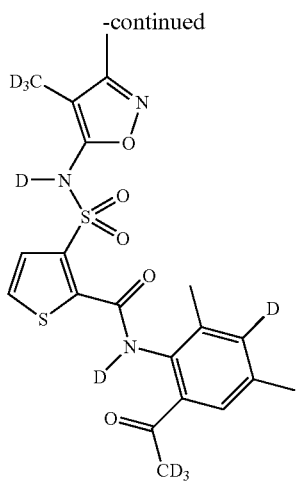
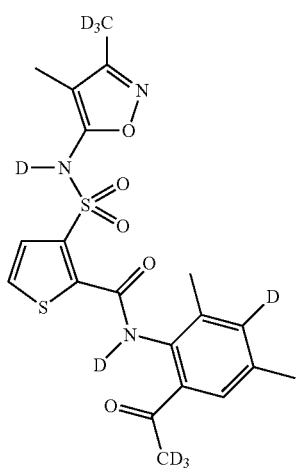
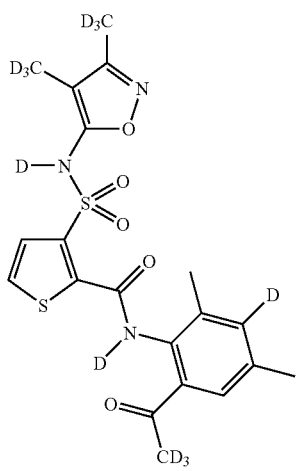
204
-continued
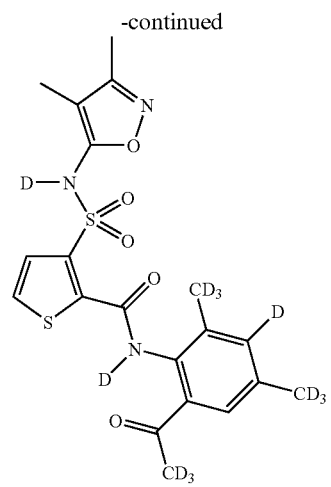
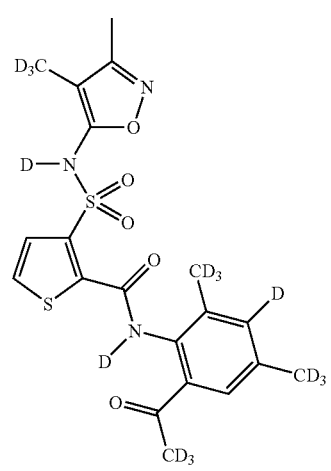
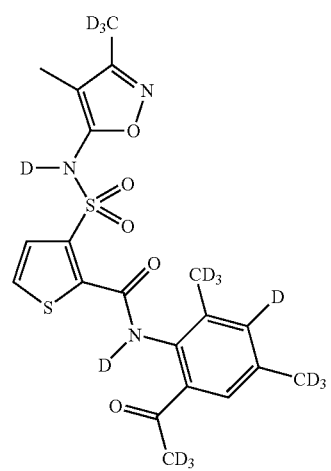

-continued
205
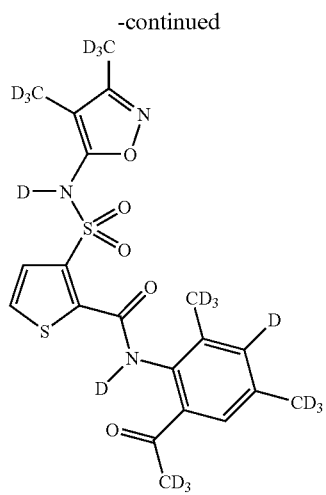
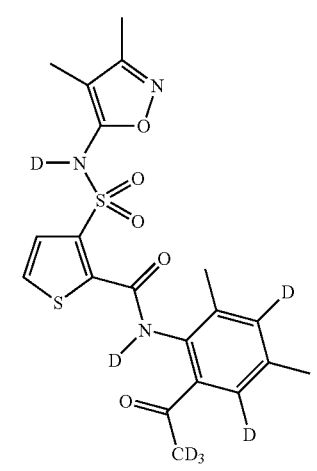
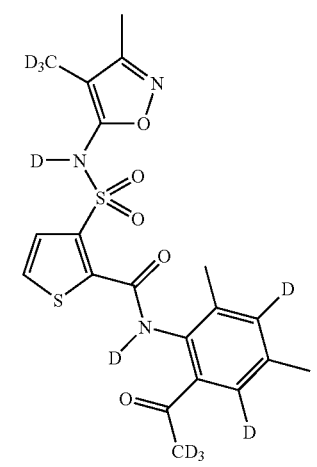
-continued
206
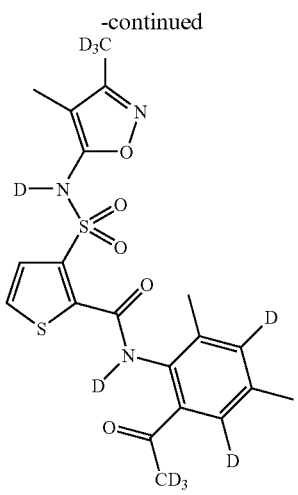
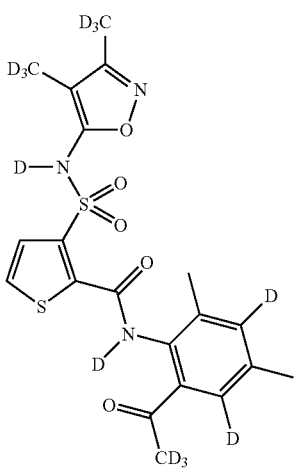
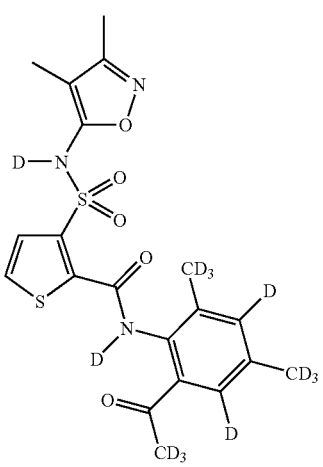

207
-continued
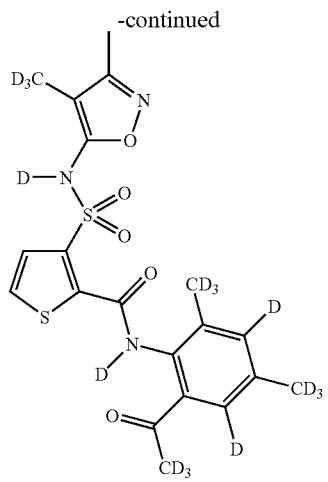
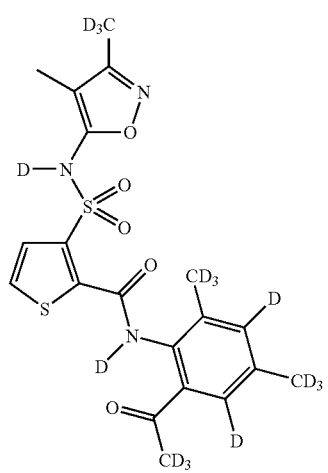
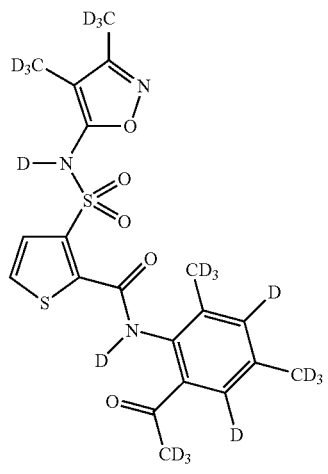
208
-continued
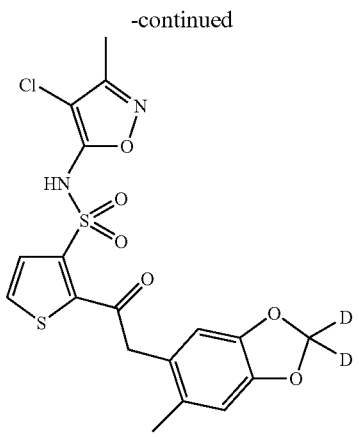
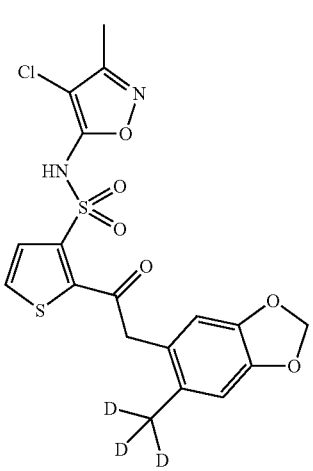
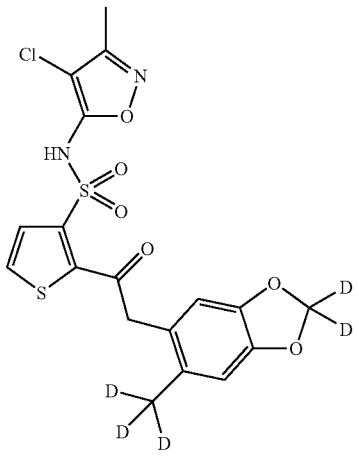

-continued

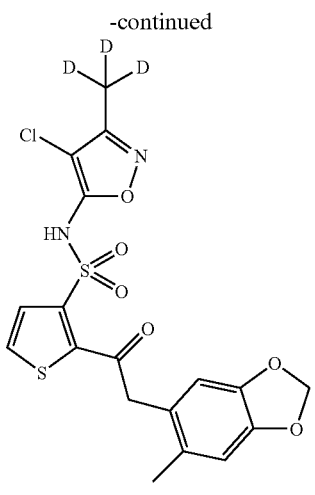

-continued

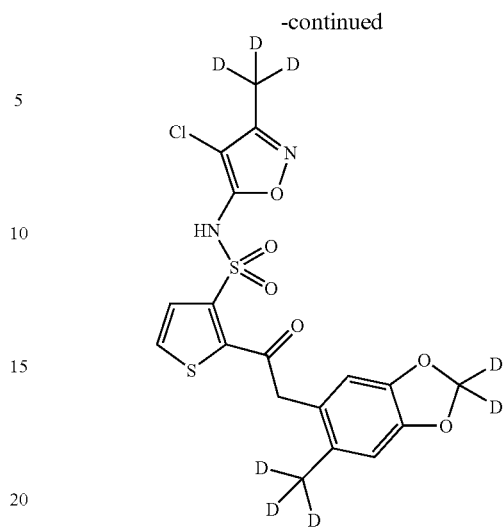

Changes in the metabolic properties of the compounds of Examples 1 to 7 and their analogs as compared to the non-isotopically enriched analogs can be shown using the following assays. Other compounds listed above, which have not yet been made and/or tested, are predicted to have changed metabolic properties as shown by one or more of these assays as well.

Example 8

In Vitro Liver Microsomal Stability Assay

Liver microsomal stability assays are conducted at 1 mg per mL liver microsome protein with an NADPH-generating system in 2% NaHCO$_3$ (2.2 mM NADPH, 25.6 mM glucose 6-phosphate, 6 units per mL glucose 6-phosphate dehydrogenase and 3.3 mM MgCl$_2$). Test compounds are prepared as solutions in 20% acetonitrile-water and added to the assay mixture (final assay concentration 5 microgram per mL) and incubated at 37° C. Final concentration of acetonitrile in the assay should be <1%. Aliquots (50 L) are taken out at times 0, 15, 30, 45, and 60 min, and diluted with ice cold acetonitrile (200 μL) to stop the reactions. Samples are centrifuged at 12,000 RPM for 10 min to precipitate proteins. Supernatants are transferred to microcentrifuge tubes and stored for LC/MS/MS analysis of the degradation half-life of the test compounds.

Example 9

In Vitro Metabolism Using Human Cytochrome P$_{450}$ Enzymes

The cytochrome P$_{450}$ enzymes are expressed from the corresponding human cDNA using a baculovirus expression system (BD Biosciences, San Jose, Calif.). A 0.25 milliliter reaction mixture containing 0.8 milligrams per milliliter protein, 1.3 millimolar NADP$^+$, 3.3 millimolar glucose-6-phosphate, 0.4 U/mL glucose-6-phosphate dehydrogenase, 3.3 millimolar magnesium chloride and 0.2 millimolar of a compound of Formula I, the corresponding non-isotopically enriched compound or standard or control in 100 millimolar potassium phosphate (pH 7.4) is incubated at 37° C. for 20 min. After incubation, the reaction is stopped by the addition of an appropriate solvent (e.g., acetonitrile, 20% trichloroacetic acid, 94% acetonitrile/6% glacial acetic acid, 70% perchloric acid, 94% acetonitrile/6% glacial acetic acid) and centrifuged (10,000 g) for 3 min. The supernatant is analyzed by HPLC/MS/MS.

| Cytochrome $P_{450}$ | Standard |
|---|---|
| CYP1A2 | Phenacetin |
| CYP2A6 | Coumarin |
| CYP2B6 | [$^{13}$C]-(S)-mephenytoin |
| CYP2C8 | Paclitaxel |
| CYP2C9 | Diclofenac |
| CYP2C19 | [$^{13}$C]-(S)-mephenytoin |
| CYP2D6 | (+/−)-Bufuralol |
| CYP2E1 | Chlorzoxazone |
| CYP3A4 | Testosterone |
| CYP4A | [$^{13}$C]-Lauric acid |

Example 10

Monoamine Oxidase A Inhibition and Oxidative Turnover

The procedure is carried out as described in Weyler, *Journal of Biological Chemistry* 1985, 260, 13199-13207. Monoamine oxidase A activity is measured spectrophotometrically by monitoring the increase in absorbance at 314 nm on oxidation of kynuramine with formation of 4-hydroxyquinoline. The measurements are carried out, at 30° C., in 50 mM $NaP_i$ buffer, pH 7.2, containing 0.2% Triton X-100 (monoamine oxidase assay buffer), plus 1 mM kynuramine, and the desired amount of enzyme in 1 mL total volume.

Example 11

Monoamine Oxidase B Inhibition and Oxidative Turnover

The procedure is carried out as described in Uebelhack, *Pharmacopsychiatry* 1998, 31, 187-192.

Example 12

Preparation of Platelet-Rich Plasma and Platelets

Venous blood from healthy subjects is collected between 8 and 8:30 a.m. after overnight fasting into EDTA-containing vacutainer tubes (11.6 mg EDTA/mL blood).

After centrifugation of the blood at 250×g for 15 min at 20° C., the supernatant platelet-rich plasma (PRP) is collected and the number of platelets in PRP and counted with a cell counter (MÖLAB, Hilden, Germany). PRP (2 mL) is spun at 1,500×g for 10 min to yield a platelet pellet. The pellet is washed three times with ice-cold saline, resuspended in 2 mL Soerensen phosphate buffer, pH 7.4, and stored at −18° C. for one day.

Example 13

MAO Assay

Fresh PRP or frozen platelet suspension (100 μL) is generally preincubated for 10 min in the absence or presence of the compound of Formula I at 37° C. in 100 μL of 0.9% NaCl solution or phosphate buffer pH 7.4, respectively. 2-Phenylethylamine-[ethyl-1-$^{14}$C]hydrochloride (PEA) solution (specific activity 56 Ci/mol, Amersham, 50 μL) is then added in a final concentration of 5 μM and the incubation is continued for 30 min. The reaction is terminated by the addition of 50 μL 4M $HClO_4$. The reaction product of MAO, phenylacetaldehyde, is extracted into 2 mL of n-hexane. An aliquot of the organic phase is added to scintillator cocktail and the radioactivity is determined using a liquid scintillation counter. Product formation is linear with time for at least 60 min with appropriate platelet numbers. Blank values are obtained by including 2 mM pargyline in the incubation mixtures.

Example 14

Pharmacology-In Vitro Assays

In vitro characterization of modulation of $ET_A$ and $ET_B$ is carried out as described in Hwan-Soo, *J. Med. Chem.* 1997, 40, 3217-3227.

Receptor Binding Assays

All samples are kept at 4° C. throughout the process of membrane isolation. MMQ cells (prolactin secreting rat pituitary cells known to contain $ET_A$ receptors), porcine cerebellar tissues (known to contain $ET_B$ receptors), or Chinese hamster ovary cells (CHO) permanently transfected with the human $ET_A$ or $ET_B$ receptor are homogenized in 25 mL of 10 mM Hepes (pH 7.4) containing 0.25 M sucrose and a protease inhibitor cocktail (50 mM EDTA, 0.1 mM PMSF, and 5 microgram/mL Pepstatin A, and 0.025% Bacitracin) using a micro ultrasonic cell disruptor (Kontes). The mixture is centrifuged at 1,000 g for 10 min. The supernatant is collected and centrifuged at 60,000 g for 60 min. The precipitate is resuspended in 20 mM Tris, pH 7.4, containing protease inhibitor cocktail, and centrifuged again. The final membrane pellet is resuspended in 20 mM Tris, pH 7.4, containing protease inhibitors, and stored at −80° C. until used. Protein content is determined by the Bio-Rad dye-binding protein assay.

Binding assays are performed in 96-well microtiter plates pretreated with 0.1% BSA. Membranes are diluted 100-fold in buffer B (20 mM Tris, 100 mM NaCl, 10 mM $MgCl_2$, pH 7.4, with 0.2% BSA, 0.1 mM PMSF, 5 microgram/mL Pepstatin A, 0.025% bacitracin, and 50 mM EDTA) to a final concentration of 0.2 mg/mL of protein. In competition binding studies, membranes (0.02 mg) are incubated with 0.1 nM of [$^{125}$I]ET-1 (for $ET_A$ assay in MMQ or CHO cells) or [$^{125}$I] ET-3 (for $ET_B$ assay in porcine cerebellum or CHO cells) in buffer B (final volume: 0.2 mL) in the presence of increasing concentrations of the test compound for 3 hours at 25° C. After incubation, unbound ligand is separated from bound ligand by a vacuum filtration method using glass-fiber filter strips in PHD cell harvesters (Cambridge Technology, Inc., Cambridge, Mass.), washing the filter strips three times with saline (1 mL).

Nonspecific binding is determined in the presence of 1 micromolar unlabeled ET-1. $IC_{50}$ values are calculated using an average of at least two separate determinations.

Phosphoinositol Hydrolysis Assays. $ET_A$

MMQ cells (0.4×106 cells/mL) are labeled with 10 microCurie/mL of [$^3$H]-myoinositol in RPMI for 16 hr. The cells are washed with PBS and then incubated with buffer A (140 mM NaCl, 5 mM KCl, 2 mM $CaCl_2$, 0.8 mM $MgSO_4$, 5 mM glucose, 25 mM Hepes, pH 7.4) containing protease inhibitors and 10 mM LiCl for 60 minutes. The cells are incubated with test compounds for 5 min and then challenged with 1 nM ET-1. ET-1 challenge was terminated by the addition of 1.5 mL of 1:2 (v/v) chloroform-methanol. Total inositol phosphates are extracted after adding chloroform and water to give final proportions of 1:1:0.9 (v/v/v) chloroform-methanol-water. The upper aqueous phase (1 mL) is retained, and a small portion (100 microliter) is counted. The rest of the aqueous sample is analyzed by batch chromatography using anion-exchange resin AG1-X8 (Bio-Rad).

Phosphoinositol Hydrolysis Assays. ETB

Chinese hamster ovary cells (CHO) permanently transfected with the human ETB receptor are grown to confluence in 24-well tissue culture plates and labeled with 5 microCurie/well of [$^3$H]myoinositol in F-12 media+10% FBS+1xP/S/F. The adherent cells are washed gently with PBS and then incubated in 200 microliter of buffer A containing protease inhibitors and 10 mM LiCl for 60 min at 37° C. in a $CO_2$ incubator. Test compounds are then added followed by the addition of 1 nM ET-1 and incubated for 30 min at 37° C. The cells are then solubilized by the addition of 50 microliters of 1 N NaOH and then neutralized by the addition of 50 microliters of 1 N HCl. The solubilized cell suspension is transferred to glass tubes and extracted by the addition of 1.5 mL of 1:2 (v/v) chloroform-methanol. Total inositol phosphates are extracted and analyzed by batch chromatography on anion exchange resin as above. All $IC_{50}$ values are calculated using an average of at least two separate determinations.

Example 15

In Vitro Inhibition of Human Cytochrome $P_{45}$ Enzymes

CYP2C9

Solution A: NADPH-Regenerating System

To a glass tube on ice were added sequentially: Water (8 mL) in NADP+ (20 mg), glucose-6-phosphate (20 mg), magnesium chloride hexahydrate (13.3 mg) and glucose-6-phosphate dehydrogenase (60 units).

Solution B

To a glass tube on ice were added sequentially: 0.5 M $KH_2PO_4$ (pH 7.4, 2.4 mL), water (8.988 mL), CYP2C9 (600 µL of 1 picomol/microliter), and dibenzylfluorescein (2 mM in 100% acetonitrile, 12 microliter).

Solution A was transferred to a 96-well black plate (80 microliter per well), followed by various concentrations of a solution of Compound in 10% acetonitrile-water (20 microliter per well). The reaction was initiated by adding 100 microliter of solution B to each well of the 96-well plate. The plate was incubated for 40 minutes at 37° C. in the dark. The reaction was stopped by adding 75 microliters of stop buffer (2 N NaOH) to each well, and incubating at 37° C. for 2 hours. The end point was measured in a fluorometer plate reader at $\lambda_{ex}$=485 nm and $\lambda_{em}$=538 nm. Sulfaphenazole was used as positive control ($IC_{50}$=1.4 micromolar). Compounds having structural Formula (I) that have been tested in this assay, demonstrate that it takes more two times the amount of deuterated compound to inhibit CYP2C9, as compared to the non-isotopically enriched drug. For example, it took 3.2 times the amount of the compound of Example 2 ($IC_{50}$ 0.32 µM) to inhibit CYP2C9 than non-isotopically enriched sixtaxsentan ($IC_{50}$ 0.1 µM).

CYP3A4

Solution A: NADPH-Regenerating System

To a glass tube on ice were added sequentially: Water (8 mL) in NADP+ (20 mg), glucose-6-phosphate (20 mg), magnesium chloride hexahydrate (13.3 mg) and glucose-6-phosphate dehydrogenase (60 units).

Solution B

To a glass tube on ice were added sequentially: 0.5 M $KH_2PO_4$ (pH 7.4, 9.6 mL), water (2.328 mL), CYP3A4 (60 µL of 1 picomol/microliter), and dibenzylfluorescein (2 mM in 100% acetonitrile, 12 microliter).

Solution A was transferred to a 96-well black plate (80 microliter per well), followed by various concentrations of a solution of Compound in 20% acetonitrile-water (20 microliter per well). The reaction was initiated by adding 100 microliter of solution B to each well of the 96-well plate. The plate was incubated for 10 minutes at 37° C. in the dark. The reaction was stopped by adding 75 microliter of stop buffer (2 N NaOH) to each well, and incubating at 37° C. for 2 hours. The end point was measured in a fluorometer plate reader at $\lambda_{ex}$=485 nm and $\lambda_{em}$=538 nm. Ketoconazole was used as positive control ($IC_{50}$=5.7 nanomolar). Compounds having structural Formula (I) that have been tested in this assay, demonstrate that it takes more two times the amount of deuterated compound to inhibit CYP3A4, as compared to the non-isotopically enriched drug. For example, it took 2.3 times the amount of the compound of Example 2 ($IC_{50}$ 21.2 µM) to inhibit CYP3A4 than non-isotopically enriched sixtaxsentan ($IC_{50}$ 9.1 µM).

The examples set forth above are disclosed to give complete disclosure and description of how to make and use the claimed embodiments, and are not intended to limit the scope of what is disclosed herein. Modifications that are obvious are intended to be within the scope of the following claims. All publications, patents, and patent applications cited in this specification are incorporated herein by reference as if each such publication, patent or patent application were specifically and individually indicated to be incorporated herein by reference. However, with respect to any similar or identical terms found in both the incorporated publications or references and those explicitly put forth or defined in this document, then those terms definitions or meanings explicitly put forth in this document shall control in all respects.

What is claimed is:

1. A compound selected from the group consisting of:

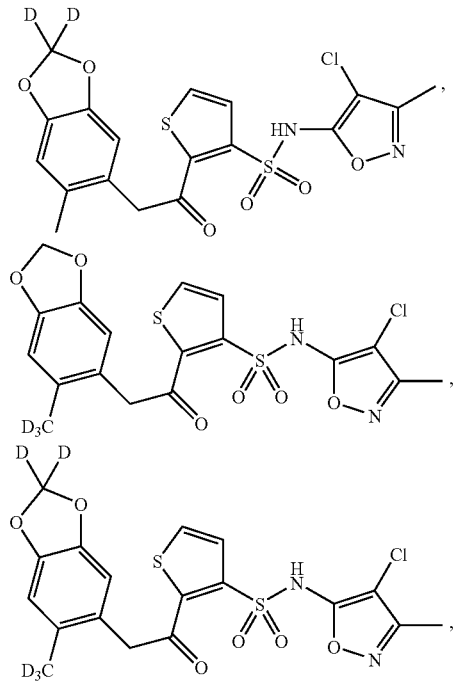

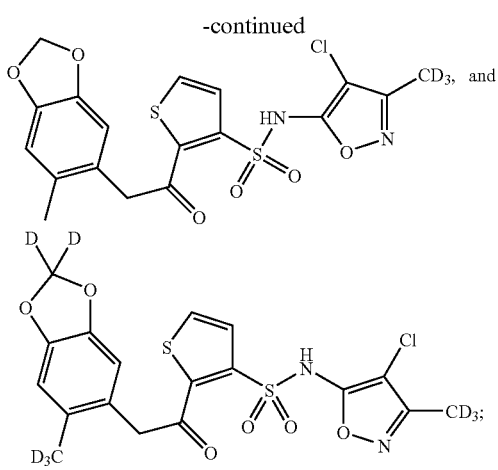

or a pharmaceutically acceptable salt thereof.

2. The compound as recited in claim 1, wherein each of said positions represented as D have deuterium enrichment of at least 98%.

3. The compound as recited in claim 1, wherein each of said positions represented as D have deuterium enrichment of at least 90%.

4. The compound as recited in claim 1, wherein each of said positions represented as D have deuterium enrichment of at least 50%.

5. The compound as recited in claim 1, wherein each of said positions represented as D have deuterium enrichment of at least 20%.

6. The compound as recited in claim 1, wherein each of said positions represented as D have deuterium enrichment of at least 10%.

7. The compound as recited in claim 1, wherein each of said positions represented as D have deuterium enrichment of at least 5%.

8. The compound as recited in claim 1, wherein each of said positions represented as D have deuterium enrichment of at least 1%.

9. A pharmaceutical composition comprising the compound as recited in claim 1, and one or more pharmaceutically acceptable carriers.

10. A pharmaceutical composition as recited in claim 9, further comprising one or more release-controlling excipients.

11. The pharmaceutical composition as recited in claim 9, further comprising one or more non-release controlling excipients.

12. The pharmaceutical composition as recited in claim 9, wherein the composition is suitable for oral, parenteral or intravenous infusion administration.

13. The pharmaceutical composition as recited in claim 12, wherein the oral dosage form is a tablet, or capsule.

14. The pharmaceutical composition as recited in claim 12, wherein the compound is administered in a dose of about 0.5 milligrams to about 1,000 milligrams.

15. The pharmaceutical composition as recited in claim 9, further comprising another therapeutic agent.

16. The pharmaceutical composition as recited in claim 15, wherein the therapeutic agent is selected from the group consisting of endothelin antagonists, congestive heart failure treatments, endothelin converting enzyme (ECE) inhibitors, thromboxane enzyme antagonists, potassium channel openers, thrombin inhibitors, growth factor inhibitors, platelet activating factor (PAF) antagonists, anti-platelet agents, Factor VIIa Inhibitors, Factor Xa Inhibitors, renin inhibitors, neutral endopeptidase (NEP) inhibitors, vasopepsidase inhibitors, HMG CoA reductase inhibitors, squalene synthetase inhibitors, fibrates, bile acid sequestrants, anti-atherosclerotic agents, MTP Inhibitors, calcium channel blockers, potassium channel activators, alpha-PDE5 agents, beta-PDE5 agents, antiarrhythmic agents, diuretics, anti-diabetic agents, PPAR-gamma agonists, mineralocorticoid enzyme antagonists, aP2 inhibitors, protein tyrosine kinase inhibitors, antiinflammatories, antiproliferatives, chemotherapeutic agents, immunosuppressants, anticancer agents, cytotoxic agents, antimetabolites, farnesyl-protein transferase inhibitors, hormonal agents, microtubule-disruptor agents, microtubule-stablizing agents, topoisomerase inhibitors, prenyl-protein transferase inhibitors, cyclosporins, TNF-alpha inhibitors, cyclooxygenase-2 (COX-2) inhibitors, gold compounds, and platinum coordination complexes.

17. The pharmaceutical composition as recited in claim 16, wherein the therapeutic agent is an endothelin antagonist.

18. The pharmaceutical composition as recited in claim 17, wherein the endothelin antagonist is selected from the group consisting of cyclic pentapeptides, acyltripeptides, hexapeptide analogs, anthraquinone derivatives, indanecarboxylic acids, N-pyriminylbenzenesulfonamides, benzenesulfonamides, naphthalenesulfonamides, BE-18257B, BQ-123, PD 156707, L-754,142, SB 209670, SB 217242, A-127722, TAK-044, ambrisentan, and bosentan.

19. The pharmaceutical composition as recited in claim 17, wherein the therapeutic agent is a congestive heart failure treatment.

20. The pharmaceutical composition as recited in claim 19, wherein the congestive heart failure treatment is selected from the group consisting of bumetanide, furosemide, torsemide, chlorthalidone, HCTZ, amiloride, spironolactone, glyceryl trinitrate, isosorbide dinitrate, isosorbide mononitrate, molsidomin, pentaerythritol tetranitrate, alprenolol, oxprenolol, pindolol, propranolol, timolol, sotalol, nadolol, mepindolol, carteolol, tertatolol, bopindolol, bupranolol, penbutolol, cloranolol, practolol, metoprolol, atenolol, acebutolol, betaxolol, bevantolol, bisoprolol, celiprolol, esmolol, epanolol, s-atenolol, nebivolol, talinolol, labetalol, carvedilol, amlodipine, felodipine, isradipine, nicardipine, nifedipine, nimodipine, nisoldipine, nitrendipine, lacidipine, nilvadipine, manidipine, barnidipine, lercanidipine, cilnidipine, benidipine, mibefradil, verapamil, gallopamil, diltiazem, fendiline, bepridil, lidoflazine, perhexiline, aliskiren, remikiren, alacepril, benazepril, captopril, ceranapril, delapril, enalapril, fosinopril, lisinopril, moexipril, perindopril, quinapril, ramipril, spirapril, trandolapril, zofenopril candesartan, eprosartan, irbesartan, losartan, olmesartan, tasosartan, telmisartan, valsartan, spironolactone and eplerenone.

21. A compound of claim 1 having the structural formula:

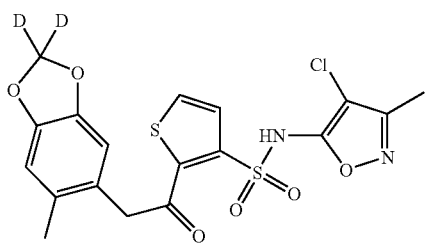

or a pharmaceutically acceptable salt thereof.

22. A compound of claim 1 having the structural formula:

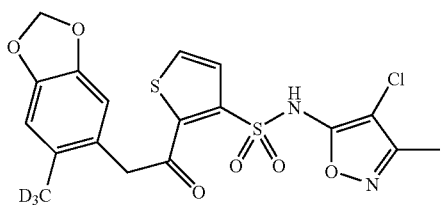

or a pharmaceutically acceptable salt thereof.

23. A compound of claim 1 having the structural formula:

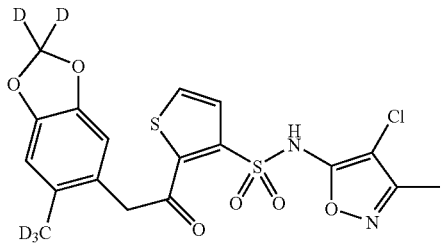

or a pharmaceutically acceptable salt thereof.

24. A compound of claim 1 having the structural formula:

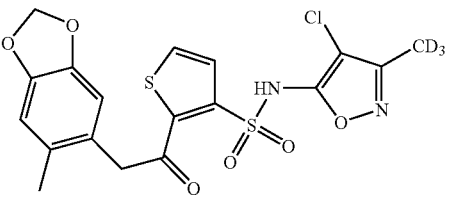

or a pharmaceutically acceptable salt thereof.

25. A compound of claim 1 having the structural formula:

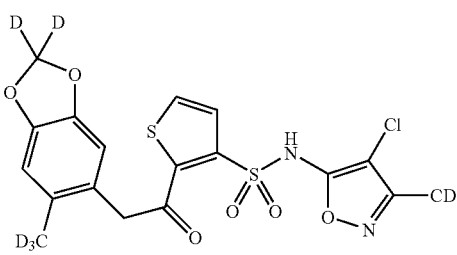

or a pharmaceutically acceptable salt thereof.

26. The pharmaceutical composition as recited in claim 9, wherein said compound has the structural formula:

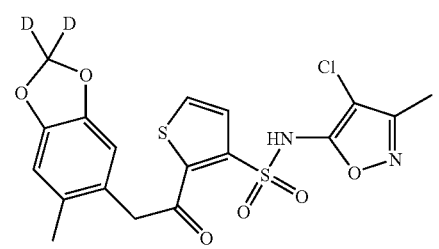

or a pharmaceutically acceptable salt thereof.

27. The pharmaceutical composition as recited in claim 9, wherein said compound has the structural formula:

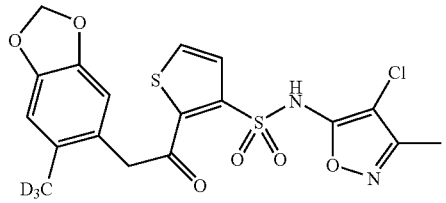

or a pharmaceutically acceptable salt thereof.

28. The pharmaceutical composition as recited in claim 9, wherein said compound has the structural formula:

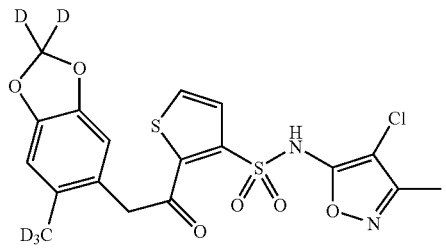

or a pharmaceutically acceptable salt thereof.

29. The pharmaceutical composition as recited in claim 9, wherein said compound has the structural formula:

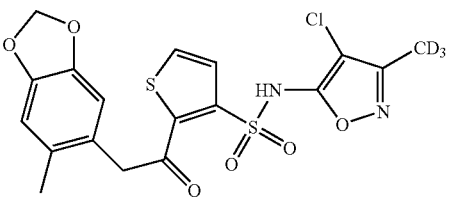

or a pharmaceutically acceptable salt thereof.

30. The pharmaceutical composition as recited in claim 9, wherein said compound has the structural formula:

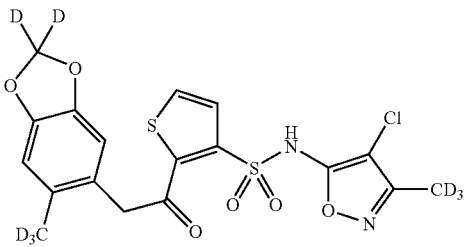

or a pharmaceutically acceptable salt thereof.

* * * * *